(12) United States Patent
Pulley et al.

(10) Patent No.: US 7,351,738 B2
(45) Date of Patent: Apr. 1, 2008

(54) SUBSTITUTED UREAS AND CARBAMATES

(75) Inventors: Shon R. Pulley, Nobelsville, IN (US); John A. Tucker, San Mateo, CA (US)

(73) Assignees: Elan Pharmaceuticals, Inc., S. San Francisco, CA (US); Pharmacia & Upjohn Company, Kalamazoo, MI (US)

( * ) Notice: Subject to any disclaimer, the term of this patent is extended or adjusted under 35 U.S.C. 154(b) by 155 days.

(21) Appl. No.: 10/723,220

(22) Filed: Nov. 26, 2003

(65) Prior Publication Data

US 2004/0209925 A1    Oct. 21, 2004

Related U.S. Application Data

(60) Provisional application No. 60/429,769, filed on Nov. 27, 2002.

(51) Int. Cl.
A61K 31/353    (2006.01)
C07C 275/12    (2006.01)
C07D 311/68    (2006.01)

(52) U.S. Cl. .................. 514/456; 549/404; 564/56
(58) Field of Classification Search ............... 549/404; 564/56; 514/456
See application file for complete search history.

(56) References Cited

U.S. PATENT DOCUMENTS

| | | | |
|---|---|---|---|
| 4,522,811 A | 6/1985 | Eppstein et al. | |
| 4,864,017 A | 9/1989 | Thaisrivongs | |
| 5,145,684 A | 9/1992 | Liversidge et al. | |
| 5,175,281 A | 12/1992 | McCall et al. | |
| 5,387,742 A | 2/1995 | Cordell | |
| 5,441,870 A | 8/1995 | Seubert et al. | |
| 5,502,187 A | 3/1996 | Ayer et al. | |
| 5,559,111 A | 9/1996 | Goschke et al. | |
| 5,578,606 A * | 11/1996 | Vazquez et al. | 514/314 |
| 5,593,846 A | 1/1997 | Schenk et al. | |
| 5,604,102 A | 2/1997 | McConlogue et al. | |
| 5,606,078 A | 2/1997 | Goschke et al. | |
| 5,612,486 A | 3/1997 | McConlogue et al. | |
| 5,641,778 A | 6/1997 | Maibaum et al. | |
| 5,719,141 A | 2/1998 | Rasetti et al. | |
| 5,720,936 A | 2/1998 | Wadsworth et al. | |
| 5,721,130 A | 2/1998 | Seubert et al. | |
| 5,744,346 A | 4/1998 | Chrysler et al. | |
| 5,766,846 A | 6/1998 | Schlossmacher et al. | |
| 5,811,633 A | 9/1998 | Wadsworth et al. | |
| 5,850,003 A | 12/1998 | McLonlogue et al. | |
| 5,877,015 A | 3/1999 | Hardy et al. | |
| 5,877,399 A | 3/1999 | Hsiao et al. | |
| 5,912,410 A | 6/1999 | Cordell | |
| 5,942,400 A | 8/1999 | Anderson et al. | |
| 6,045,829 A | 4/2000 | Liversidge et al. | |
| 6,191,166 B1 | 2/2001 | Audia et al. | |

FOREIGN PATENT DOCUMENTS

| | | |
|---|---|---|
| EP | 0 678 503 | 10/1995 |
| EP | 0 678 514 | 10/1995 |
| EP | 0 702 004 | 3/1996 |
| EP | 0 716 077 | 6/1996 |
| JP | 09124629 | * 5/1997 |
| WO | 9633187 | * 10/1996 |
| WO | WO98/22597 | 5/1998 |
| WO | WO 00/03819 | 1/2000 |
| WO | WO 00/17369 | 3/2000 |
| WO | 2000047551 | * 8/2000 |
| WO | WO 00/47618 | 8/2000 |
| WO | WO 00/77030 | 12/2000 |
| WO | WO 01/23533 | 4/2001 |
| WO | 2002014264 | * 2/2002 |
| WO | 2003040096 | * 5/2003 |
| WO | 2003090691 | * 11/2003 |
| WO | 2004022523 | * 3/2004 |

OTHER PUBLICATIONS

Arrowsmith et al., Tetrahedron Letters, 28(45) 5569-5572 (1987).
Berge, (1977) J. Pharm. Sci., 66(1):1-19.
Citron et.al., 1992, Nature 360:672-674.
Emilieu, 2000, Arch. Neurol. 57:454.
Games et.al., 1995, Nature 373:523-527.
Gould, (1986) Int. J. Pharm., 33:201-217.
Hardy, 1992, Nature Genet. 1:233-234.
Hussain et.al., 1999, Mol. Cell. Neurosci. 14:419-427.
Kang et.al., 1987, Nature 325:733-6.
Kitaguchi et. al., 1981, Nature 331:530-532.
Lin et.al., 2000, PNAS USA 97:1456-1460.
Luo et.al., 2001 Nature Neuroscience 4:231-232.
Pirttila et.al., 1999, Neuro.Lett. 249:21-4.
Sabbagh, M., et al., 1997, Alz. Dis. Rev. 3, 1-19.
Slekoe, 1991, Neuron 6:487.
Seubert et al., 1992, Nature 359:325-327.
Shibata et al., Tetrahadron Letters, 38(4), 619-620 (1997).
Sinha et.al., 1999, Nature 402:537-554.
Vasquez et al., J. Med. Chem., 38(4), 581-584 (1994).
Vassar et.al., 1999, Science 286:735-741.
Yan et.al., 1999, Nature 402:533-537.

* cited by examiner

Primary Examiner—Taofiq Solola
(74) Attorney, Agent, or Firm—McDonnell Boehnen Hulbert & Berghoff LLP

(57) ABSTRACT

The invention provides compounds of formula I:

$$R_N-T-X-N(R_{20})-CH(R_1)-C(R_2)(R_3)(OH?)...N(R_{20})-R_C$$

useful in treating Alzheimer's disease and other similar diseases. These compounds include inhibitors of the beta-secretase enzyme that are useful in the treatment of Alzheimer's disease and other diseases characterized by deposition of A beta peptide in a mammal. The compounds of the invention are useful in pharmaceutical compositions and methods of treatment to reduce A beta peptide formation.

21 Claims, No Drawings

SUBSTITUTED UREAS AND CARBAMATES

This application claims priority from U.S. Provisional Application 60/429,769, filed Nov. 27, 2002, the disclosure of which is incorporated herein in its entirety.

BACKGROUND OF THE INVENTION

1. Field of the Invention

The invention is relates to substituted ureas and carbamates. More specifically it relates to such compounds that inhibit β-secretase, an enzyme that cleaves amyloid precursor protein to produce Aβ peptide, a major component of the amyloid plaques found in the brains of Alzheimer's sufferers. Thus, the compounds of the invention are useful in treatment of Alzheimer's disease and similar diseases.

2. Description of the Related Art

Alzheimer's disease (AD) is a progressive degenerative disease of the brain primarily associated with aging. Clinical presentation of AD is characterized by loss of memory, cognition, reasoning, judgement, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurogenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39-42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, am Mamepsin. See, for example, Sindha et. al., 1999, *Nature* 402:537-554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325-327.

It has been proposed that A beta peptide accumulates as a result of APP processing by betasecretase, thus inhibition of this enzyme's activity is desirable for the treatement of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1-19.

BACE1 knockout mice fail to produce A beta, and present a normal phenotype. When crossed with transgenic mice that overexpress APP, the progeny show reduced amounts of A beta in brain extracts as compared with control animals (Luo et. al., 2001 *Nature Neuroscience* 4:231-232). This evidence further supports the proposal that inhibition of beta-secretase activity and reduction of A beta in the brain provides a therapeutic method for the treatment of AD and other beta amyloid disorders.

Published PCT application WO00/47618 entitled "Beta-Secretase Enzyme Compositions and Methods" identifies the beta-secretase enzyme and methods of its use. This publication also discloses oligopeptide inhibitors that bind the enzyme's active site and are useful in affinity column purification of the enzyme. In addition, WO00/77030 discloses tetrapeptide inhibitors of beta-secretase activity that are based on a statine molecule Various pharmaceutical agents have been proposed for the treatment of Alzheimer's disease but without any real success. U.S. Pat. No. 5,175,281 discloses 21-aminosteroids as being useful for treating Alzheimer's disease. U.S. Pat. No. 5,502,187 discloses bicyclic heterocyclic amines as being useful for treating Alzheimer's disease.

The hydroxyethylamine "nucleus" or isostere, of which the compounds of the invention is a truncated analog, has been used with success in the area of HIV protease inhibition. Many of these hydroxyethylamine compounds are known as well as how to make them. See for example, *J. Am. Chem. Soc.*, 93, 288-291 (1993), *Tetrahedron Letters*, 28(45) 5569-5572 (1987), *J. Med. Chem.*, 38(4), 581-584 (1994), *Tetrahedron Letters*, 38(4), 619-620 (1997). European Patents, numbers 702 004, 678 503, 678 514, 678 503 and 716077 by Maibaum, et al. are directed to similar isosteric strategies directed at renin inhibition. See also, U.S. Pat. No. 5,606,078 and U.S. Pat. No. 5,559,111, both to Goschke, et. al.; U.S. Pat. No. 5,719,141, to Rasetti, et. al.; and U.S. Pat. No. 5,641,778, to Maibaum, et. al.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF THE INVENTION

In a broad aspect, the invention provides compounds represented by formula I:

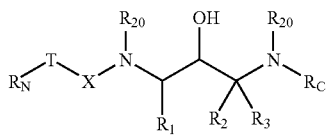

I and the pharmaceutically acceptable salts and esters thereof;

wherein X is —(C=O)—, —(C=S)—, —S(O)$_{n1}$— or —(C=N—Z), wherein Z=R$_{20}$ or —OR$_{20}$, and wherein n1 is 0, 1 or 2;

T is absent, NR$_{20}$, or O, with the proviso that when X is —(C=O), T is not absent;

wherein each R$_{20}$ is independently H, —CN, C$_{1-6}$ alkyl or alkenyl, C$_{1-6}$ haloalkyl or C$_{4-7}$ cycloalkyl, with the proviso that when Z is R$_{20}$ or —OR$_{20}$, R$_{20}$ is not —CN;

wherein R$_1$ is —(CH$_2$)$_{1-2}$—S(O)$_{0-2}$—(C$_1$-C$_6$ alkyl), or

C$_1$-C$_{10}$ alkyl optionally substituted with 1, 2, or 3 groups independently selected from halogen, —OH, =O, —SH, —C≡N, —CF$_3$, —C$_1$-C$_3$ alkoxy, amino, mono- or dialkylamino, —N(R)C(O)R'—, —OC(=O)-amino and —OC(=O)-mono- or dialkylamino, or C$_2$-C$_6$ alkenyl or C$_2$-C$_6$ alkynyl, each of which is optionally substituted with 1, 2, or 3 groups independently selected from halogen, —OH, —SH, —C≡N, —CF$_3$, C$_1$-C$_3$ alkoxy, amino, and mono- or dialkylamino, or aryl, heteroaryl, heterocyclyl, —C$_1$-C$_6$ alkyl-aryl, —C$_1$-C$_6$ alkyl-heteroaryl, or —C$_1$-C$_6$ alkyl-heterocyclyl, where the ring portions of each are optionally substituted with 1, 2, 3, or 4 groups independently selected from halogen, —OH, —SH, —C≡N, —NR$_{105}$R'$_{105}$, —CO$_2$R, —N(R)COR', or —N(R)SO$_2$R', —C(=O)—(C$_1$-C$_4$) alkyl, —SO$_2$-amino, —SO$_2$-mono or dialkylamino, —C(=O)-amino, —C(=O)-mono or dialkylamino, —SO$_2$—(C$_1$-C$_4$) alkyl, or C$_1$-C$_6$ alkoxy optionally substituted with 1, 2, or 3 groups which are independently selected from halogen, or C$_3$-C$_7$ cycloalkyl optionally substituted with 1, 2, or 3 groups independently selected from halogen, —OH, —SH, —C≡N, —CF$_3$, C$_1$-C$_3$ alkoxy, amino, —C$_1$-C$_6$ alkyl and mono- or dialkylamino, or C$_1$-C$_{10}$ alkyl optionally substituted with 1, 2, or 3 groups independently selected from halogen, —OH, —SH, —C≡N, —CF$_3$, —C$_1$-C$_3$ alkoxy, amino, mono- or dialkylamino and —C$_1$-C$_3$ alkyl, or C$_2$-C$_{10}$ alkenyl or C$_2$-C$_{10}$ alkynyl each of which is optionally substituted with 1, 2, or 3 groups independently selected from halogen, —OH, —SH, —C≡N, —CF$_3$, C$_1$-C$_3$ alkoxy, amino, C$_1$-C$_6$ alkyl and mono- or dialkylamino; and the heterocyclyl group is optionally further substituted with oxo;

R and R' independently are hydrogen, C$_1$-C$_{10}$ alkyl, C$_1$-C$_{10}$ alkylaryl or C$_1$-C$_{10}$ alkylheteroaryl;

wherein R$_C$ is (I) —[—(CH$_2$)$_{(0-8)}$—(CH) (alkyl$_1$) (alkyl$_2$)], where alkyl$_1$ and alkyl$_2$ are straight or branched C$_{2-10}$ alkanyl, alkenyl or alkynyl, and wherein alkyl$_1$ and alkyl$_2$ attach to the same or different methylene carbon with the remaining open methylene valences occupied by hydrogen, thus forming a branched alkyl chain having between 8 and 20 carbon atoms in total;

the alkyl groups, alkyl$_1$ and alkyl$_2$ being optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, —O-phenyl, —C(O)C$_1$-C$_3$ alkyl; —NR$_{1-a}$R$_{1-b}$ where R$_{1-a}$ and R$_{1-b}$ are —H or C$_1$-C$_6$ alkyl, —OC=O NR$_{1-a}$R$_{1-b}$ where R$_{1-a}$ and R$_{1-b}$ are as defined above, —S(=O)$_{0-2}$ R$_{1-a}$ where R$_{1-a}$ is as defined above, —NR$_{1-a}$C=O NR$_{1-a}$R$_{1-b}$ where R$_{1-a}$ and R$_{1-b}$ are as defined above, —C=O NR$_{1-a}$R$_{1-b}$ where R$_{1-a}$ and R$_{1-b}$ are as defined above, and —S(=O)$_2$ NR$_{1-a}$R$_{1-b}$ where R$_{1a}$ and R$_{1-b}$ are as defined above (II) —(C(Rc-x)(Rc-y))$_{(0-4)}$-Rc-cycle wherein all Rc-x and Rc-y are independently chosen from:

H

C$_1$-C$_6$ alkyl

C$_1$-C$_6$ alkoxy

C$_1$-C$_6$ alkyl-(C=O)—O—C$_1$-C$_6$ alkyl

C$_2$-C$_6$ alkenyl or alkynyl

—(CH$_2$)$_{0-4}$-Rc-cycle where Rc-cycle is as defined below and Rc-x and Rc-y may be taken together with the methylene carbon to which they jointly attach to form a spirocyclic ring of 3 to 7 atoms comprising carbon and up to 2 of O, S(O)$_{(0-2)}$ and NR$_{a'}$ wherein is R$_{a'}$ is H or C$_{1-4}$ alkyl;

wherein the spirocyclic ring may be fused to another ring to provide a bicyclic ring system comprising carbon and up to 2 of O, S(O)$_{(0-2)}$ and NR$_{a''}$ and comprising up to 9 atoms in total including, Rc-cycle is any aryl, heteroaryl, cycloalkyl or heteroaryl ring or any fused ring combination thereof wherein the total number of rings fused therein of same and of different type does not exceed 3 wherein Rc-cycle is optionally substituted with up to four substituents independently chosen from:

(1) C$_1$-C$_6$ alkyl optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$ where R$_{1-a}$ and R$_{1-b}$ are as defined above, (2) C$_2$-C$_6$ alkenyl or alkynyl with one or two unsaturated bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$ where are as defined above, (3) —F, Cl, —Br or —I, (4) C$_1$-C$_6$ alkoxy, (5) —C$_1$-C$_6$ alkoxy optionally substituted with one, two, or three of —F, (6) —NR$_{N-6}$R$_{N-7}$ where R$_{N-6}$ and R$_{N-7}$ are the same or different and are selected from the group consisting of:

(a) —H, (b) —C$_1$-C$_6$ alkyl optionally substituted with one substitutent selected from the group consisting of:

(i) —OH, and (ii) —NH$_2$, (c) —C$_1$-C$_6$ alkyl optionally substituted with one to three —F, —Cl, —Br, or —I, (d) —$C_3$-$C_7$ cycloalkyl,
(e) —($C_1$-$C_2$ alkyl)-($C_3$-$C_7$ cycloalkyl),
(f) —($C_1$-$C_6$ alkyl)-O—($C_1$-$C_3$ alkyl),
(g) —$C_2$-$C_6$ alkenyl with one or two double bonds,
(h) —$C_2$-$C_6$ alkynyl with one or two triple bonds,
(i) —$C_1$-$C_6$ alkyl chain with one double bond and one triple bond,
(j) —$R_{1\text{-}aryl}$ where $R_{1\text{-}aryl}$ is as defined above, and
(k) —$R_{1\text{-}heteroaryl}$ where $R_{1\text{-}heteroaryl}$ is as defined above,
(7) —OH,
(8) —C≡N,
(9) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, and —$NR_{1\text{-}a}R_{1\text{-}b}$ where $R_{1\text{-}a}$ and $R_{1\text{-}b}$ are —H or $C_1$-$C_6$ alkyl,
(10) —CO—($C_1$-$C_4$ alkyl),
(11) —$SO_2$—$NR_{1\text{-}a}R_{1\text{-}b}$ where $R_{1\text{-}a}$ and $R_{1\text{-}b}$ are as defined above,
(12) —CO—$NR_{1\text{-}a}R_{1\text{-}b}$ where $R_{1\text{-}a}$ and $R_{1\text{-}b}$ are as defined above,
(13) —$SO_2$—($C_1$-$C_4$ alkyl), and when there is a saturated carbon atom in Rc-cycle
(14) oxo,
(15) oxime
(16) ketal rings of 5 to 7 members and
(17) a spirocyclic ring having from 3 to 7 atoms comprising carbon and when the ring size is 4-7 atoms optionally up to 2 of O, S(O)$_{(0-2)}$ and $NR_a$,
(III) —$(CR_{C\text{-}x}R_{C\text{-}y})_{0-4}$-heteroaryl,
(IV) —$(CR_{C\text{-}x}R_{C\text{-}y})_{0-4}$-aryl-aryl,
(V) —$(CR_{C\text{-}x}R_{C\text{-}y})_{0-4}$-aryl-heteroaryl,
(VI) —$(CR_{C\text{-}x}R_{C\text{-}y})_{0-4}$-heteroaryl-aryl,
(VII) —$(CR_{C\text{-}x}R_{C\text{-}y})_{0-4}$-heteroaryl-heteroaryl,
(VIII) —$(CR_{C\text{-}x}R_{C\text{-}y})_{0-4}$-aryl-heterocycle,
(IX) —$(CR_{C\text{-}x}R_{C\text{-}y})_{0-4}$-heteroaryl-heterocycle,
(XI) —$(CR_{C\text{-}x}R_{C\text{-}y})_{0-4}$-heterocycle-aryl,
(XII) —$(CR_{C\text{-}x}R_{C\text{-}y})_{0-4}$-heterocycle-heteroaryl,
(XI) —$(CR_{C\text{-}x}R_{C\text{-}y})_{0-4}$-heterocycle-heterocycle,
(XIII) —$[C(R_{C\text{-}1})(R_{C\text{-}2})]_{1\text{-}3}$—$[CO]_{0\text{-}1}$—N—$(R_{C\text{-}3})_2$
where each $R_{C\text{-}1}$ is the same or different and is selected from the group consisting of: H, $C_{1\text{-}4}$ alkyl and $C_{1\text{-}4}$ alkoxy and where each $R_{C\text{-}2}$ and $R_{C\text{-}3}$ is independently selected from (A) —$C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O— phenyl, and —$NR_{1\text{-}a}R_{1\text{-}b}$ where $R_{1\text{-}a}$ and $R_{1\text{-}b}$ are as defined above, (B) $C_2$-$C_6$ alkenyl or alkynyl with one or two unsaturated bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O— phenyl, and —$NR_{1\text{-}a}R_{1\text{-}b}$ where $R_{1\text{-}a}$ and $R_{1\text{-}b}$ are as defined above, (C) —$(CH_2)_{1\text{-}2}$—S(O)$_{0\text{-}2}$—($C_1$-$C_6$ alkyl),
(D) —$(CH_2)_{0\text{-}4}$—$C_3$-$C_7$ cycloalkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O— phenyl, —$NR_{1\text{-}a}R_{1\text{-}b}$ where $R_{1\text{-}a}$ and $R_{1\text{-}b}$ are as defined above,
(E) —$(CH_2)_{0\text{-}4}$-5-7 membered heterocycle optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O— phenyl, oxo, —$NR_{1\text{-}a}R_{1\text{-}b}$ where $R_{1\text{-}a}$ and $R_{1\text{-}b}$ are as defined above, (XIV) —CH(aryl)$_2$ where each aryl is the same or different, (XV) —CH(heteroaryl)$_2$ where each heteroaryl is the same or different and are as defined above, (XVI) —CH(aryl)(heteroaryl), wherein $R_N$ is $R'_{100}$, —$(CRR')_{1\text{-}6}R'_{100}$, —$(CRR')_{0\text{-}6}R_{100}$, —$(CRR')_{1\text{-}6}$—O—$R'_{100}$, —$(CRR')_{1\text{-}6}$—S—$R'_{100}$, —$(CRR')_{1\text{-}6}$—C(=O)—$R_{100}$, —$(CRR')_{1\text{-}6}$—$SO_2$—$R'_{100}$, —$(CRR')_{1\text{-}6}$—$NR'_{100}$—$R'_{100}$ or —$SO_2R'_{100}$, with the proviso that when $R_N$ is —$SO_2R'_{100}$, X is not —S(=O)$_n$— or —C(=S)—; wherein $R_{100}$ and $R'_{100}$ independently represent aryl, heteroaryl, -aryl-W-aryl, -aryl-W-heteroaryl, -aryl-W-heterocyclyl, -heteroaryl-W-aryl, -heteroaryl-W-heteroaryl, -heteroaryl-W-heterocyclyl, -heterocyclyl-W-aryl, -heterocyclyl-W-heteroaryl, -heterocyclyl-W-heterocyclyl, —CH[$(CH_2)_{0\text{-}2}$—O—$R_{150}$]—$(CH_2)_{0\text{-}2}$-aryl, —CH[$(CH_2)_{0\text{-}2}$—O—$R_{150}$]—$(CH_2)_{0\text{-}2}$-heterocyclyl or —CH[$(CH_2)_{0\text{-}2}$—O—$R_{150}$]—$(CH_2)_{0\text{-}2}$-heteroaryl, where the ring portions of each are optionally substituted with 1, 2, or 3 groups independently selected from —OR, —$NO_2$, halogen, —C≡N, —$OCF_3$, —$CF_3$, —$(CH_2)_{0\text{-}4}$—O—P(=O)(OR)(OR'), —$(CH_2)_{0\text{-}4}$—CO—$NR_{105}R'_{105}$, —$(CH_2)_{0\text{-}4}$—O—$(CH_2)_{0\text{-}4}$—$CONR_{102}R_{102}'$, —$(CH_2)_{0\text{-}4}$—CO—($C_1$-$C_{12}$ alkyl), —$(CH_2)_{0\text{-}4}$—CO—($C_2$-$C_{12}$ alkenyl), —$(CH_2)_{0\text{-}4}$—CO—($C_2$-$C_{12}$ alkynyl), —$(CH_2)_{0\text{-}4}$—CO—$(CH_2)_{0\text{-}4}$ ($C_3$-$C_7$ cycloalkyl), —$(CH_2)_{0\text{-}4}$—$R_{110}$, —$(CH_2)_{0\text{-}4}$—$R_{120}$, —$(CH_2)_{0\text{-}4}$—$R_{130}$, —$(CH_2)_{0\text{-}4}$—CO—$R_{110}$, —$(CH_2)_{0\text{-}4}$—CO—$R_{120}'$, —$(CH_2)_{0\text{-}4}$—CO—$R_{130}$, —$(CH_2)_{0\text{-}4}$—CO—$R_{140}$, —$(CH_2)_{0\text{-}4}$—CO—O—$R_{150}$, —$(CH_2)_{0\text{-}4}$—$SO_2$—$NR_{105}R'_{105}$, —$(CH_2)_{0\text{-}4}$—SO—($C_1$-$C_8$ alkyl), —$(CH_2)_{0\text{-}4}$—$SO_2$—($C_1$-$C_{12}$ alkyl), —$(CH_2)_{0\text{-}4}$-$SO_2$—$(CH_2)_{0\text{-}4}$—($C_3$-$C_7$ cycloalkyl), —$(CH_2)_{0\text{-}4}$—$N(R_{150})$—CO—O—$R_{150}$, —$(CH_2)_{0\text{-}4}$—$N(R_{150})$—CO—$N(R_{150})_2$, —$(CH_2)_{0\text{-}4}$—$N(R_{150})$—CS—$N(R_{150})_2$, —$(CH_2)_{0\text{-}4}$—$N(R_{150})$—CO—$R_{105}$, —$(CH_2)_{0\text{-}4}$—$NR_{105}R'_{105}$, —$(CH_2)_{0\text{-}4}$—$R_{140}$, —$(CH_2)_{0\text{-}4}$—O—CO—($C_1$-$C_6$ alkyl), —$(CH_2)_{0\text{-}4}$—O—P(O)—(O—$R_{110}$)$_2$, —$(CH_2)_{0\text{-}4}$—O—CO—N($R_{150}$)$_2$, —$(CH_2)_{0\text{-}4}$—O—CS—$N(R_{150})_2$, —$(CH_2)_{0\text{-}4}$—O—($R_{150}$), —$(CH_2)_{0\text{-}4}$—O—$R_{150}$—COOH, —$(CH_2)_{0\text{-}4}$—S—($R_{150}$), —$(CH_2)_{0\text{-}4}$—N($R_{150}$)—$SO_2$—$R_{105}$, —$(CH_2)_{0\text{-}4}$—$C_3$-$C_7$ cycloalkyl, ($C_2$-$C_{10}$)alkenyl, or ($C_2$-$C_{10}$)alkynyl, or $R_{100}$ is $C_1$-$C_{10}$ alkyl optionally substituted with 1, 2, or 3 $R_{115}$ groups, or $R_{100}$ is —($C_1$-$C_6$ alkyl)-O—$C_1$-$C_6$ alkyl) or —($C_1$-$C_6$ alkyl)-S—($C_1$-$C_6$ alkyl), each of which is optionally substituted with 1, 2, or 3 $R_{115}$ groups, or $R_{100}$ is $C_3$-$C_8$ cycloalkyl optionally substituted with 1, 2, or 3 $R_{115}$ groups;

W is —$(CH_2)_{0\text{-}4}$—, —O—, —S(O)$_{0\text{-}2}$—, —$N(R_{135})$—, —CR(OH)— or —C(O)—;

$R_{102}$ and $R_{102}'$ independently are hydrogen, or $C_1$-$C_{10}$ alkyl optionally substituted with 1, 2, or 3 groups that are independently halogen, aryl or —$R_{110}$;

$R_{105}$ and $R'_{105}$ independently represent —H, —$R_{110}$, —$R_{120}$, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), $C_2$-$C_6$ alkenyl, $C_2$-$C_6$ alkynyl, or $C_1$-$C_6$ alkyl chain with one double bond and one triple bond, or $C_1$-$C_6$ alkyl optionally substituted with —OH or —$NH_2$; or, $C_1$-$C_6$ alkyl optionally substituted with 1, 2, or 3 groups independently selected from halogen, or $R_{105}$ and $R'_{105}$ together with the atom to which they are attached form a 3 to 7 membered carbocylic ring, where one member is optionally a heteratom selected from —O—, —$S(O)_{0-2}$—, —$N(R_{135})$—, the ring being optionally substituted with 1, 2 or three $R_{140}$ groups;

$R_{115}$ at each occurrence is independently halogen, —OH, —$CO_2R_{102}$, —$C_1$-$C_6$ thioalkoxy, —$CO_2$-phenyl, —$NR_{105}R'_{135}$, —$SO_2$—($C_1$-$C_8$ alkyl), —$C(=O)R_{180}$, $R_{180}$, —$CONR_{105}R'_{105}$, —$SO_2NR_{105}R'_{105}$, —NH—CO—($C_1$-$C_6$ alkyl), —NH—C(=O)—OH, —NH—C(=O)—OR, —NH—C(=O)—O-phenyl, —O—C(=O)—($C_1$-$C_6$ alkyl), —O—C(=O)-amino, —O—C(=O)-mono- or dialkylamino, —O—C(=O)-phenyl, —O—($C_1$-$C_6$ alkyl)-$CO_2H$, —NH—$SO_2$—($C_1$-$C_6$ alkyl), $C_1$-$C_6$ alkoxy or $C_1$-$C_6$ haloalkoxy;

$R_{135}$ is $C_1$-$C_6$ alkyl, $C_2$-$C_6$ alkenyl, $C_2$-$C_6$ alkynyl, $C_3$-$C_7$ cycloalkyl, —$(CH_2)_{0-2}$-(aryl), —$(CH_2)_{0-2}$-(heteroaryl), or —$(CH_2)_{0-2}$-(heterocyclyl);

$R_{140}$ is heterocyclyl optionally substituted with 1, 2, 3, or 4 groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, and =O;

$R_{150}$ is hydrogen, $C_3$-$C_7$ cycloalkyl, —($C_1$-$C_2$ alkyl)-($C_3$-$C_7$ cycloalkyl), $C_2$-$C_6$ alkenyl, $C_2$-$C_6$ alkynyl, $C_1$-$C_6$ alkyl with one double bond and one triple bond, —$R_{110}$, —$R_{120}$, or $C_1$-$C_6$ alkyl optionally substituted with 1, 2, 3, or 4 groups independently selected from —OH, —$NH_2$, $C_1$-$C_3$ alkoxy, $R_{110}$, and halogen;

$R_{150}'$ is $C_3$-$C_7$ cycloalkyl, —($C_1$-$C_3$ alkyl)-($C_3$-$C_7$ cycloalkyl), $C_2$-$C_6$ alkenyl, $C_2$-$C_6$ alkynyl, $C_1$-$C_6$ alkyl with one double bond and one triple bond, —$R_{110}$, —$R_{120}$, or $C_1$-$C_6$ alkyl optionally substituted with 1, 2, 3, or 4 groups independently selected from —OH, —$NH_2$, $C_1$-$C_3$ alkoxy, $R_{110}$, and halogen;

$R_{180}$ is selected from morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl, each of which is optionally substituted with 1, 2, 3, or 4 groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, and =O;

$R_{110}$ is aryl optionally substituted with 1 or 2 $R_{125}$ groups;

$R_{125}$ at each occurrence is independently halogen, amino, mono- or dialkylamino, —OH, —C≡N, —$SO_2$—$NH_2$, —$SO_2$—NH—$C_1$-$C_6$ alkyl, —$SO_2$—N($C_1$-$C_6$ alkyl)$_2$, —$SO_2$—($C_1$-$C_4$ alkyl), —CO—$NH_2$, —CO—NH—$C_1$-$C_6$ alkyl, or —CO—N($C_1$-$C_6$ alkyl)$_2$, or $C_1$-$C_6$ alkyl, $C_2$-$C_6$ alkenyl or $C_2$-$C_6$ alkynyl, each of which is optionally substituted with 1, 2 or 3 groups that are independently selected from $C_1$-$C_3$ alkyl, halogen, —OH, —SH, —C≡N, —$CF_3$, $C_1$-$C_3$ alkoxy, amino, and mono- and dialkylamino, or $C_1$-$C_6$ alkoxy optionally substituted with one, two or three of halogen;

$R_{120}$ is heteroaryl, which is optionally substituted with 1 or 2 $R_{125}$ groups; and $R_{130}$ is heterocyclyl optionally substituted with 1 or 2 $R_{125}$ groups; and $R_2$ is selected from the group consisting of H; $C_1$-$C_6$ alkyl, optionally substituted with 1, 2, or 3 substituents that are independently selected from the group consisting of $C_1$-$C_3$ alkyl, halogen, —OH, —SH, —C≡N, —$CF_3$, $C_1$-$C_3$ alkoxy, and —$NR_{1-a}R_{1-b}$; wherein $R_{1-a}$ and $R_{1-b}$ are —H or $C_1$-$C_6$ alkyl; —$(CH_2)_{0-4}$-aryl; —$(CH_2)_{0-4}$-heteroaryl; $C_2$-$C_6$ alkenyl; $C_2$-$C_6$ alkynyl; —$CONR_{N-2}R_{N-3}$; —$SO_2NR_{N-2}R_{N-3}$; —$CO_2H$; and —$CO_2$—($C_1$-$C_4$ alkyl);

$R_3$ is selected from the group consisting of H; $C_1$-$C_6$ alkyl, optionally substituted with 1, 2, or 3 substituents independently selected from the group consisting of $C_1$-$C_3$ alkyl, halogen, —OH, —SH, —C≡N, —$CF_3$, $C_1$-$C_3$ alkoxy, and —$NR_{1-a}R_{1-b}$; —$(CH_2)_{0-4}$-aryl; —$(CH_2)_{0-4}$-heteroaryl; $C_2$-$C_6$ alkenyl; $C_2$-$C_6$ alkynyl; —CO—$NR_{N-2}R_{N-3}$; —$SO_2$—$NR_{N-2}R_{N-3}$; —$CO_2H$; and —CO—O—($C_1$-$C_4$ alkyl)

wherein $R_{N-2}$ and $R_{N-3}$ at each occurrence are independently selected from the group consisting of —$C_1$-$C_8$ alkyl optionally substituted with 1, 2, or 3 groups independently selected from the group consisting of —OH, —$NH_2$, phenyl and halogen; —$C_3$-$C_8$ cycloalkyl; —($C_1$-$C_2$ alkyl)-($C_3$-$C_8$ cycloalkyl); —($C_1$-$C_6$ alkyl)-O—($C_1$-$C_3$ alkyl); —$C_2$-$C_6$ alkenyl; —$C_2$-$C_6$ alkynyl; —$C_1$-$C_6$ alkyl chain with one double bond and one triple bond; aryl; heteroaryl; heterocycloalkyl; or $R_{N-2}$, $R_{N-3}$ and the nitrogen to which they are attached form a 5, 6, or 7 membered heterocycloalkyl or heteroaryl group, wherein said heterocycloalkyl or heteroaryl group is optionally fused to a benzene, pyridine, or pyrimidine ring, and said groups are unsubstituted or substituted with 1, 2, 3, 4, or 5 groups that at each occurrence are independently $C_1$-$C_6$ alkyl, $C_1$-$C_6$ alkoxy, halogen, halo $C_1$-$C_6$ alkyl, halo $C_1$-$C_6$ alkoxy, —CN, —$NO_2$, —$NH_2$, NH($C_1$-$C_6$ alkyl), N($C_1$-$C_6$ alkyl) ($C_1$-$C_6$ alkyl), —OH, —C(O)$NH_2$, —C(O)NH ($C_1$-$C_6$ alkyl), —C(O)N($C_1$-$C_6$ alkyl) ($C_1$-$C_6$ alkyl), $C_1$-$C_6$ alkoxy $C_1$-$C_6$ alkyl, $C_1$-$C_6$ thioalkoxy, and $C_1$-$C_6$ thioalkoxy $C_1$-$C_6$ alkyl; or wherein, $R_2$, $R_3$ and the carbon to which they are attached form a carbocycle of three thru seven carbon atoms, wherein one carbon atom is optionally replaced by a group selected from —O—, —S—, —$SO_2$—, and —$NR_{N-2}$—.

The invention also provides methods for preparing compounds of formulas I or IA and the pharmaceutically acceptable salts and esters thereof where variables are as defined herein.

The invention also includes a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which comprises administration of a therapeutically effective amount of a compound of formula I or IA or a pharmaceutically acceptable salt or ester thereof.

The invention also includes methods for inhibiting beta-secretase activity, for inhibiting cleavage of amyloid precursor protein (APP), in a reaction mixture, at a site between Met596 and Asp597, numbered for the APP-695 amino acid isotype; or at a corresponding site of an isotype or mutant thereof, for inhibiting production of amyloid beta peptide (A beta) in a cell, for inhibiting the production of beta-amyloid plaque in an animal, and for treating or preventing a disease characterized by beta-amyloid deposits in the brain which comprise administration of a therapeutically effective amount of a compound of formula I or IA or a pharmaceutically acceptable salt or ester thereof.

The invention also includes a pharmaceutical composition that comprises a compound of formula I or IA or a pharmaceutically acceptable salt or ester thereof, and one or more pharmaceutically acceptable carriers.

The invention also includes the use of a compound of formula I or IA or a pharmaceutically acceptable salt or ester thereof for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

The invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The invention also provides intermediates and methods useful for preparing the compounds of Formula I and IA, or pharmaceutically acceptable salts or esters thereof.

The compounds of the invention possess beta-secretase inhibitory activity. The inhibitory activities of the compounds of the invention are readily demonstrated, for example, using one or more of the assays described herein or known in the art.

DETAILED DESCRIPTION OF THE INVENTION

As noted above, a broad aspect of the invention is directed to a compound of formula I and to the pharmaceutically acceptable salts and esters thereof.

In a preferred embodiment, when X is $SO_2$, T is not absent. In alternative embodiment, $R_N$ is

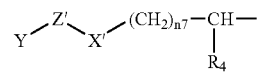

wherein $R_4$ is selected from the group consisting of H; $NH_2$; —NH—$(CH_2)_{n6}$—$R_{4-1}$; —$NHR_8$; —$NR_{50}C(O)R_5$; $C_1$-$C_4$ alkyl-NHC(O)$R_5$; —$(CH_2)_{0-4}R_8$; —O—$C_1$-$C_4$ alkanoyl; OH; $C_6$-$C_{10}$ aryloxy optionally substituted with 1, 2, or 3 groups that are independently halogen, $C_1$-$C_4$ alkyl, —$CO_2H$, —C(O)—$C_1$-$C_4$ alkoxy, or $C_1$-$C_4$ alkoxy; $C_1$-$C_6$ alkoxy; aryl $C_1$-$C_4$ alkoxy; —$NR_{50}CO_2R_{51}$; —$C_1$-$C_4$ alkyl-$NR_{50}CO_2R_{51}$; —C≡N; —$CF_3$; —$CF_2$—$CF_3$; —C≡CH; —$CH_2$—CH=$CH_2$—$(CH_2)_{1-4}$—$R_{4-1}$; —$(CH_2)_{1-4}$—NH—$R_{4-1}$; —O—$(CH_2)_{n6}$—$R_{4-1}$; —S—$(CH_2)_{n6}$—$R_{4-1}$; —$(CH_2)_{0-4}$—NHC(O)—$(CH_2)_{0-6}$—$R_{52}$; —$(CH_2)_{0-4}$—$R_{53}$—$(CH_2)_{0-4}$—$R_{54}$;

wherein $n_6$ is 0, 1, 2, or 3;

$n_7$ is 0, 1, 2, or 3;

$R_{4-1}$ is selected from the group consisting of —$SO_2$—($C_1$-$C_8$ alkyl), —SO—($C_1$-$C_8$ alkyl), —S—($C_1$-$C_8$ alkyl), —S—CO—($C_1$-$C_6$ alkyl), —$SO_2$—$NR_{4-2}R_{4-3}$; —CO—$C_1$-$C_2$ alkyl; —CO—$NR_{4-3}R_{4-4}$;

$R_{4-2}$ and $R_{4-3}$ are independently H, $C_1$-$C_3$ alkyl, or $C_3$-$C_6$ cycloalkyl;

$R_{4-4}$ is alkyl, arylalkyl, alkanoyl, or arylalkanoyl;

$R_{4-6}$ is —H or $C_1$-$C_6$ alkyl;

$R_5$ is selected from the group consisting of $C_3$-$C_7$ cycloalkyl; $C_1$-$C_6$ alkyl optionally substituted with 1, 2, or 3 groups that are independently halogen, —$NR_6R_7$, $C_1$-$C_4$ alkoxy, $C_5$-$C_6$ heterocycloalkyl, $C_5$-$C_6$ heteroaryl, $C_6$-$C_{10}$ aryl, $C_3$-$C_7$ cycloalkyl $C_1$-$C_4$ alkyl, —S—$C_1$-$C_4$ alkyl, —$SO_2$—$C_1$-$C_4$ alkyl, —$CO_2H$, —$CONR_6R_7$, —$CO_2$—$C_1$-$C_4$ alkyl, $C_6$-$C_{10}$ aryloxy; heteroaryl optionally substituted with 1, 2, or 3 groups that are independently $C_1$-$C_4$ alkyl, $C_1$-$C_4$ alkoxy, halogen, $C_1$-$C_4$ haloalkyl, or OH; heterocycloalkyl optionally substituted with 1, 2, or 3 groups that are independently $C_1$-$C_4$ alkyl, $C_1$-$C_4$ alkoxy, halogen, or $C_2$-$C_4$ alkanoyl; aryl optionally substituted with 1, 2, 3, or 4 groups that are independently halogen, OH, $C_1$-$C_4$ alkyl, $C_1$-$C_4$ alkoxy, or $C_1$-$C_4$ haloalkyl; and —$NR_6R_7$; wherein $R_6$ and $R_7$ are independently selected from the group consisting of H, $C_1$-$C_6$ alkyl, $C_2$-$C_6$ alkanoyl, phenyl, —$SO_2$—$C_1$-$C_4$ alkyl, phenyl $C_1$-$C_4$ alkyl;

$R_8$ is selected from the group consisting of —$SO_2$—heteroaryl, —$SO_2$-aryl, —$SO_2$-heterocycloalkyl, —$SO_2$—$C_1$-$C_{10}$ alkyl, —$C(O)NHR_9$, heterocycloalkyl, —S—$C_1$-$C_6$ alkyl, —S—$C_2$-$C_4$ alkanoyl, wherein $R_9$ is aryl $C_1$-$C_4$ alkyl, $C_1$-$C_6$ alkyl, or H;

$R_{50}$ is H or $C_1$-$C_6$ alkyl;

$R_{51}$ is selected from the group consisting of aryl $C_1$-$C_4$ alkyl; $C_1$-$C_6$ alkyl optionally substituted with 1, 2, or 3 groups that are independently halogen, cyano, heteroaryl, —$NR_6R_7$, —$C(O)NR_6R_7$, $C_3$-$C_7$ cycloalkyl, or —$C_1$-$C_4$ alkoxy; heterocycloalkyl optionally substituted with 1 or 2 groups that are independently $C_1$-$C_4$ alkyl, $C_1$-$C_4$ alkoxy, halogen, $C_2$-$C_4$ alkanoyl, aryl $C_1$-$C_4$ alkyl, and —$SO_2$ $C_1$-$C_4$ alkyl; alkenyl; alkynyl; heteroaryl optionally substituted with 1, 2, or 3 groups that are independently OH, $C_1$-$C_4$ alkyl, $C_1$-$C_4$ alkoxy, halogen, $NH_2$, $NH(C_1$-$C_6$ alkyl) or $N(C_1$-$C_6$ alkyl)($C_1$-$C_6$ alkyl); heteroarylalkyl optionally substituted with 1, 2, or 3 groups that are independently $C_1$-$C_4$ alkyl, $C_1$-$C_4$ alkoxy, halogen, $NH_2$, $NH(C_1$-$C_6$ alkyl) or $N(C_1$-$C_6$ alkyl)($C_1$-$C_6$ alkyl); aryl; heterocycloalkyl; $C_3$-$C_8$ cycloalkyl; and cycloalkylalkyl; wherein the aryl; heterocycloalkyl, $C_3$-$C_8$ cycloalkyl, and cycloalkylalkyl groups are optionally substituted with 1, 2, 3, 4 or 5 groups that are independently halogen, CN, $NO_2$, $C_1$-$C_6$ alkyl, $C_1$-$C_6$ alkoxy, $C_2$-$C_6$ alkanoyl, $C_1$-$C_6$ haloalkyl, $C_1$-$C_6$ haloalkoxy, hydroxy, $C_1$-$C_6$ hydroxyalkyl, $C_1$-$C_6$ alkoxy $C_1$-$C_6$ alkyl, $C_1$-$C_6$ thioalkoxy, $C_1$-$C_6$ thioalkoxy $C_1$-$C_6$ alkyl, or $C_1$-$C_6$ alkoxy $C_1$-$C_6$ alkoxy;

$R_{52}$ is heterocycloalkyl, heteroaryl, aryl, cycloalkyl, —$S(O)_{0-2}$—$C_1$-$C_6$ alkyl, $CO_2H$, —$C(O)NH_2$, —$C(O)NH(alkyl)$, —$C(O)N(alkyl)(alkyl)$, —$CO_2$-alkyl, —NH—$S(O)_{0-2}$—$C_1$-$C_6$ alkyl, —$N(alkyl)S(O)_{0-2}$—$C_1$-$C_6$ alkyl, —$S(O)_{0-2}$-heteroaryl, —$S(O)_{0-2}$-aryl, —NH(arylalkyl), —$N(alkyl)(arylalkyl)$, thioalkoxy, or alkoxy, each of which is optionally substituted with 1, 2, 3, 4, or 5 groups that are independently alkyl, alkoxy, thioalkoxy, halogen, haloalkyl, haloalkoxy, alkanoyl, $NO_2$, CN, alkoxycarbonyl, or aminocarbonyl;

$R_{53}$ is absent, —O—, —C(O)—, —NH—, —N(alkyl)-, —NH—$S(O)_{0-2}$—, —N(alkyl)-$S(O)_{0-2}$—, —$S(O)_{0-2}$—NH—, —$S(O)_{0-2}$—N(alkyl)-, —NH—C(S)—, or —N(alkyl)-C(S)—;

$R_{54}$ is heteroaryl, aryl, arylalkyl, heterocycloalkyl, $CO_2H$, —$CO_2$-alkyl, —$C(O)NH(alkyl)$, —$C(O)N(alkyl)(alkyl)$, —$C(O)NH_2$, $C_1$-$C_8$ alkyl, OH, aryloxy, alkoxy, arylalkoxy, $NH_2$, NH(alkyl), N(alkyl) (alkyl), or —$C_1$-$C_6$ alkyl-$CO_2$—$C_1$-$C_6$ alkyl, each of which is optionally substituted with 1, 2, 3, 4, or 5 groups that are independently alkyl, alkoxy, $CO_2H$, —$CO_2$-alkyl, thioalkoxy, halogen, haloalkyl, haloalkoxy, hydroxyalkyl, alkanoyl, $NO_2$, CN, alkoxycarbonyl, or aminocarbonyl;

X' is selected from the group consisting of —$C_1$-$C_6$ alkylidenyl optionally optionally substituted with 1, 2, or 3 methyl groups; and —$NR_{4-6}$—; or $R_4$ and $R_{4-6}$ combine to form —$(CH_2)_{n10}$—, wherein $n_{10}$ is 1, 2, 3, or 4;

Z' is selected from the group consisting of a bond; $SO_2$; SO; S; and C(O);

Y is selected from the group consisting of H; $C_1$-$C_4$ haloalkyl; $C_5$-$C_6$ heterocycloalkyl; $C_6$-$C_{10}$ aryl; OH; —$N(Y_1)(Y_2)$; $C_1$-$C_{10}$ alkyl optionally substituted with 1 thru 3 substituents which can be the same or different and are selected from the group consisting of halogen, hydroxy, alkoxy, thioalkoxy, and haloalkoxy; $C_3$-$C_8$ cycloalkyl optionally substituted with 1, 2, or 3 groups independently selected from $C_1$-$C_3$ alkyl, and halogen; alkoxy; aryl optionally substituted with halogen, alkyl, alkoxy, CN or $NO_2$; arylalkyl optionally substituted with halogen, alkyl, alkoxy, CN or $NO_2$; wherein $Y_1$ and $Y_2$ are the same or different and are H; $C_1$-$C_{10}$ alkyl optionally substituted with 1, 2, or 3 substituents selected from the group consisting of halogen, $C_1$-$C_4$ alkoxy, $C_3$-$C_8$ cycloalkyl, and OH; $C_2$-$C_6$ alkenyl; $C_2$-$C_6$ alkanoyl; phenyl; —$SO_2$—$C_1$-$C_4$ alkyl; phenyl $C_1$-$C_4$ alkyl; or $C_3$-$C_8$ cycloalkyl $C_1$-$C_4$ alkyl; or $Y_1$, $Y_2$ and the nitrogen to which they are attached form a ring selected from the group consisting of piperazinyl, piperidinyl, morpholinyl, and pyrolidinyl, wherein each ring is optionally substituted with 1, 2, 3, or 4 groups that are independently $C_1$-$C_6$ alkyl, $C_1$-$C_6$ alkoxy, $C_1$-$C_6$ alkoxy $C_1$-$C_6$ alkyl, or halogen.

In still another alternative embodiment, $R_N$ is

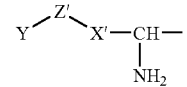

wherein

X' is $C_1$-$C_4$ alkylidenyl optionally substituted with 1, 2, or 3 methyl groups; or —$NR_{4-6}$—, where $R_{4-6}$ is —H or $C_1$-$C_6$ alkyl; or $R_4$ and $R_{4-6}$ combine to form —$(CH_2)_{n10}$—, where $R_4$ and $R_{4-6}$ are as defined above, wherein $n_{10}$ is 1, 2, 3, or 4;

Z' is selected from a bond; $SO_2$; SO; S; and C(O);

Y is selected from H; $C_1$-$C_4$ haloalkyl; $C_5$-$C_6$ heterocycloalkyl containing at least one N, O, or S; phenyl; OH; —$N(Y_1)(Y_2)$; $C_1$-$C_{10}$ alkyl optionally substituted with 1 thru 3 substituents which can be the same or different and are selected from halogen, hydroxy, alkoxy, thioalkoxy, and haloalkoxy; $C_3$-$C_8$ cycloalkyl optionally substituted with 1, 2, or 3 groups independently selected from $C_1$-$C_3$ alkyl, and halogen; alkoxy; phenyl optionally substituted with halogen, $C_1$-$C_4$ alkyl, $C_1$-$C_4$ alkoxy, CN or $NO_2$; phenyl $C_1$-$C_4$ alkyl optionally substituted with halogen, $C_1$-$C_4$ alkyl, $C_1$-$C_4$ alkoxy, CN or $NO_2$; wherein $Y_1$ and $Y_2$ are the same or different and are H; $C_1$-$C_{10}$ alkyl optionally substituted with 1, 2, or 3 substituents selected from the group consisting of halogen, $C_1$-$C_4$ alkoxy, $C_3$-$C_8$ cycloalkyl, and OH; $C_2$-$C_6$ alkenyl; $C_2$-$C_6$ alkanoyl; phenyl; —$SO_2$—$C_1$-$C_4$ alkyl; phenyl $C_1$-$C_4$ alkyl; and $C_3$-$C_8$ cycloalkyl $C_1$-$C_4$ alkyl; or —$N(Y_1)(Y_2)$ forms a ring selected from piperazinyl, piperidinyl, morpholinyl, and pyrolidinyl, wherein each ring is optionally substituted with 1, 2, 3, or 4 groups that are independently $C_1$-$C_6$ alkyl, $C_1$-$C_6$ alkoxy, $C_1$-$C_6$ alkoxy $C_1$-$C_6$ alkyl, or halogen.

In another embodiment, $R_N$ is $R_{N-5}$ wherein $R_{N-5}$ is selected from the group consisting of $C_1$-$C_6$ alkyl, —$(CH_2)_{0-2}$-aryl, $C_2$-$C_6$ alkenyl containing one or two double bonds, $C_2$-$C_6$ alkynyl containing one or two triple bonds, $C_3$-$C_7$ cycloalkyl, and $(CH_2)_{0-2}$-heteroaryl.

In a preferred embodiment, $R_1$ is $(CH_2)_{n1}$—$(R_{1-aryl})$ where $n_1$ is zero or one and $R_{1-aryl}$ is phenyl optionally substituted with 1, 2, 3, or 4 groups independently selected from $C_1$-$C_6$ alkyl optionally substituted with 1, 2, or 3 substituents selected from the group consisting of $C_1$-$C_3$ alkyl, halogen, —OH, —SH, —$NR_{1-a}R_{1-b}$, —C≡N, —$CF_3$, and $C_1$-$C_3$ alkoxy; halogen; $C_1$-$C_6$ alkoxy; —$NR_{N-2}R_{N-3}$; and OH; wherein $R_{1-a}$ and $R_{1-b}$ are —H or $C_1$-$C_6$ alkyl;

$R_{N-2}$ and $R_{N-3}$ at each occurrence are independently selected from the group consisting of —$C_1$-$C_8$ alkyl optionally substituted with 1, 2, or 3 groups independently selected from the group consisting of —OH, —$NH_2$, phenyl and halogen; —$C_3$-$C_8$ cycloalkyl; —$(C_1$-$C_2$ alkyl)-$(C_3$-$C_8$ cycloalkyl); —$(C_1$-$C_6$ alkyl)-O—$(C_1$-$C_3$ alkyl); —$C_2$-$C_6$ alkenyl; —$C_2$-$C_6$ alkynyl; —$C_1$-$C_6$ alkyl chain with one double bond and one triple bond; aryl; heteroaryl; heterocycloalkyl; or $R_{N-2}$, $R_{N-3}$ and the nitrogen to which they are attached form a 5, 6, or 7 membered heterocycloalkyl or heteroaryl group, wherein said heterocycloalkyl or heteroaryl group is optionally fused to a benzene, pyridine, or pyrimidine ring, and said groups are unsubstituted or substituted with 1, 2, 3, 4, or 5 groups that at each occurrence are independently $C_1$-$C_6$ alkyl, $C_1$-$C_6$ alkoxy, halogen, halo $C_1$-$C_6$ alkyl, halo $C_1$-$C_6$ alkoxy, —CN, —$NO_2$, —$NH_2$, NH($C_1$-$C_6$ alkyl), N($C_1$-$C_6$ alkyl) ($C_1$-$C_6$ alkyl), —OH, —C(O)$NH_2$, —C(O)NH ($C_1$-$C_6$ alkyl), —C(O)N($C_1$-$C_6$ alkyl) ($C_1$-$C_6$ alkyl), $C_1$-$C_6$ alkoxy $C_1$-$C_6$ alkyl, $C_1$-$C_6$ thioalkoxy, and $C_1$-$C_6$ thioalkoxy $C_1$-$C_6$ alkyl.

In another preferred aspect, $R_1$ is aryl, heteroaryl, heterocyclyl, —$C_1$-$C_6$ alkyl-aryl, —$C_1$-$C_6$ alkyl-heteroaryl, or —$C_1$-$C_6$ alkyl-heterocyclyl, where the ring portions of each are optionally substituted with 1, 2, 3, or 4 groups independently selected from halogen, —OH, —SH, —C≡N, —$NO_2$, —$NR_{105}R'_{105}$, —$CO_2R$, —N(R)COR', or —N(R)$SO_2R'$ (where $R_{105}$, $R'_{105}$, R and R' are as defined above), —C(═O)—($C_1$-$C_4$) alkyl, —$SO_2$-amino, —$SO_2$-mono or dialkylamino, —C(═O)-amino, —C(═O)-mono or dialkylamino, —$SO_2$—($C_1$-$C_4$) alkyl, or $C_1$-$C_6$ alkoxy optionally substituted with 1, 2, or 3 groups which are independently selected from halogen, or $C_3$-$C_7$ cycloalkyl optionally substituted with 1, 2, or 3 groups independently selected from halogen, —OH, —SH, —C≡N, —$CF_3$, $C_1$-$C_3$ alkoxy, amino, —$C_1$-$C_6$ alkyl and mono- or dialkylamino, or $C_1$-$C_{10}$ alkyl optionally substituted with 1, 2, or 3 groups independently selected from halogen, —OH, —SH, —C≡N, —$CF_3$, —$C_1$-$C_3$ alkoxy, amino, mono- or dialkylamino and —$C_1$-$C_3$ alkyl, or $C_2$-$C_{10}$ alkenyl or $C_2$-$C_{10}$ alkynyl each of which is optionally substituted with 1, 2, or 3 groups independently selected from halogen, —OH, —SH, —C≡N, —$CF_3$, $C_1$-$C_3$ alkoxy, amino, $C_1$-$C_6$ alkyl and mono- or dialkylamino; and the heterocyclyl group is optionally further substituted with oxo.

Preferred compounds of formula I also include those wherein $R_1$ is

—$C_1$-$C_6$ alkyl-aryl, —$C_1$-$C_6$ alkyl-heteroaryl, or —$C_1$-$C_6$ alkyl-heterocyclyl, where the ring portions of each are optionally substituted with 1, 2, 3, or 4 groups independently selected from halogen, —OH, —SH, —C≡N, —$NO_2$, —$NR_{105}R'_{105}$, —$CO_2R$, —N(R) COR', or —N(R)$SO_2R'$ (where $R_{105}$, $R'_{105}$, R and R' are as defined above), —C(═O)—($C_1$-$C_4$) alkyl, —$SO_2$-amino, —$SO_2$-mono or dialkylamino, —C(═O)-amino, —C(═O)-mono or dialkylamino, —$SO_2$—($C_1$-$C_4$) alkyl, or $C_1$-$C_6$ alkoxy optionally substituted with 1, 2, or 3 groups which are independently selected from halogen, or $C_3$-$C_7$ cycloalkyl optionally substituted with 1, 2, or 3 groups independently selected from halogen, —OH, —SH, —C≡N, —$CF_3$, $C_1$-$C_3$ alkoxy, amino, —$C_1$-$C_6$ alkyl and mono- or dialkylamino, or $C_1$-$C_{10}$ alkyl optionally substituted with 1, 2, or 3 groups independently selected from halogen, —OH, —SH, —C≡N, —$CF_3$, —$C_1$-$C_3$ alkoxy, amino, mono- or dialkylamino and —$C_1$-$C_3$ alkyl, or $C_2$-$C_{10}$ alkenyl or $C_2$-$C_{10}$ alkynyl each of which is optionally substituted with 1, 2, or 3 groups independently selected from halogen, —OH, —SH, —C≡N, —$CF_3$, $C_1$-$C_3$ alkoxy, amino, $C_1$-$C_6$ alkyl and mono- or dialkylamino; and the heterocyclyl group is optionally further substituted with oxo.

Preferred compounds of formula I further include those wherein $R_1$ is

—$(CH_2)$-aryl, —$(CH_2)$-heteroaryl, or —$(CH_2)$-heterocyclyl, where the ring portions of each are optionally substituted with 1, 2, 3, or 4 groups independently selected from halogen, —OH, —SH, —C≡N, —$NO_2$, —$NR_{105}R'_{105}$, —$CO_2R$, —N(R)COR', or —N(R)$SO_2R'$ (where $R_{105}$, $R'_{105}$, R and R' are as defined above), —C(═O)—($C_1$-$C_4$) alkyl, —$SO_2$-amino, —$SO_2$-mono or dialkylamino, —C(═O)-amino, —C(═O)-mono or dialkylamino, —$SO_2$—($C_1$-$C_4$) alkyl, or $C_1$-$C_6$ alkoxy optionally substituted with 1, 2, or 3 groups which are independently selected from halogen, or $C_3$-$C_7$ cycloalkyl optionally substituted with 1, 2, or 3 groups independently selected from halogen, —OH, —SH, —C≡N, —$CF_3$, $C_1$-$C_3$ alkoxy, amino, —$C_1$-$C_6$ alkyl and mono- or dialkylamino, or $C_1$-$C_{10}$ alkyl optionally substituted with 1, 2, or 3 groups independently selected from halogen, —OH, —SH, —C≡N, —$CF_3$, —$C_1$-$C_3$ alkoxy, amino, mono- or dialkylamino and —$C_1$-$C_3$ alkyl, or $C_2$-$C_{10}$ alkenyl or $C_2$-$C_{10}$ alkynyl each of which is optionally substituted with 1, 2, or 3 groups independently selected from halogen, —OH, —SH, —C≡N, —$CF_3$, $C_1$-$C_3$ alkoxy, amino, $C_1$-$C_6$ alkyl and mono- or dialkylamino; and the heterocyclyl group is optionally further substituted with oxo.

Preferred compounds of formula I also include those wherein $R_1$ is

—$CH_2$-phenyl or —$CH_2$-pyridinyl where the ring portions of each are optionally substituted with 1, 2, 3, or 4 groups independently selected from halogen, $C_1$-$C_4$ alkoxy, hydroxy, —$NO_2$, and $C_1$-$C_4$ alkyl optionally substituted with 1, 2, or 3 substituents independently selected from halogen, OH, SH, NH$_2$, NH(C$_1$-C$_6$ alkyl), N—(C$_1$-C$_6$ alkyl)(C$_1$-C$_6$ alkyl), C≡N, CF$_3$.

Preferred compounds of formula I further include those wherein R$_1$ is —CH$_2$-phenyl or —CH$_2$-pyridinyl where the phenyl or pyridinyl rings are each optionally substituted with 1 or 2 groups independently selected from halogen, C$_1$-C$_2$ alkyl, C$_1$-C$_2$ alkoxy, hydroxy, —CF$_3$, and —NO$_2$.

Preferred compounds of formula I include those wherein R$_1$ is —CH$_2$-phenyl where the phenyl ring is optionally substituted with 2 groups independently selected from halogen, C$_1$-C$_2$ alkyl, C$_1$-C$_2$ alkoxy, hydroxy, and —NO$_2$.

Preferred compounds of formula I also include those wherein R$_1$ is benzyl, or 3,5-difluorobenzyl.

In a preferred aspect, the invention is directed to compounds of Formula IA,

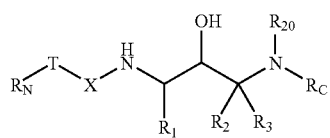

IA or pharmaceutically acceptable salts or esters thereof wherein

R$_N$, T, X, R$_{20}$, R$_1$, R$_2$, and R$_3$ are as defined above for Formula I;

R$_c$ is selected from —(CH$_2$)$_{0-3}$—(C$_3$-C$_8$) cycloalkyl wherein the cycloalkyl is optionally substituted with 1, 2, or 3 groups independently selected from —R$_{205}$; and —CO$_2$—(C$_1$-C$_4$ alkyl); —(CR$_{245}$R$_{250}$)$_{0-4}$-aryl; —(CR$_{245}$R$_{250}$)$_{0-4}$-heteroaryl; —(CR$_{245}$R$_{250}$)$_{0-4}$-heterocycloalkyl; —(CR$_{245}$R$_{250}$)$_{0-4}$-aryl-heteroaryl; —(CR$_{245}$R$_{250}$)$_{0-4}$-aryl-heterocycloalkyl; —(CR$_{245}$R$_{250}$)$_{0-4}$-aryl-aryl; —(CR$_{245}$R$_{250}$)$_{0-4}$-heteroaryl-aryl; —(CR$_{245}$R$_{250}$)$_{0-4}$-heteroaryl-heterocycloalkyl; —(CR$_{245}$R$_{250}$)$_{0-4}$-heteroaryl-heteroaryl; —CHR$_{245}$-CHR$_{250}$-aryl; —(CR$_{245}$R$_{250}$)$_{0-4}$-heterocycloalkyl-heteroaryl; —(CR$_{245}$R$_{250}$)$_{0-4}$-heterocycloalkyl-heterocycloalkyl; —(CR$_{245}$R$_{250}$)$_{0-4}$-heterocycloalkyl-aryl; a monocyclic or bicyclic ring of 5, 6, 7 8, 9, or 10 carbons fused to 1 or 2 aryl (preferably phenyl), heteroaryl (preferably pyridyl, imidazolyl, thienyl, thiazolyl, or pyrimidyl), or heterocycloalkyl (preferably piperidinyl or piperazinyl) groups;

wherein 1, 2 or 3 carbons of the monocyclic or bicyclic ring are optionally replaced with —NH—, —N(CO)$_{0-1}$R$_{215}$—, —N(CO)$_{0-1}$R$_{220}$—, —O—, or —S(=O)$_{0-2}$—, and wherein the monocyclic or bicyclic ring is optionally substituted with 1, 2 or 3 groups that are independently —R$_{205}$, —R$_{245}$, —R$_{250}$ or =O;

and —C$_2$-C$_6$ alkenyl optionally substituted with 1, 2, or 3 R$_{205}$ groups;

wherein each aryl or heteroaryl group attached directly or indirectly to the —(CR$_{245}$R$_{250}$)$_{0-4}$ group is optionally substituted with 1, 2, 3 or 4 R$_{200}$ groups;

wherein each heterocycloalkyl attached directly or indirectly to the —(CR$_{245}$R$_{250}$)$_{0-4}$ group is optionally substituted with 1, 2, 3, or 4 R$_{210}$;

R$_{200}$ at each occurrence is independently selected from
—C$_1$-C$_6$ alkyl optionally substituted with 1, 2, or 3 R$_{205}$ groups; —OH; —NO$_2$; -halogen; —C≡N; —(CH$_2$)$_{0-4}$—CO—NR$_{220}$R$_{225}$; —(CH$_2$)$_{0-4}$—CO—(C$_1$-C$_8$ alkyl); —(CH$_2$)$_{0-4}$—CO—(C$_2$-C$_8$ alkenyl); —(CH$_2$)$_{0-4}$—CO—(C$_2$-C$_8$ alkynyl); —(CH$_2$)$_{0-4}$—CO—(C$_3$-C$_7$ cycloalkyl); —(CH$_2$)$_{0-4}$—(CO)$_{0-1}$-aryl (preferably phenyl); —(CH$_2$)$_{0-4}$—(CO)$_{0-1}$-heteroaryl (preferably pyridyl, pyrimidyl, furanyl, imidazolyl, thienyl, oxazolyl, thiazolyl, or pyrazinyl); —(CH$_2$)$_{0-4}$—(CO)$_{0-1}$-heterocycloalkyl (preferably imidazolidinyl, piperazinyl, pyrrolidinyl, piperidinyl, or tetrahydropyranyl); —(CH$_2$)$_{0-4}$—CO$_2$R$_{215}$; —(CH$_2$)$_{0-4}$—SO$_2$—NR$_{220}$R$_{225}$; —(CH$_2$)$_{0-4}$—S(O)$_{0-2}$—(C$_1$-C$_8$ alkyl); —(CH$_2$)$_{0-4}$—S(O)$_{0-2}$—(C$_3$-C$_7$ cycloalkyl); —(CH$_2$)$_{0-4}$—N(H or R$_{215}$)—CO$_2$R$_{215}$; —(CH$_2$)$_{0-4}$—N(H or R$_{215}$)—SO$_2$—R$_{220}$; —(CH$_2$)$_{0-4}$—N(H or R$_{215}$)—CO—N(R$_{215}$)$_2$; —(CH$_2$)$_{0-4}$—N—(—H or R$_{215}$)—CO—R$_{220}$; —(CH$_2$)$_{0-4}$—NR$_{220}$R$_{225}$; —(CH$_2$)$_{0-4}$—O—CO—(C$_1$-C$_6$ alkyl); —(CH$_2$)$_{0-4}$-O—(R$_{215}$); —(CH$_2$)$_{0-4}$—S—(R$_{215}$); —(CH$_2$)$_{0-4}$—O—(C$_1$-C$_6$ alkyl optionally substituted with 1, 2, 3, or 5 —F); —C$_2$-C$_6$ alkenyl optionally substituted with 1 or 2 R$_{205}$ groups; —C$_2$-C$_6$ alkynyl optionally substituted with 1 or 2 R$_{205}$ groups; adamantly, and —(CH$_2$)$_{0-4}$—C$_3$-C$_7$ cycloalkyl;

each aryl and heteroaryl group included within R$_{200}$ is optionally substituted with 1, 2, or 3 groups that are independently —R$_{205}$, —R$_{210}$ or —C$_1$-C$_6$ alkyl substituted with 1, 2, or 3 groups that are independently R$_{205}$ or R$_{210}$;

each heterocycloalkyl group included within R$_{200}$ is optionally substituted with 1, 2, or 3 groups that are independently R$_{210}$;

R$_{205}$ at each occurrence is independently selected from
—C$_1$-C$_6$ alkyl, —C$_2$-C$_6$ alkenyl, —C$_2$-C$_6$ alkynyl, —C$_1$-C$_6$ haloalkoxy, —(CH$_2$)$_{0-3}$(C$_3$-C$_7$ cycloalkyl), -halogen, —(CH$_2$)$_{0-6}$—OH, —O-phenyl, OH, SH, —(CH$_2$)$_{0-6}$—C≡N, —(CH$_2$)$_{0-6}$—C(=O)NR$_{235}$R$_{240}$, —CF$_3$, —C$_1$-C$_6$ alkoxy, C$_1$-C$_6$ alkoxycarbonyl, and —NR$_{235}$R$_{240}$;

R$_{210}$ at each occurrence is independently selected from
—C$_1$-C$_6$ alkyl optionally substituted with 1, 2, or 3 R$_{205}$ groups; —C$_2$-C$_6$ alkenyl optionally substituted with 1, 2, or 3 R$_{205}$ groups; C$_1$-C$_6$ alkanoyl; —SO$_2$—(C$_1$-C$_6$ alkyl); —C$_2$-C$_6$ alkynyl optionally substituted with 1, 2, or 3 R$_{205}$ groups; -halogen; —C$_1$-C$_6$ alkoxy; —C$_1$-C$_6$ haloalkoxy; —NR$_{220}$R$_{225}$; —OH; —C≡N; —C$_3$-C$_7$ cycloalkyl optionally substituted with 1, 2, or 3 R$_{205}$ groups; —CO—(C$_1$-C$_4$ alkyl); —SO$_2$—NR$_{235}$R$_{240}$; —CO—NR$_{235}$R$_{240}$; —SO$_2$—(C$_1$-C$_4$ alkyl); and =O;

R$_{215}$ at each occurrence is independently selected from
—C$_1$-C$_6$ alkyl, —(CH$_2$)$_{0-2}$-(aryl), —C$_2$-C$_6$ alkenyl, —C$_2$-C$_6$ alkynyl, —C$_3$-C$_7$ cycloalkyl, —(CH$_2$)$_{0-2}$-(heteroaryl), and —(CH$_2$)$_{0-2}$-(heterocycloalkyl); wherein the aryl group included within R$_{215}$ is optionally substituted with 1, 2, or 3 groups that are independently —R$_{205}$ or —R$_{210}$; wherein the heterocycloalkyl and heteroaryl groups included within R$_{215}$ are optionally substituted with 1, 2, or 3 R$_{210}$;

R$_{220}$ at each occurrence is independently H, —C$_1$-C$_6$ alkyl, —CHO, hydroxy C$_1$-C$_6$ alkyl, C$_1$-C$_6$ alkoxycarbonyl, -amino C$_1$-C$_6$ alkyl, —SO$_2$—C$_1$-C$_6$ alkyl, C$_1$-C$_6$ alkanoyl optionally substituted with up to three halogens, —C(O)NH$_2$, —C(O)NH(C$_1$-C$_6$ alkyl), —C(O)N(C$_1$-C$_6$ alkyl) (C$_1$-C$_6$ alkyl), -halo C$_1$-C$_6$ alkyl, —(CH$_2$)$_{0-2}$—(C$_3$-C$_7$ cycloalkyl), —(C$_1$-C$_6$ alkyl)-O—(C$_1$-C$_3$ alkyl), —C$_2$-C$_6$ alkenyl, —C$_2$-C$_6$ alkynyl, -aryl (preferably phenyl), -heteroaryl, or -heterocycloalkyl; wherein the aryl, heteroaryl and heterocycloalkyl groups included within $R_{220}$ and $R_{225}$ is optionally substituted with 1, 2, or 3 $R_{270}$ groups, $R_{270}$ at each occurrence is independently —$R_{205}$, —$C_1$-$C_6$ alkyl optionally substituted with 1, 2, or 3 $R_{205}$ groups; —$C_2$-$C_6$ alkenyl optionally substituted with 1, 2, or 3 $R_{205}$ groups; —$C_2$-$C_6$ alkynyl optionally substituted with 1, 2, or 3 $R_{205}$ groups; -phenyl; -halogen; —$C_1$-$C_6$ alkoxy; —$C_1$-$C_6$ haloalkoxy; —$NR_{235}R_{240}$; —OH; —C≡N; —$C_3$-$C_7$ cycloalkyl optionally substituted with 1, 2, or 3 $R_{205}$ groups; —CO—($C_1$-$C_4$ alkyl); —$SO_2$—$NR_{235}R_{240}$; —CO—$NR_{235}R_{240}$; —$SO_2$—($C_1$-$C_4$ alkyl); and =O;

$R_{235}$ and $R_{240}$ at each occurrence are independently —H, —$C_1$-$C_6$ alkyl, $C_2$-$C_6$ alkanoyl, —$SO_2$—($C_1$-$C_6$ alkyl), or -phenyl;

$R_{245}$ and $R_{250}$ at each occurrence are independently selected from H, —$(CH_2)_{0-4}CO_2C_1$-$C_4$ alkyl, —$(CH_2)_{0-4}C(=O)C_1$-$C_4$ alkyl, —$C_1$-$C_4$ alkyl, —$C_1$-$C_4$ hydroxyalkyl, —$C_1$-$C_4$ alkoxy, —$C_1$-$C_4$ haloalkoxy, —$(CH_2)_{0-4}$—$C_3$-$C_7$ cycloalkyl, —$C_2$-$C_6$ alkenyl, —$C_2$-$C_6$ alkynyl, —$(CH_2)_{0-4}$ aryl, —$(CH_2)_{0-4}$ heteroaryl, and —$(CH_2)_{0-4}$ heterocycloalkyl, or $R_{245}$ and $R_{250}$ are taken together with the carbon to which they are attached to form a monocycle or bicycle of 3, 4, 5, 6, 7 or 8 carbon atoms, where 1, 2, or 3 carbon atoms are optionally replaced by 1, 2, or 3 gropus that are independently —O—, —S—, —$SO_2$—, —C(O)—, —$NR_{220}$—, or —$NR_{220}R_{220}$— wherein both $R_{220}$ groups are alkyl; and wherein the ring is optionally substituted with 1, 2, 3, 4, 5, or 6 groups that are independently $C_1$-$C_4$ alkyl, $C_1$-$C_4$ alkoxy, hydroxyl, $NH_2$, NH($C_1$-$C_6$ alkyl), N($C_1$-$C_6$ alkyl) ($C_1$-$C_6$ alkyl), —NH—C(O)$C_1$-$C_5$ alkyl, —NH—$SO_2$—($C_1$-$C_6$ alkyl), or halogen;

wherein the aryl, heteroaryl or heterocycloalkyl groups included within $R_{245}$ and $R_{250}$ are optionally substituted with 1, 2, or 3 groups that are independenly halogen, $C_{1-6}$ alkyl, CN or OH.

In another aspect of Formula IA, $R_1$ is $C_1$-$C_{10}$ alkyl optionally substituted with 1 or 2 groups independently selected from halogen, —OH, =O, —CN, —$CF_3$, —$OCF_3$, —$C_3$-$C_7$ cycloalkyl, —$C_1$-$C_4$ alkoxy, amino, mono-dialkylamino, aryl, heteroaryl or heterocycloalkyl, wherein the aryl group is optionally substituted with 1 or 2 $R_{50}$ groups;

$R_{50}$ is halogen, OH, CN, —CO—($C_1$-$C_4$ alkyl), —$NR_7R_8$, $C_1$-$C_6$ alkyl, $C_2$-$C_6$ alkenyl, $C_2$-$C_6$ alkynyl, $C_1$-$C_6$ alkoxy, and $C_3$-$C_8$ cycloalkyl;

$R_7$ and $R_8$ are selected from H; —$C_1$-$C_4$ alkyl optionally substituted with 1, 2, or 3 groups selected from —OH, —$NH_2$ and halogen; —$C_3$-$C_6$ cycloalkyl; —($C_1$-$C_4$ alkyl)-O—($C_1$-$C_4$ alkyl); —$C_2$-$C_4$ alkenyl; and —$C_2$-$C_4$ alkynyl;

$R_C$ is selected from —$(CR_{245}R_{250})_{0-4}$-aryl; —$(CR_{245}R_{250})_{0-4}$-heteroaryl; —$(CR_{245}R_{250})_{0-4}$-heterocycloalkyl; where the aryl and heteroaryl groups attached to the —$(CR_{245}R_{250})_{0-4}$— group are optionally substituted with 1, 2, 3 or 4 $R_{200}$ groups; where the heterocycloalkyl group attached to the —$(CR_{245}R_{250})_{0-4}$ group is optionally substituted with 1, 2, 3, or 4 $R_{210}$ groups; and $R_{245}$, $R_{250}$, $R_{200}$, and $R_{210}$ are as defined above.

In another aspect of Formula IA, the invention provides compounds wherein $R_C$ is —$(CR_{245}R_{250})_{0-4}$-heterocycloalkyl (preferably piperidinyl, piperazinyl, pyrrolidinyl, 2-oxo-tetrahydroquinolinyl, 2-oxo-dihydro-1H-indolyl, or imidazolidinyl); where the heterocycloalkyl group attached to the —$(CR_{245}R_{250})_{0-4}$-group is optionally substituted with 1, 2, 3, or 4 $R_{210}$ groups, wherein $R_{245}$, $R_{250}$, and $R_{210}$ are as defined above.

In another aspect of Formula IA, the invention provides compounds wherein $R_1$ is $C_1$-$C_{10}$ alkyl optionally substituted with 1 or 2 aryl groups, which are optionally substituted with 1 or 2 $R_{50}$ groups, wherein each $R_{50}$ is independently halogen, OH, CN, —$NR_7R_8$ or $C_1$-$C_6$ alkyl, $R_7$ and $R_8$ are independently —H; —$C_1$-$C_4$ alkyl optionally substituted with 1 or 2 groups independently selected from —OH, —$NH_2$, and halogen; or —$C_3$-$C_6$ cycloalkyl; and $R_C$ is —$(CR_{245}R_{250})_{0-4}$-aryl (preferred aryl groups include phenyl and naphthyl, more preferably, phenyl) or —$(CR_{245}R_{250})_{0-4}$-heteroaryl (preferably the heteroaryl is pyridyl, pyrimidyl, quinolinyl, isoquinolinyl, more preferably pyridyl), where the aryl and heteroaryl groups are optionally substituted with 1 or 2 $R_{200}$ groups, where $R_{200}$ is as defined above.

Still more preferred compounds of formula IA, include those wherein $R_1$ is $C_1$-$C_{10}$ alkyl substituted with one aryl group, where the aryl (preferably phenyl or naphthyl, still more preferably phenyl) group is optionally substituted with 1 or 2 $R_{50}$ groups;

$R_C$ is —$(CR_{245}R_{250})_{0-4}$-aryl (preferred aryl groups include phenyl and naphthyl, more preferably, phenyl) or —$(CR_{245}R_{250})_{1-4}$-heteroaryl (preferably the heteroaryl is pyridyl, pyrimidyl, quinolinyl, isoquinolinyl, more preferably pyridyl), $R_{245}$ and $R_{250}$ are independently selected from H, —$(CH_2)_{0-4}CO_2C_1$-$C_4$ alkyl, —$(CH_2)_{0-4}CO_2H$, —$C_1$-$C_4$ alkyl, —($C_1$-$C_4$ alkyl)OH, or $R_{245}$, $R_{250}$ and the carbon to which they are attached form a monocycle or bicycle of 3, 4, 5, 6, 7 or 8 carbon atoms, where 1 or 2 carbon atoms are optionally replaced by —O—, —S—, —$SO_2$—, or —$NR_{220}$—, where $R_{220}$ is as defined above; and wherein the aryl and heteroaryl groups attached to the —$(CR_{245}R_{250})_{1-4}$— groups are optionally substituted with 1 or 2 $R_{200}$ groups.

In another aspect of Formula IA, the invention provides compounds wherein, $R_1$ is $C_1$-$C_{10}$ alkyl substituted with one aryl group (preferably phenyl or naphthyl), which is optionally substituted with 1 or 2 $R_{50}$ groups, wherein $R_{50}$ is independently halogen, OH, or $C_1$-$C_6$ alkyl;

$R_C$ is —$(CR_{245}R_{250})$-aryl (preferred aryl groups include phenyl and naphthyl, more preferably, phenyl) or —$(CR_{245}R_{250})$-heteroaryl (preferably the heteroaryl is pyridyl, pyrimidyl, quinolinyl, isoquinolinyl, more preferably pyridyl), wherein the aryl and heteroaryl groups attached to the —$(CR_{245}R_{250})_{1-4}$— groups are optionally substituted with 1 or 2 substitutents selected from —Cl, —Br, —I, —$C_1$-$C_3$ alkyl, —($C_1$-$C_3$ alkyl)OH, —CN, —C=CH, —C=C—$CH_2$—OH, —$CF_3$, -thienyl optionally substituted with a —C(=O)H group, -phenyl optionally substituted with 1 or 2 $C_1$-$C_3$ alkyl groups, —($C_1$-$C_3$ alkyl)OH group or —CO($C_1$-$C_3$ alkyl) group, -isoxazolyl optionally substituted with a $C_1$-$C_4$ alkyl group, or —($C_1$-$C_2$ alkyl)oxazolyl where the oxazole ring is optionally substituted with —$C_1$-$C_2$ alkyl group;

$R_{245}$ and $R_{250}$ at each occurance are independently —H, —$C_1$-$C_3$ alkyl, —($C_1$-$C_3$ alkyl)$CO_2$H, —($C_1$-$C_3$ alkyl)$CO_2$($C_1$-$C_3$ alkyl), or —($C_1$-$C_3$ alkyl)OH, or $R_{245}$ and $R_{250}$ are taken together with the carbon to which they are attached to form a monocycle or bicycle of 3, 4, 5, 6, 7 or 8 carbon atoms, where 1 or 2 carbon atoms is optionally replaced by —O—, —S—, —$SO_2$—, or —$NR_{220}$—, and $R_{220}$ is as defined above.

In other preferred compounds of Formula IA, X is $SO_2$, T is absent and $R_N$ is $C_1$-$C_8$ alkyl or phenyl, where phenyl is optionally substituted with 1-2 of halogen, $C_1$-$C_6$ alkyl, $C_1$-$C_6$ alkoxy, amino, mono- or di($C_1$-$C_6$)alkylamino, trifluoromethyl, hydoxy, cyano, or $C_3$-$C_7$ cycloalkyl($C_1$-$C_6$) alkyl. More preferably, $R_N$ Unless indicated otherwise, in the structures below, the various variables carry the definitions given for Formula IA.

In another aspect, preferred compounds of formula IA include compounds of formula II:

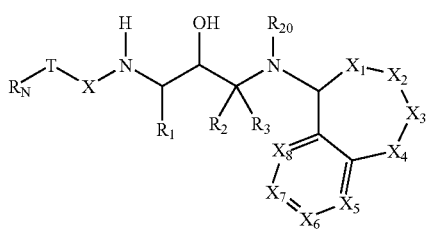

where $R_N$, X, T, $R_1$, $R_2$, $R_3$ and $R_{20}$ are definded above;

$X_1$ is $CH_2$, $CHR_{200}$, $C(R_{200})_2$, or —(C=O)—;

$X_2$, and $X_3$ are independently $CH_2$, $CHR_{200}$, $C(R_{200})_2$, O, C=O, S, $SO_2$, NH, or $NR_7$;

$X_4$ is a bond, $CH_2$, $CHR_{200}$, $C(R_{200})_2$ O, C=O, S, $SO_2$, NH, or $NR_7$;

wherein one of $X_2$, $X_3$ or $X_4$ is optionally replaced with O, C=O, S, $SO_2$, NH, or $NR_7$;

provided that when $X_1$ is —(C=O)—, $X_2$ is $CH_2$, $CHR_{200}$, $C(R_{200})_2$, O, NH or $NR_7$ and the $X_3$ group attached to $X_2$ is $CH_2$, $CHR_{200}$, $C(R_{200})_2$, or $SO_2$ when $X_2$ is NH or $NR_7$ and $X_4$ is $CH_2$, $CHR_{200}$, or $C(R_{200})$ 2 or a bond; or —$X_2$—$X_3$— is —(C=O)O—, —O(C=O), —(C=O)NH—, —NH(C=O)—, —(C=O)$NR_7$—, or —$NR_7$(C=O)—, with the proviso that $X_1$ is not —(C=O)— and with the proviso that $X_4$ is $CH_2$, $CHR_{200}$, or $C(R_{200})_2$ or a bond; or —$X_3$—$X_4$— is —(C=O)O—, —O(C=O) (C=O)NH—, —NH(C=O)—, —(C=O)$NR_7$—, or —$NR_7$(C=O)—, with the proviso that $X_2$ is $CH_2$, $CHR_{200}$, or $C(R_{200})_2$; or —$X_2$—$X_3$—$X_4$— is —(C=O)NH—$SO_2$— or —$SO_2$—NH (C=O)—, —(C=O)$NR_7$—$SO_2$— or —$SO_2$—$NR_7$(C=O)—, with the proviso that $X_1$ is not —(C=O)—; and $X_5$, $X_6$, $X_7$ and $X_8$ are CH or $CR_{200}$, where 1 or 2 of $X_5$, $X_6$, $X_7$ and $X_8$ is optionally replaced with N, and where $R_{200}$ and $R_7$ are as defined above.

In another aspect, preferred compounds of the invention include the compounds of formula III:

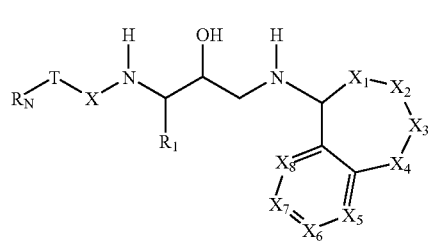

wherein $R_N$, X and T are as defined above;

$R_1$ is $C_1$-$C_{10}$ alkyl optionally substituted with 1 or 2 groups independently selected from halogen, —OH, =O, —CN, —$CF_3$, —$OCF_3$, —$C_3$-$C_7$ cycloalkyl, —$C_1$-$C_4$ alkoxy, amino, mono-dialkylamino, aryl optionally substituted with 1 or 2 $R_{50}$ groups, heteroaryl or heterocycloalkyl;

$R_{50}$ is halogen, OH, CN, —CO—($C_1$-$C_4$ alkyl), —$NR_7R_8$, $C_1$-$C_6$ alkyl, $C_2$-$C_6$ alkenyl, $C_2$-$C_6$ alkynyl, $C_1$-$C_6$ alkoxy or $C_3$-$C_8$ cycloalkyl; and $R_7$ and $R_8$ are selected from H; —$C_1$-$C_4$ alkyl optionally substituted with 1, 2, or 3 groups selected from —OH, —$NH_2$ and halogen; —$C_3$-$C_6$ cycloalkyl; —($C_1$-$C_4$ alkyl)-O—($C_1$-$C_4$ alkyl); —$C_2$-$C_4$ alkenyl; and —$C_2$-$C_4$ alkynyl;

$X_1$ is $CH_2$, $CHR_{200}$, $C(R_{200})_2$, or —(C=O)—;

$X_2$, and $X_3$ are independently $CH_2$, $CHR_{200}$, $C(R_{200})_2$, O, C=O, S, $SO_2$, NH, or $NR_7$;

$X_4$ is a bond, $CH_2$, $CHR_{200}$, $C(R_{200})_2$ O, C=O, S, $SO_2$, NH, or $NR_7$;

provided that when $X_1$ is —(C=O)—, $X_2$ is $CH_2$, $CHR_{200}$, $C(R_{200})_2$, O, NH or $NR_7$ and the $X_3$ group attached to $X_2$ is $CH_2$, $CHR_{200}$, $C(R_{200})_2$, or $SO_2$ when $X_2$ is NH or $NR_7$ and $X_4$ is $CH_2$, $CHR_{200}$, or $C(R_{200})$ 2 or a bond; or —$X_2$—$X_3$— is —(C=O)O—, —O(C=O)—, —(C=O)NH—, —NH(C=O)—, —(C=O)$NR_7$—, or —$NR_7$(C=O)—, with the proviso that $X_1$ is not —(C=O)— and with the proviso that $X_4$ is $CH_2$, $CHR_{200}$, or $C(R_{200})_2$ or a bond; or —$X_3$—$X_4$— is —(C=O)O—, —O(C=O)—, —(C=O)NH—, —NH(C=O)—, —(C=O)$NR_7$—, or —$NR_7$(C=O)—, with the proviso that $X_2$ is $CH_2$, $CHR_{200}$, or $C(R_{200})_2$; or —$X_2$—$X_3$—$X_4$— is —(C=O)NH—$SO_2$— or —$SO_2$—NH (C=O)—, —(C=O)$NR_7$—$SO_2$— or —$SO_2$—$NR_7$(C=O)—, with the proviso that $X_1$ is not —(C=O)—; and $X_5$, $X_6$, $X_7$ and $X_8$ are CH or $CR_{200}$, where 1 or 2 of $X_5$, $X_6$, $X_7$ and $X_8$ is optionally replaced with N, and where $R_{200}$ and $R_7$ are as defined above.

Preferred compounds of Formula III include those wherein $R_1$ is $C_1$-$C_{10}$ alkyl optionally substituted with 1 or 2 aryl (preferably phenyl or naphthyl) groups, which are optionally substituted with 1 or 2 $R_{50}$ groups, $R_{50}$ is independently halogen, OH, CN, —$NR_7R_8$ or $C_1$-$C_6$ alkyl;

R$_7$ and R$_8$ are independently H; —C$_1$-C$_4$ alkyl optionally substituted with 1 or 2 groups independently selected from —OH, —NH$_2$, and halogen; or —C$_3$-C$_6$ cycloalkyl; and X$_1$, X$_2$ or X$_3$ are independently CH$_2$ or CHR$_{200}$, where one of X$_2$ or X$_3$ is optionally replaced with O, C=O, SO$_2$, NH, NR$_7$, X$_4$ is a bond; and X$_5$, X$_6$, X$_7$ and X$_8$ are independently CH or CR$_{200}$, where one of X$_5$, X$_6$, X$_7$ or X$_8$ is optionally replaced with N, and R$_{200}$ is as defined above.

Even more preferred compounds of Formula III include those wherein

R$_1$ is C$_1$-C$_{10}$ alkyl substituted with one aryl group, where the aryl group is optionally substituted with 1 or 2 R$_{50}$ groups;

X$_1$, X$_2$ and X$_3$ are independently CH$_2$, CHR$_{200}$, or C(R$_{200}$)$_2$, where one of X$_2$ or X$_3$ is optionally replaced with O, NH or NR$_7$, and where X$_4$ is a bond; and X$_5$, X$_6$, X$_7$ and X$_8$ are independently CH or CR$_{200}$, where one of X$_5$, X$_6$, X$_7$ or X$_8$ is optionally replaced with N, where R$_{50}$, R$_{200}$ and R$_7$ are as defined above.

Still more preferred compounds of formula III include those wherein

R$_1$ is C$_1$-C$_{10}$ alkyl substituted with one aryl group (preferably phenyl or naphthyl, more preferably phenyl), where the aryl group is optionally substituted with 1 or 2 R$_{50}$ groups, wherein R$_{50}$ is independently halogen, OH, or C$_1$-C$_6$ alkyl;

X$_1$, X$_2$ and X$_3$ are independently CH$_2$ or CHR$_{200}$, where one of X$_2$ or X$_3$ is optionally replaced with O, NH or NR$_7$;

X$_4$ is a bond;

X$_5$, X$_6$, X$_7$ and X$_8$ are independently CH or CR$_{200}$, where one of X$_5$, X$_6$, X$_7$ and X$_8$ is optionally replaced with N; and R$_{200}$ is —C$_{1-4}$ alkyl, -halogen; —O—C$_{1-3}$ alkyl; -pyrrolyl or —(CH$_2$)$_{13}$—N(R$_7$)$_2$, where R$_7$ is as defined above.

Other preferred compounds of the invention are those of formula IV:

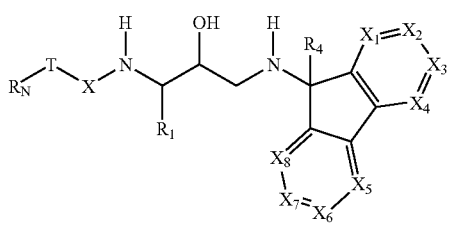

IV and pharmaceutically acceptable salts thereof, wherein

T, X and R$_N$ are as defined above;

R$_1$ is C$_1$-C$_{10}$ alkyl optionally substituted with 1 or 2 groups independently selected from halogen, —OH, =O, —CN, —CF$_3$, —OCF$_3$, —C$_3$-C$_7$ cycloalkyl, —C$_1$-C$_4$ alkoxy, amino, mono-dialkylamino, aryl optionally substituted with 1 or 2 R$_{50}$ groups, heteroaryl or heterocycloalkyl;

R$_{50}$ is halogen, OH, CN, —CO—(C$_1$-C$_4$ alkyl), —NR$_7$R$_8$, C$_1$-C$_6$ alkyl, C$_2$-C$_6$ alkenyl, C$_2$-C$_6$ alkynyl, C$_1$-C$_6$ alkoxy and C$_3$-C$_8$ cycloalkyl;

R$_7$ and R$_8$ are selected from H; —C$_1$-C$_4$ alkyl optionally substituted with 1, 2, or 3 groups selected from —OH, —NH$_2$ and halogen; —C$_3$-C$_6$ cycloalkyl; —(C$_1$-C$_4$ alkyl)-O—(C$_1$-C$_4$ alkyl); —C$_2$-C$_4$ alkenyl; and —C$_2$-C$_4$ alkynyl;

X$_1$—X$_8$ are independently CH or CR$_{200}$, where 1, 2, 3 or 4 of X$_1$-X$_8$ are optionally replaced with N (more preferably, 1, 2, or 3 are replaced with N);

where R$_{200}$ is as defineded above.

Preferred compounds of formula IV include those where

R$_1$ is C$_1$-C$_{10}$ alkyl optionally substituted with 1 or 2 aryl groups, where each aryl group is optionally substituted with 1 or 2 R$_{50}$ groups, R$_{50}$ is independently halogen, OH, CN, —NR$_7$R$_8$ or C$_1$-C$_6$ alkyl, R$_7$ and R$_8$ are independently H; —C$_1$-C$_4$ alkyl optionally substituted with 1 or 2 groups independently selected from —OH, —NH$_2$, and halogen; or —C$_3$-C$_6$ cycloalkyl; and X$_1$-X$_8$ are independently CH or CR$_{200}$, where one or two of X$_1$-X$_8$ is optionally replaced with N, and R$_{50}$ and R$_{200}$ are as defined above.

Other preferred compounds of formula IV include those where

R$_1$ is C$_1$-C$_{10}$ alkyl substituted with one aryl group, where the aryl group (preferably phenyl) is optionally substituted with 1 or 2 R$_{50}$ groups, R$_{50}$ is independently selected from halogen, OH, or C$_1$-C$_6$ alkyl;

X$_1$-X$_8$ are independently CH or CR$_{200}$, where one of X$_1$-X$_8$ is optionally replaced with N.

Still other Preferred compounds of formula IV include those where

R$_{200}$ is —C$_1$-C$_5$ alkyl, —C$_2$-C$_5$ alkenyl, —C$_3$-C$_6$ cycloalkyl, halogen, —CF$_3$, —O—C$_1$-C$_3$ alkyl, —(C$_1$-C$_3$ alkyl)-O—(C$_1$-C$_3$ alkyl), pyrrolyl, or —(CH$_2$)$_{1-3}$—N(R$_7$)$_2$.

Other preferred compounds of the invention include compounds of formula V:

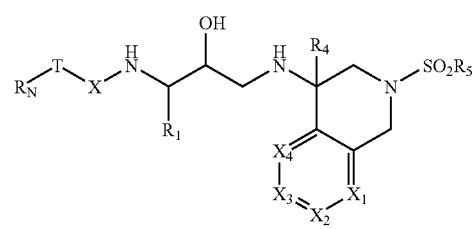

V and pharmaceutically acceptable salts thereof, wherein

T and R$_N$ are as defined above;

R$_1$ is C$_1$-C$_{10}$ alkyl optionally substituted with 1 or 2 groups independently selected from halogen, —OH, =O, —CN, —CF$_3$, —OCF$_3$, —C$_3$-C$_7$ cycloalkyl, —C$_1$-C$_4$ alkoxy, amino, mono-dialkylamino, aryl, heteroaryl and heterocycloalkyl, wherein the aryl, heterocycloalkyl and heteroaryl groups are optionally substituted with 1 or 2 R$_{50}$ groups, wherein the heterocycloalkyl group is optionally further substituted with =O;

R$_{50}$ is halogen, OH, CN, —CO—(C$_1$-C$_4$ alkyl), —NR$_7$R$_8$, C$_1$-C$_6$ alkyl, C$_2$-C$_6$ alkenyl, C$_2$-C$_6$ alkynyl, C$_1$-C$_6$ alkoxy and C$_3$-C$_8$ cycloalkyl;

$R_7$ and $R_8$ are selected from H; —$C_1$-$C_4$ alkyl optionally substituted with 1, 2, or 3 groups selected from —OH, —$NH_2$ and halogen; —$C_3$-$C_6$ cycloalkyl; —($C_1$-$C_4$ alkyl)-O—($C_1$-$C_4$ alkyl); —$C_2$-$C_4$ alkenyl; and —$C_2$-$C_4$ alkynyl;

$R_4$ is H or —$C_1$-$C_4$ alkyl;

$R_5$ is —$C_1$-$C_4$ alkyl;

$X_1$-$X_4$ are independently CH or $CR_{200}$, where 1 or 2 of $X_1$—$X_4$ are optionally replaced with N; and where $R_{200}$ is as defined above.

Preferred compounds of formula V include those where $R_1$ is $C_1$-$C_{10}$ alkyl optionally substituted with 1 or 2 aryl groups, where each aryl group is optionally substituted with 1 or 2 $R_{50}$ groups, each $R_{50}$ is independently halogen, OH, CN, —$NR_7R_8$ or $C_1$-$C_6$ alkyl, $R_7$ and $R_8$ are independently H; —$C_1$-$C_4$ alkyl optionally substituted with 1 or 2 groups independently selected from —OH, —$NH_2$, and halogen; or —$C_3$-$C_6$ cycloalkyl; and $X_1$-$X_4$ are independently CH or $CR_{200}$, where one or two of $X_1$-$X_4$ is optionally replaced with N; and $R_{200}$ is as defined above.

Other preferred compounds of formula V include those where $R_1$ is $C_1$-$C_{10}$ alkyl substituted with one aryl group (preferably phenyl), where the aryl group is optionally substituted with 1 or 2 $R_{50}$ groups, $R_{50}$ is independently selected from halogen, OH, and $C_1$-$C_6$ alkyl;

$X_1$-$X_4$ are CH or $CR_{200}$, where one of $X_1$-$X_4$ is optionally replaced with N, and where $R_{50}$ and $R_{200}$ are as defined above.

Still other preferred compounds of formula V include those where $R_{200}$ is —$C_1$-$C_5$ alkyl, —$C_1$-$C_5$ alkenyl, —$C_3$-$C_6$ cycloalkyl, halogen, —$CF_3$, —O—$C_1$-$C_3$ alkyl, —($C_1$-$C_3$ alkyl)-O—$C_1$-$C_3$ alkyl), pyrrolyl, or —$(CH_2)_{1-3}$-$N(R_7)_2$.

Yet other preferred compounds of the invention include those of formula VI:

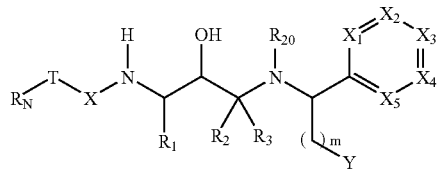

and pharmaceutically acceptable salts thereof, wherein

T, RN, $R_1$, $R_2$ and $R_3$ are as defined above;

m is 0 or an integer of 1-6;

Y is H, CN, OH, $C_1$-$C_6$ alkoxy, $CO_2H$, $CO_2R_{215}$, $NH_2$, aryl or heteroaryl; and $X_1$-$X_5$ are independently CH or $CR_{200}$, where 1, or 2 of $X_1$-$X_5$ are optionally replaced with N, and $R_{200}$ is defined as above.

Preferred compounds of formula VI include those where $R_2$, $R_3$ and $R_{15}$ are H;

X is —C(=O)—;

$R_1$ is $C_1$-$C_{10}$ alkyl optionally substituted with 1 or 2 groups independently selected from halogen, —OH, =O, —CN, —$CF_3$, —$OCF_3$, —$C_3$-$C_7$ cycloalkyl, —$C_1$-$C_4$ alkoxy, amino, mono-dialkylamino, aryl, heteroaryl or heterocycloalkyl, wherein the aryl, heterocycloalkyl and heteroaryl groups are optionally substituted with 1 or 2 $R_{50}$ groups, and wherein the heterocycloalkyl group is optionally further substituted with =O;

$R_{50}$ is halogen, OH, CN, —CO—($C_1$-$C_4$ alkyl), —$NR_7R_8$, $C_1$-$C_6$ alkyl, $C_2$-$C_6$ alkenyl, $C_2$-$C_6$ alkynyl, $C_1$-$C_6$ alkoxy or $C_3$-$C_8$ cycloalkyl;

$R_7$ and $R_8$ are independently H; —$C_1$-$C_4$ alkyl optionally substituted with 1, 2, or 3 groups selected from —OH, —$NH_2$ and halogen; —$C_3$-$C_6$ cycloalkyl; —($C_1$-$C_4$ alkyl)-O—($C_1$-$C_4$ alkyl); —$C_2$-$C_4$ alkenyl; or —$C_2$-$C_4$ alkynyl;

$X_1$-$X_5$ are independently CH or $CR_{200}$, where 1 or 2 of $X_1$-$X_5$ are optionally replaced with N; and Y and $R_{200}$ is as defined above.

Other preferred compounds of formula VI include those where $R_1$ is $C_1$-$C_{10}$ alkyl optionally substituted with 1 or 2 aryl groups, where each aryl group is optionally substituted with 1 or 2 $R_{50}$ groups, $R_{50}$ is independently halogen, OH, CN, —$NR_7R_8$ or $C_1$-$C_6$ alkyl, $R_7$ and $R_8$ are independently —H; —$C_1$-$C_4$ alkyl optionally substituted with 1 or 2 groups independently selected from —OH, —$NH_2$, and halogen; or —$C_3$-$C_6$ cycloalkyl;

$X_1$-$X_5$ are independently CH or $CR_{200}$, where one or two of $X_1$-$X_5$ is optionally replaced with N.

Still other preferred compounds of formula VI include those where $R_1$ is $C_1$-$C_{10}$ alkyl substituted with one aryl group, where the aryl group is optionally substituted with 1 or 2 $R_{50}$ groups, where $R_{50}$ is independently selected from halogen, OH, or $C_1$-$C_6$ alkyl;

wherein $X_1$-$X_5$ are independently CH or $CR_{200}$, where one of $X_1$-$X_5$ is optionally replaced with N, and where $R_{50}$ and $R_{200}$ are as defined above.

In yet another aspect, the invention provides compounds of formula VI, wherein $R_{200}$ is —$C_1$-$C_5$ alkyl, —$C_1$-$C_5$ alkenyl, —$C_3$-$C_6$ cycloalkyl, halogen, —$CF_3$, —O—$C_1$-$C_3$ alkyl, —($C_1$-$C_3$ alkyl)-O—($C_1$-$C_3$ alkyl), pyrrolyl, or —$(CH_2)_{13}$—$N(R_7)_2$, and where $R_7$ is as defined above.

Yet other preferred compounds of formula VI include those where $R_1$ is $C_1$-$C_{10}$ alkyl optionally substituted with 1 or 2 groups independently selected from halogen, —OH, =O, —$CF_3$, —$OCF_3$, —$C_{3-7}$ cycloalkyl, —$C_1$-$C_4$ alkoxy, amino and aryl, wherein the aryl group is optionally substituted with 1 or 2 $R_{50}$ groups; wherein $R_{50}$ is selected from halogen, OH, —CO—($C_1$-$C_4$ alkyl), —$NR_7R_8$, $C_1$-$C_6$ alkyl, $C_1$-$C_6$ alkoxy and $C_3$-$C_8$ cycloalkyl; and $R_7$ and $R_8$ are independently —H; —$C_1$-$C_4$ alkyl optionally substituted with 1, 2, or 3 groups independently selected from —OH, —NH$_2$, and halogen; —C$_3$-C$_6$ cycloalkyl; or —(C$_1$-C$_4$ alkyl)-O—(C$_1$-C$_4$ alkyl).

Other preferred compounds of formula IA include those of formula I-b, i.e., compounds of formula IA, wherein R$_C$ is (CR$_{245}$R$_{250}$)$_1$-aryl, where the aryl (preferably phenyl or naphthyl, more preferably phenyl) is optionally substituted with 1, 2, or 3 R$_{200}$ groups; and R$_{245}$ is H and R$_{250}$ is H or C$_1$-C$_6$ alkyl; or R$_{245}$ and R$_{250}$ are independently C$_1$-C$_3$ alkyl (preferably both are methyl); or CR$_{245}$R$_{250}$ represents a C$_3$-C$_7$ cycloalkyl group.

Preferred compounds of formula I-b include those of formula I-c, i.e., compounds of I-b wherein the (CR$_{245}$R$_{250}$)$_1$-aryl is (CR$_{245}$R$_{250}$)$_1$-phenyl where the phenyl is optionally substituted with 1, 2, or 3 R$_{200}$ groups.

Preferred compounds of formula I-c include those of formula I-d, i.e., compounds of I-c wherein the phenyl in (CR$_{245}$R$_{250}$)$_1$-phenyl is substituted with 1-3 independently selected R$_{200}$ groups, or 1 or 2 independently selected R$_{200}$ groups, and 1 heteroaryl group optionally substituted with 1 R$_{200}$ group or 1 phenyl group optionally substituted with 1 R$_{200}$ group. Other preferred comounds include those wherein the phenyl is substituted with a heterocycloalkyl group, which is optionally substituted with 1 or 2 R$_{200}$ groups and/or =O.

Preferred compounds of formula I-d include those of formula I-e, i.e., compounds wherein R$_{245}$ is hydrogen and R$_{250}$ is C$_1$-C$_3$ alkyl.

Preferred compounds of formula I-d include those of formula I-f, i.e., compounds of formula I-d wherein R$_{245}$ and R$_{250}$ are both hydrogen.

Preferred compounds of formula I-f include those of formula I-g, i.e., compounds of I-f wherein the phenyl in (CR$_{245}$R$_{250}$)$_1$-phenyl is substituted with (a) 1 R$_{200}$ group and 1 heteroaryl group optionally substituted with 1 R$_{200}$ group; or (b) 1 R$_{200}$ group and 1 phenyl group optionally substituted with 1 R$_{200}$ group; or (c) 1 R$_{200}$ group, and 1 heterocycloalkyl which is optionally substituted with one R$_{200}$ or =O.

Preferred compounds of formula I-g include those of formula I-h, i.e., compounds of I-g wherein R$_{200}$ is C$_1$-C$_6$ alkyl, C$_2$-C$_6$ alkenyl, C$_1$-C$_6$ alkoxy, hydroxy (C$_1$-C$_6$)alkyl, C$_1$-C$_6$ alkoxy(C$_1$-C$_6$)alkyl, heterocycloalkyl, heteroaryl, halogen, hydroxy, cyano, or —NR$_{220}$R$_{225}$, where R$_{220}$ and R$_{225}$ are independently hydrogen or alkyl.

Preferred compounds of formulas I-g or I-h, include those of formula I-i, i.e., compounds wherein R$_1$ is benzyl where the phenyl portion is optionally substituted with 1 or 2 groups independently selected from halogen, C$_1$-C$_2$ alkyl, C$_1$-C$_2$ alkoxy, —O-allyl, and hydroxy.

Preferred compounds of formula I-i include those of formula I-k, i.e., compounds of 1-i wherein the phenyl in (CR$_{245}$R$_{250}$)$_1$-phenyl is substituted with 1 R$_{200}$ group, and 1 heteroaryl group, wherein the heteroaryl is a 5-6 membered heteroaromatic ring containing 0 or 1-3 nitrogen atoms and 0 or 1 oxygen atoms provided that the ring contains at least one nitrogen or oxygen atom, and where the ring is optionally substituted with one or two groups which are independently C$_1$-C$_6$ alkyl, C$_1$-C$_6$ alkoxy, hydroxy(C$_1$-C$_6$)alkyl, hydroxy, halogen, cyano, nitro, trifluoromethyl, amino, mono(C$_1$-C$_6$)alkylamino, or di(C$_1$-C$_6$) alkylamino.

Other preferred compounds of formula I-i include those of formula I-k, i.e., compounds of 1-i wherein the phenyl in (CR$_{245}$R$_{250}$)$_1$-phenyl is substituted with 1 R$_{200}$ group, and 1 heterocycloalkyl group which is preferably piperazinyl, piperidinyl or pyrrolidinyl and where the group is optionally substituted with one or two groups which are independently C$_1$-C$_6$ alkyl, C$_1$-C$_6$ alkoxy, hydroxy(C$_1$-C$_6$) alkyl, hydroxy, halogen, cyano, nitro, trifluoromethyl, —SO$_2$—(C$_1$-C$_4$ alkyl), —C$_1$-C$_6$ alkanoyl, amino, mono (C$_1$-C$_6$)alkylamino, or di(C$_1$-C$_6$)alkylamino.

Preferred compounds of formula I-k include those of formula I-l, i.e., compounds wherein the heteroaryl is pyridinyl, pyrimidinyl, imidazolyl, pyrazolyl, furanyl, thiazolyl, or oxazolyl, each of which is optionally substituted with one or two groups which are independently C$_1$-C$_6$ alkyl, C$_1$-C$_6$ alkoxy, hydroxy(C$_1$-C$_6$) alkyl, hydroxy, halogen, cyano, nitro, trifluoromethyl, amino, mono(C$_1$-C$_6$)alkylamino, or di(C$_1$-C$_6$)alkylamino.

Preferred compounds of formula I-l include those of formula I-m, i.e., compounds wherein R$_{200}$ is C$_1$-C$_6$ alkyl, or C$_2$-C$_6$ alkenyl.

Other preferred compounds of formula I-d include those of formula I-n, i.e., compounds wherein CR$_{245}$R$_{250}$ represents a C$_3$-C$_7$ cycloalkyl group.

Preferred compounds of formula I-n include those of formula I-o, i.e., compounds of I-n wherein CR$_{245}$R$_{250}$ represents a C$_5$-C$_7$ cycloalkyl group.

Other preferred compounds of formula I-n, include those of formula I-p, i.e., compounds of I-n wherein CR$_{245}$R$_{250}$ represents a C$_3$-C$_6$ cycloalkyl group.

Preferred compounds of formula I-p include those of formula I-q, i.e., compounds of I-p wherein CR$_{245}$R$_{250}$ represents a C$_6$ cycloalkyl.

Preferred compounds of formula I-q include those of formula I-r, i.e., compounds of I-q wherein the phenyl in (CR$_{245}$R$_{250}$)$_1$-phenyl is substituted with 1 R$_{200}$ group; or 1 R$_{200}$ group and one heteroaryl group optionally substituted with one R$_{200}$ group or 1 R$_{200}$ group and one phenyl group optionally substituted with one R$_{200}$ group.

Preferred compounds of formula I-r include those of formula I-s, i.e., compounds wherein the phenyl in (CR$_{245}$R$_{250}$)$_1$-phenyl is substituted with 1 R$_{200}$ group.

Preferred compounds of formula I-s include those of formula I-t, i.e., compounds wherein R$_{200}$ is C$_1$-C$_6$ alkyl, C$_2$-C$_6$ alkenyl, C$_1$-C$_6$ alkoxy, hydroxy (C$_1$-C$_6$)alkyl, C$_1$-C$_6$ alkoxy(C$_1$-C$_6$)alkyl, halogen, hydroxy, cyano, or —NR$_{220}$R$_{225}$, where R$_{220}$ and R$_{225}$ are independently hydrogen or alkyl.

Preferred compounds of formula I-t include those of formula I-u, i.e., compounds wherein R$_1$ is benzyl where the phenyl portion of the benzyl group is optionally substituted with 1 or 2 groups independently selected from halogen, C$_1$-C$_2$ alkyl, C$_1$-C$_2$ alkoxy, —O-allyl, and hydroxy.

Preferred compounds of formula I-u include those of formula I-w, i.e., compounds of I-u wherein R$_{200}$ is C$_1$-C$_6$ alkyl or C$_2$-C$_6$ alkenyl.

Preferred compounds of formula I-w, include those of formula I-x, i.e., compounds wherein $R_1$ is benzyl, 3-fluorobenzyl or 3,5-difluorobenzyl.

Preferred compounds of formula I-w, include those of formula I-z, i.e., compounds wherein $R_{200}$ is $C_3$-$C_5$ alkyl.

Preferred compounds of formula I-m, include those of formula I-aa, i.e., compounds wherein $R_{200}$ is $C_3$-$C_5$ alkyl.

In another aspect, the invention provides compounds of formula I-bb, i.e., compounds according to any one of formulas I to I-aa, wherein $R_2$ is H, methyl, or hydroxymethyl and $R_3$ is H.

Other preferred compounds of formula I include those of formula I-cc, wherein $R_c$ is a monocyclic or bicyclic ring of 5, 6, 7 8, 9, or 10 carbons fused to 1 aryl (preferably phenyl), heteroaryl (preferably pyridyl, imidazolyl, thienyl, or pyrimidyl), or heterocycloalkyl (preferably piperidinyl or piperazinyl) groups;

wherein 1, 2 or 3 carbons of the monocyclic or bicyclic ring are optionally replaced with —NH—, —N(CO)$_{0-1}$R$_{215}$—, —N(CO)$_{0-1}$R$_{220}$—, —O—, or —S(=O)$_{0-2}$—, and wherein the monocyclic or bicyclic ring is optionally substituted with 1, 2 or 3 groups that are independently —R$_{205}$, —R$_{245}$, —R$_{250}$ or =O. More preferably, $R_c$ is as defined above and $R_1$ is $C_1$-$C_{10}$ alkyl substituted with one aryl group (preferably phenyl), where the aryl group is optionally substituted with 1 or 2 $R_{50}$ groups.

Other preferred compounds of formula I include those of formula I-dd, wherein $R_c$ is —CHR$_{245}$-CHR$_{250}$-phenyl; wherein the phenyl is optionally substituted with 1, 2, 3 or 4 $R_{200}$ groups; and $R_{245}$ and $R_{250}$ are taken together with the carbon to which they are attached to form a monocycle or bicycle of 5, 6, 7 or 8 carbon atoms, where 1, or 2 carbon atoms are optionally replaced by 1 or 2 groups that are independently —O—, —S—, —SO$_2$—, —C(O)—, or —NR$_{220}$—, and wherein the ring is optionally substituted with 1, 2, 3, 4, 5, or 6 groups that are independently $C_1$-$C_4$ alkyl, $C_1$-$C_4$ alkoxy, hydroxyl, NH$_2$, NH($C_1$-$C_6$ alkyl), N($C_1$-$C_6$ alkyl)($C_1$-$C_6$ alkyl), —NH—C(O)C$_1$-$C_5$ alkyl, —NH—SO$_2$—($C_1$-$C_6$ alkyl), or halogen; and $R_1$ is $C_1$-$C_{10}$ alkyl substituted with one aryl group (preferably phenyl), where the aryl group is optionally substituted with 1 or 2 $R_{50}$ groups.

Preferred compounds of formula I-dd include those of formula I-ee, i.e. compounds of formula I-dd, wherein $R_{245}$ and $R_{250}$ are taken together with the carbons to which they are attached to form a monocycle or bicycle of 5, 6, 7 or 8 carbon atoms, and wherein the ring is optionally substituted with 1, 2, 3, 4, 5, or 6 groups that are independently $C_1$-$C_4$ alkyl, $C_1$-$C_4$ alkoxy, hydroxyl, NH$_2$, NH($C_1$-$C_6$ alkyl), N($C_1$-$C_6$ alkyl)($C_1$-$C_6$ alkyl), —NH—C(O)C$_1$-$C_5$ alkyl, —NH—SO$_2$—($C_1$-$C_6$ alkyl), or halogen.

Preferred compounds of formula I-dd include those of formula I-ff, i.e. compounds of formula I-dd, wherein $R_{245}$ and $R_{250}$ are taken together with the carbons to which they are attached to form a monocycle or bicycle of 5, or 6, carbon atoms, and wherein the ring is optionally substituted with 1, 2, 3, 4, 5, or 6 groups that are independently $C_1$-$C_4$ alkyl, $C_1$-$C_4$ alkoxy, hydroxyl, NH$_2$, NH($C_1$-$C_6$ alkyl), N($C_1$-$C_6$ alkyl) ($C_1$-$C_6$ alkyl), —NH—C(O)C$_1$-$C_5$ alkyl, —NH—SO$_2$—($C_1$-$C_6$ alkyl), or halogen.

Preferred compounds of formula I include those of formula II-gg, i.e. compounds of formula I wherein $R_c$ is —(CR$_{245}$R$_{250}$)-heteroaryl (preferred heteroaryl groups include thienyl, pyridyl, pyrimidyl, quinolinyl, oxazolyl, and thiazolyl), wherein the heteroaryl group attached to the —(CR$_{245}$R$_{250}$)$_{1-4}$— group is optionally substituted with 1 or 2 substitutents selected from —Cl, —Br, —I, —$C_1$-$C_6$ alkyl, —($C_1$-$C_3$ alkyl)OH, —CN, —C=CH, —C=C—CH$_2$—OH, —CF$_3$, or -phenyl optionally substituted with 1 or 2 $C_1$-$C_3$ alkyl groups, —($C_1$-$C_3$ alkyl)OH group or —CO($C_1$-$C_3$ alkyl) group, wherein $R_{245}$ and $R_{250}$ at each occurance are independently —H, —$C_1$-$C_3$ alkyl, —($C_1$-$C_3$ alkyl)CO$_2$H, or —($C_1$-$C_3$ alkyl)OH, (in one aspect $R_{245}$ is H; in another aspect, $R_{245}$ and $R_{250}$ are H; in another aspect, $R_{245}$ and $R_{250}$ are both methyl) or $R_{245}$ and $R_{250}$ are taken together with the carbon to which they are attached to form a monocycle or bicycle of 3, 4, 5, 6, 7 or 8 carbon atoms (preferably 6 carbon atoms), where 1 or 2 carbon atoms is optionally replaced by —O—, —C(O)—, —S—, —SO$_2$—, or —NR$_{220}$—, and $R_{220}$ is as defined above.

In another aspect, the invention provides compounds of the formula VII:

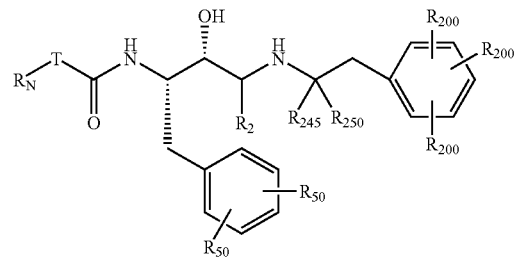

VII and pharmaceutically acceptable salts thereof, wherein $R_{245}$ and $R_{250}$ are taken together with the carbon to which they are attached to form a monocycle or bicycle of 3, 4, 5, 6, 7, or 8 carbon atoms, where 1, 2, or 3 CH$_2$ groups are optionally replaced by 1, 2, or 3 groups that are independently —O—, —S—, —SO$_2$—, —C(O)—, or —NR$_{220}$—; and wherein the ring is optionally substituted with 1, 2, 3, 4, 5, or 6 groups that are independently $C_1$-$C_4$ alkyl, $C_1$-$C_4$ alkoxy, =O, hydroxyl and halogen;

$R_2$, $R_{50}$, $R_{200}$, and $R_{220}$ are as defined for formula I.

Preferred compounds of formula VII include compounds of formula VII-a, i.e., compounds of formula VII wherein at least one of the $R_{50}$ groups is a halogen.

Preferred compounds of formula VII-a include compounds of formula VII-c, i.e., compounds of formula VII-a wherein at least one $R_{50}$ group is halogen. More preferably, the other $R_{50}$ group is H, OH or —O-allyl. In another aspect, both $R_{50}$ groups are halogen and more preferably, F or Cl. Still more preferably, both $R_{50}$ groups are F. Still more preferably, the $R_{50}$ groups are "meta" relative to each other, i.e., 1-3 to each other.

Preferred compounds according to any one of formulas VII, VII-a and VII-c include compounds of formula VII-d, i.e., compounds wherein $R_{245}$ and $R_{250}$ are taken together with the carbon to which they are attached to form a monocycle of 3, 4, 5, 6, or 7 carbon atoms (preferably 4, 5, or 6 carbon atoms, more preferably, 5 or 6 carbon atoms), wherein the ring is optionally substituted with 1, 2, 3, 4, 5, or 6 groups that are independently $C_1$-$C_4$ alkyl, $C_1$-$C_4$ alkoxy, hydroxyl, =O, and halogen. More preferably, the ring is optionally substituted with 1, 2, or 3 groups. Still more preferably, if the ring is substituted, one of the groups is =O.

Preferred compounds according to any one of formulas VII, VII-a, and VII-c include compounds of formula VII-e, i.e., compounds wherein $R_{245}$ and $R_{250}$ are taken together with the carbon to which they are attached to form a bicycle of 5, 6, 7, or 8 carbon atoms, where 1, carbon atom is optionally replaced by a group selected from —O—, —S—, —SO$_2$—, —C(O)—, and —NR$_{220}$—; and wherein the ring is optionally substituted with 1, 2, 3, 4, 5, or 6 groups that are independently $C_1$-$C_4$ alkyl, $C_1$-$C_4$ alkoxy, hydroxyl and halogen. Preferably the bicycle is bicyclo[3.1.0]hexyl, 6-aza-bicyclo[3.1.0]hexane wherein the nitrogen is optionally substituted with —C(O)CH$_3$ or CH$_3$, octahydro-cyclopenta[c]pyrrolyl, 5-oxo-octahydro-pentalenyl, or 5-hydroxy-octahydro-pentalenyl, each of which is optionally substituted with 1, 2, 3, 4, 5, or 6 groups that are independently $C_1$-$C_4$ alkyl, $C_1$-$C_4$ alkoxy, hydroxyl and halogen.

Preferred according to any one of formulas VII-c, VII-d and VII-e include compounds wherein one $R_{200}$ is imidazolyl, thiazolyl, oxazolyl, tetrazolyl, thienyl, furanyl, benzyl, piperidinonyl, or pyridyl, wherein each is optionally substituted with halogen, or $C_1$-$C_4$ alkyl. Also preferred are compounds wherein a second $R_{200}$ is $C_1$-$C_6$ alkyl (preferably $C_2$-$C_6$ alkyl, more preferably tert-butyl, neopentyl or isopropyl.)

Preferred compounds according to any one of formulas VII, VII-a, and VII-c, include compounds of formula VII-f, i.e., compounds wherein $R_{245}$ and $R_{250}$ are taken together with the carbon to which they are attached to form a monocycle of 3, 4, 5, 6, or 7 carbon atoms, where at least 1, but up to 3 carbon atoms are replaced by groups that are independently —O—, —S—, —SO$_2$—, —C(O)—, or —NR$_{220}$— (in one aspect, preferably —O—); and wherein the ring is optionally substituted with 1, 2, 3, 4, 5, or 6 groups that are independently $C_1$-$C_4$ alkyl, $C_1$-$C_4$ alkoxy, hydroxyl and halogen. Preferably the monocycle is tetrahydropyranyl, 2-oxo-tetrahydropyrimidinonyl, piperidinyl, 2-oxo(1,3)oxazinonyl, or cyclohexanonyl. Preferably, $R_{220}$ is H, —$C_1$-$C_6$ alkyl, —CHO, hydroxy $C_1$-$C_6$ alkyl, $C_1$-$C_6$ alkoxycarbonyl, -amino $C_1$-$C_6$ alkyl, —SO$_2$—$C_1$-$C_6$ alkyl, $C_1$-$C_6$ alkanoyl optionally substituted with up to three halogens, —C(O)NH$_2$, —C(O)NH($C_1$-$C_6$ alkyl), —C(O)N($C_1$-$C_6$ alkyl) ($C_1$-$C_6$ alkyl), -halo $C_1$-$C_6$ alkyl, or —(CH$_2$)$_{0-2}$—($C_3$-$C_7$ cycloalkyl). More preferably, $R_{220}$ is H, —$C_1$-$C_6$ alkyl, $C_1$-$C_6$ alkoxycarbonyl, —SO$_2$—$C_1$-$C_6$ alkyl, —C(O)CF$_3$, —C(O)NH$_2$, —C(O)NH ($C_1$-$C_6$ alkyl), or —C(O)N($C_1$-$C_6$ alkyl) ($C_1$-$C_6$ alkyl).

Preferred compounds according to any one of formulas VII-d or VII-e include compounds of formula VII-g, i.e., compounds wherein at least one $R_{200}$ is $C_1$-$C_6$ alkyl. More preferably, $R_{200}$ is $C_2$-$C_6$ alkyl. Still more preferably it is $C_3$-$C_6$ alkyl.

Preferred compounds according to any one of formulas VIIa-VIIg include compounds of formula VII-h, i.e., compounds wherein $R_c$ is of the formula:

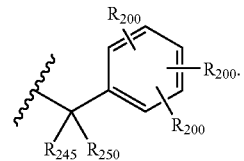

More preferably, $R_c$ is of the formula:

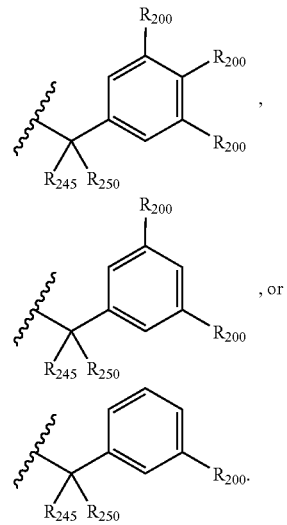

In another aspect, the invention provides compounds according to any one of formulas VII to VII-h wherein $R_2$ is H.

In another aspect, the invention provides compounds according to any one of formulas VII to VII-h wherein $R_2$ is $C_1$-$C_4$ alkyl or hydroxy $C_1$-$C_4$ alkyl.

In another aspect, the invention provides compounds of formula VIII:

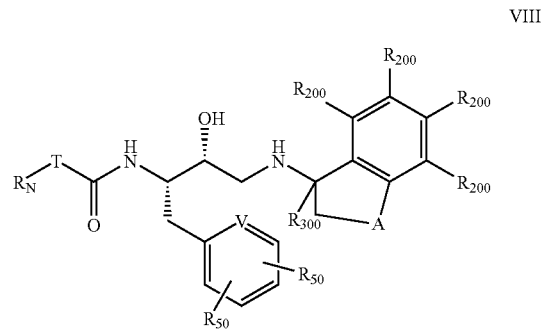

VIII wherein

A is —CH$_2$—CR$_{100}$R$_{101}$—, —CH$_2$—S—, —CH$_2$—S (O)—, —CH$_2$—S(O)$_2$—, —CH$_2$—NR$_{100}$—, —CH$_2$—C (O)—, —CH$_2$—O—, —O—CR$_{100}$R$_{101}$—, —SO$_2$—NR$_{100}$, or —C(O)—O—;

$R_{100}$ and $R_{101}$ are independently H, $C_1$-$C_6$ alkyl, phenyl, CO($C_1$-$C_6$ alkyl) or $SO_2C_1$-$C_6$ alkyl;

V is CH, $CR_{50}$, or N;

$R_{300}$ is H or $C_1$-$C_4$ alkyl (preferably the alkyl is methyl); and

Z, $R_{50}$ and $R_{200}$ are as defined for formula I.

Preferred compounds of formula VIII include compounds of formula VIII-a, i.e., compounds of formula VIII wherein at least one of the $R_{50}$ groups is a halogen. In another aspect, the other $R_{50}$ group is H, OH, or —O-allyl.

Preferred compounds of formula VIII-a, include compounds of formula VIII-b, i.e., compounds wherein T is NH, N-methyl N-ethyl, or oxygen.

Preferred compounds of formula VIII-b include compounds of formula VIII-c, i.e., compounds of formula VIII-b wherein both $R_{50}$ groups are halogen and more preferably, F or Cl. Still more preferably, both $R_{50}$ groups are F. In other preferred compounds, at least one $R_{50}$ is OH or —O-benzyl. More preferably, a second $R_{50}$ is present and it is a halogen (preferably F or Cl.)

Preferred compounds according to any one of formulas VIII, VIII-a, VIII-b, or VIII-c, include those of formula VIII-d, i.e., compounds wherein at least one $R_{200}$ is $C_1$-$C_6$ alkyl. In one aspect, $R_{200}$ is $C_3$-$C_6$ alkyl, preferably neopentyl, tert-butyl or isopropyl. In another aspect, $R_{200}$ is $C_1$-$C_4$ alkyl.

Preferred compounds of formual VIII-d include those wherein A is —$CH_2$—O— or —$CH_2$—$CH_2$—. Also preferred are compounds wherein A is —C(O)—O—, Also preferred are compounds wherein A is —$CH_2$—$NR_{100}$—. Also preferred are compounds wherein A is —$CH_2$—S—, —$CH_2$—S(O)—, or —$CH_2$—S(O)$_2$—.

Preferred compounds of formula VIII include compounds wherein one $R_{200}$ is $C_1$-$C_6$ alkyl, preferably $C_2$-$C_6$ alkyl, more preferably $C_3$-$C_5$ alkyl.

Also preferred are compounds wherein a second $R_{200}$ is present and it is imidazolyl, thiazolyl, oxazolyl, tetrazolyl, thienyl, furanyl, benzyl, or pyridyl, wherein each cyclic group is optionally substituted with —$R_{205}$, halogen, and/or $C_1$-$C_4$ alkyl. In another aspect, they are substituted with halogen, and/or $C_1$-$C_4$ alkyl. Also preferred are compounds wherein a second $R_{200}$ is $C_1$-$C_6$ alkyl. Also preferred are compounds wherein $R_{100}$ and $R_{101}$ are independently H or $C_1$-$C_6$ alkyl.

In another aspect, preferred compounds of formula VIII-d include those wherein $R_{300}$ is methyl. In another aspect, when $R_{300}$ is methyl, A is —$CH_2$—O— or —$CH_2$—$CH_2$—.

In another aspect, preferred compounds of formula I include compounds of formula A-I:

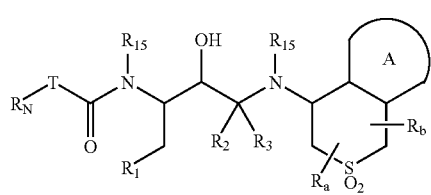

A-I and a pharmaceutically acceptable salt thereof, wherein the A ring is a heteroaryl group, selected from pyridinyl, pyrimidinyl, imidazolyl, oxazolyl, thiazolyl, furanyl, thienyl, pyrrolyl, wherein said heteroaryl groups are optionally substituted with one, two, three, or four $R_z$ and/or $R_d$ groups, wherein $R_z$ and $R_d$ at each occurrence are independently $C_1$-$C_6$ alkyl optionally substituted with one, two or three substituents selected from $C_1$-$C_3$ alkyl, halogen, OH, SH, C≡N, $CF_3$, $C_1$-$C_3$ alkoxy, and —$NR_5R_6$; or OH; $NO_2$; halogen; $CO_2H$; C≡N; —$(CH_2)_{0-4}$—CO—$NR_{21}R_{22}$ wherein $R_{21}$ and $R_{22}$ are the same or different and are selected from H; —$C_1$-$C_6$ alkyl optionally substituted with one substituent selected from OH and —$NH_2$; —$C_1$-$C_6$ alkyl optionally substituted with one to three groups that are independently —F, —Cl, —Br, or —I; —$C_3$-$C_7$ cycloalkyl; —($C_1$-$C_2$ alkyl)-($C_3$-$C_7$ cycloalkyl); —($C_1$-$C_6$ alkyl)-O—($C_1$-$C_3$ alkyl); —$C_2$-$C_6$ alkenyl; —$C_2$-$C_6$ alkynyl; —$C_1$-$C_6$ alkyl chain with one double bond and one triple bond; $R_{17}$; and $R_{18}$; or —$(CH_2)_{0-4}$—CO—($C_1$-$C_{12}$ alkyl); —$(CH_2)_{0-4}$—CO—($C_2$-$C_{12}$ alkenyl); —$(CH_2)_{0-4}$—CO—($C_2$-$C_{12}$ alkynyl); —$(CH_2)_{0-4}$—CO—($C_3$-$C_7$ cycloalkyl); —$(CH_2)_{0-4}$—CO—$R_{17}$; —$(CH_2)_{0-4}$—CO—$R_{18}$; —$(CH_2)_{0-4}$—CO—$R_{19}$; or —$(CH_2)_{0-4}$—CO—$R_{11}$ wherein $R_{17}$ at each occurrence is an aryl group selected from phenyl, 1-naphthyl, 2-naphthyl and indanyl, indenyl, dihydronaphthyl, or tetralinyl, wherein said aryl groups are optionally substituted with one, two, three, or four groups that are independently $C_1$-$C_6$ alkyl optionally substituted with one, two or three substituents selected from $C_1$-$C_3$ alkyl, F, Cl, Br, I, OH, SH, and —$NR_5R_6$, C≡N, $CF_3$, and $C_1$-$C_3$ alkoxy; or $C_2$-$C_6$ alkenyl or $C_2$-$C_6$ alkynyl each of which is optionally substituted with one, two or three substituents selected from F, Cl, OH, SH, C≡N, $CF_3$, $C_1$-$C_3$ alkoxy, and —$NR_5R_6$; or halogen; —$C_1$-$C_6$ alkoxy optionally substituted with one, two, or three F; —$NR_{21}R_{22}$; OH; C≡N; $C_3$-$C_7$ cycloalkyl, optionally substituted with one, two or three substituents selected from F, Cl, OH, SH, C≡N, $CF_3$, $C_1$-$C_3$ alkoxy, and —$NR_5R_6$; or —CO—($C_1$-$C_4$ alkyl); —$SO_2$—$NR_5R_6$; —CO—$NR_5R_6$; or —$SO_2$—($C_1$-$C_4$alkyl);

$R_{18}$ at each occurrence is a heteroaryl group selected from pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, wherein said heteroaryl group is optionally substituted with one, two, three, or four groups that are independently $C_1$-$C_6$ alkyl optionally substituted with one, two or three substituents selected from $C_1$-$C_3$ alkyl, F, Cl, Br, I, OH, SH, C≡N, $CF_3$, $C_1$-$C_3$ alkoxy, and —$NR_5R_6$; or $C_2$-$C_6$ alkenyl or $C_2$-$C_6$ alkynyl each of which is optionally substituted with one, two or three substituents selected from —F, —Cl, —OH, —SH, —C≡N, —$CF_3$, $C_1$-$C_3$ alkoxy, and —$NR_5R_6$; or halogen; —$C_1$-$C_6$ alkoxy optionally substituted with one, two, or three —F; —$NR_{21}R_{22}$; —OH; —C≡N; $C_3$-$C_7$ cycloalkyl optionally substituted with one, two or three substituents independently selected from F, Cl, OH, SH, C≡N, $CF_3$, $C_1$-$C_3$ alkoxy, and —$NR_5R_6$; —CO—($C_1$-$C_4$ alkyl); —$SO_2$—$NR_5R_6$; —CO—$NR_5R_6$; or —$SO_2$—($C_1$-$C_4$ alkyl);

$R_{19}$ at each occurrence is independently morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, or homothiomorpholinyl S-oxide; wherein said $R_{19}$ group is optionally substituted with one, two, three, or four groups that are independently $C_1$-$C_6$ alkyl optionally substituted with one, two or three substituents selected from $C_1$-$C_3$ alkyl, F, Cl, Br, I, OH, SH, C≡N, $CF_3$, $C_1$-$C_3$ alkoxy, and —$NR_5R_6$;

$C_2$-$C_6$ alkenyl or $C_2$-$C_6$ alkynyl, wherein each is optionally substituted with one, two or three substituents selected from F, Cl, OH, SH, C≡N, $CF_3$, $C_1$-$C_3$ alkoxy, and —$NR_5R_6$;

halogen; $C_1$-$C_6$ alkoxy; $C_1$-$C_6$ alkoxy optionally substituted with one, two, or three F; OH; C≡N; —$NR_{21}R_{22}$; $C_3$-$C_7$ cycloalkyl optionally substituted with one, two, or three substituents independently selected from F, Cl, OH, SH, C≡N, $CF_3$, $C_1$-$C_3$ alkoxy, and —$NR_5R_6$; —CO—($C_1$-$C_4$ alkyl); —$SO_2$—$NR_5R_6$; —CO—$NR_5R_6$; —$SO_2$—($C_1$-$C_4$ alkyl); or =O;

$R_{11}$ is selected from morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four groups that are independently $C_1$-$C_6$ alkyl, $C_1$-$C_6$ alkoxy, and halogen; or Rz and $R_d$ at each occurrence are independently —$(CH_2)_{0-4}$-$CO_2R_{20}$; —$(CH_2)_{0-4}$—$SO_2$—$NR_{21}R_{22}$; —$(CH_2)_{0-4}$—SO—($C_1$-$C_8$ alkyl); —$(CH_2)_{0-4}$—$SO_2$—($C_1$-$C_{12}$ alkyl), —$(CH_2)_{0-4}$—$SO_2$—($C_3$-$C_7$ cycloalkyl); —$(CH_2)_{0-4}$—N(H or $R_{20}$)—CO—O—$R_{20}$; —$(CH_2)_{0-4}$—N(H or $R_{20}$)—CO—N($R_{20}$)$_2$; —$(CH_2)_{0-4}$—N—CS—N($R_{20}$)$_2$; —$(CH_2)_{0-4}$—N(—H or $R_{20}$)—CO—$R_{21}$; —$(CH_2)_{0-4}$—$NR_{21}R_{22}$; —$(CH_2)_{0-4}$—$R_{11}$; —$(CH_2)_{0-4}$—O—CO—($C_1$-$C_6$ alkyl); —$(CH_2)_{0-4}$—O—P(O)—$(OR_5)_2$; —$(CH_2)_{0-4}$—O—CO—N($R_{20}$)$_2$; —$(CH_2)_{0-4}$—O—CS—N($R_{20}$)$_2$; —$(CH_2)_{0-4}$—O—($R_{20}$)$_2$; —$(CH_2)_{0-4}$—O—($R_{20}$)—$CO_2H$; —$(CH_2)_{0-4}$—S—($R_{20}$); —$(CH_2)_{0-4}$—O—($C_1$-$C_6$ alkyl optionally substituted with one, two, three, four, or five halogens); $C_3$-$C_7$ cycloalkyl; —$(CH_2)_{0-4}$—N(—H or $R_{20}$)—$SO_2$—$R_{21}$; or —$(CH_2)_{0-4}$—$C_3$-$C_7$ cycloalkyl; wherein $R_{20}$ is selected from $C_1$-$C_6$ alkyl, —$(CH_2)_{0-2}$—$(R_{17})$, $C_2$-$C_6$ alkenyl, $C_2$-$C_6$ alkynyl, $C_3C_7$ cycloalkyl, and —$(CH_2)_{0-2}$—$(R_{18})$; or Rz and $R_d$ at each occurrence are independently $C_2$-$C_6$ alkenyl or $C_2$-$C_6$ alkynyl, each of which is optionally substituted with $C_1$-$C_3$ alkyl, F, Cl, Br, I, OH, SH, C≡N, $CF_3$, $C_1$-$C_3$ alkoxy, or —$NR_5R_6$; or the A ring is an aromatic hydrocarbon selected from phenyl, naphthyl, tetralinyl, indanyl, dihydronaphthyl or 6,7,8,9-tetrahydro-5H-benzo[a]cycloheptenyl, wherein each aromatic hydrocarbon is optionally substituted with one, two, three, or four Rz and/or $R_d$ groups which at each occurrence can be the same or different and are:

$C_1$-$C_6$ alkyl, optionally substituted with one, two or three substituents selected from $C_1$-$C_3$ alkyl, halogen, OH, SH, C≡N, $CF_3$, $C_1$-$C_3$ alkoxy, and —$NR_5R_6$; or —OH; —$NO_2$; halogen; —$CO_2H$; —C≡N; —$(CH_2)_{0-4}$—CO—$NR_{21}R_{22}$; —$(CH_2)_{0-4}$—CO—($C_1$-$C_{12}$ alkyl), —$(CH_2)_{0-4}$—CO—($C_2$-$C_{12}$ alkenyl), —$(CH_2)_{0-4}$—CO—($C_2$-$C_{12}$ alkynyl), —$(CH_2)_{0-4}$—CO—($C_3$-$C_7$ cycloalkyl), —$(CH_2)_{0-4}$-CO—$R_{17}$; —$(CH_2)_{0-4}$—CO—$R_{18}$; —$(CH_2)_{0-4}$—CO—$R_{19}$; —$(CH_2)_{0-4}$—CO—$R_{11}$; —$(CH_2)_{0-4}$—$CO_2R_{20}$; —$(CH_2)_{0-4}$—$SO_2$—$NR_{21}R_{22}$; —$(CH_2)_{0-4}$—SO—($C_1$-$C_8$ alkyl); —$(CH_2)_{0-4}$—$SO_2$—($C_1$-$C_{12}$ alkyl), —$(CH_2)_{0-4}$—$SO_2$—($C_3$-$C_7$ cycloalkyl); —$(CH_2)_{0-4}$—N(H or $R_{20}$)—$CO_2R_{20}$; —$(CH_2)_{0-4}$—N(H or $R_{20}$)—CO—N($R_{20}$)$_2$; —$(CH_2)_{0-4}$—N—CS—N($R_{20}$)$_2$; —$(CH_2)_{0-4}$—N(—H or $R_{20}$)—CO—$R_{21}$; —$(CH_2)_{0-4}$—$NR_{21}R_{22}$; —$(CH_2)_{0-4}$—$R_{11}$; —$(CH_2)_{0-4}$—O—CO—($C_1$-$C_6$ alkyl); —$(CH_2)_{0-4}$—O—P(O)—$(OR_5)_2$; —$(CH_2)_{0-4}$—O—CO—N($R_{20}$)$_2$; —$(CH_2)_{0-4}$—O—CS—N($R_{20}$)$_2$; —$(CH_2)_{0-4}$—O—($R_{20}$)$_2$; —$(CH_2)_{0-4}$—O—($R_{20}$)—$CO_2H$; —$(CH_2)_{0-4}$—S—($R_{20}$); —$(CH_2)_{0-4}$—O—($C_1$-$C_6$ alkyl optionally substituted with one, two, three, four, or five —F); $C_3$-$C_7$ cycloalkyl; —$(CH_2)_{0-4}$—N(—H or $R_{20}$)—$SO_2$—$R_{21}$; —$(CH_2)_{0-4}$—$C_3$-$C_7$ cycloalkyl; or $C_2$-$C_6$ alkenyl or $C_2$-$C_6$ alkynyl each of which is optionally substituted with $C_1$-$C_3$ alkyl, F, Cl, Br, I, OH, SH, C≡N, $CF_3$, $C_1$-$C_3$ alkoxy, or —$NR_5R_6$;

$R_a$ and $R_b$ are independently selected from $C_1$-$C_3$ alkyl, F, OH, SH, C≡N, $CF_3$, $C_1$-$C_6$ alkoxy, =O, and —$NR_5R_6$; or $R_a$ and $R_b$ and the carbon to which they are attached form a $C_3$-$C_7$ spirocycle which is optionally substituted with 1 or 2 groups that are independently $C_1$-$C_4$ alkyl, $C_1$-$C_4$ alkoxy, halogen, $CF_3$, or CN;

$R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino and —OC(=O)-mono- or dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, CF$_3$, OCF$_3$, C$_1$-C$_4$ alkoxy, amino, and mono- or dialkylamino; or R$_1$ is aryl, heteroaryl, heterocyclyl, aryl C$_1$-C$_6$ alkyl, heteroaryl C$_1$-C$_6$ alkyl, or heterocycloalkyl C$_1$-C$_6$ alkyl, wherein
- each aryl group at each occurrence is optionally substituted with 1, 2, 3, 4, or 5 R$_{50}$ groups;
- each heteroaryl at each occurrence is optionally substituted with 1, 2, 3, 4, or 5 R$_{50}$ groups;
- each heterocycloalkyl group at each occurrence is optionally substituted with 1, 2, 3, 4, or 5 groups that are independently R$_{50}$ or =O;

R$_1$ is G-L-A-E-W—, wherein
W is a bond, absent, —S—, —S(O)—, —SO$_2$—, —O—, —NH— or —N(C$_1$-C$_4$ alkyl);

E is a bond, absent, or C$_1$-C$_3$ alkylene;

A is absent, alkyl, aryl or cycloalkyl where each aryl or cycloalkyl is optionally substituted with one, two or three R$_{100}$ groups; heteroaryl optionally substituted with 1 or 2 R$_{100}$ groups; or heterocycloalkyl optionally substituted with 1 or 2 R$_{200}$ groups, wherein R$_{100}$ at each occurrence is independently selected from NO$_2$, C≡N, C$_1$-C$_6$ alkyl, C$_2$-C$_6$ alkenyl, C$_2$-C$_6$ alkynyl, —N(R)CO(R')R, —CO$_2$—R$_{25}$, —NH—CO$_2$—R$_{25}$, —O—(C$_2$-C$_6$ alkyl) —CO$_2$H, —NRR', —SR, CH$_2$OH, —C(O)—(C$_1$-C$_6$)alkyl, —C(O)NRR', —SO$_2$NRR', CO$_2$H, CF$_3$, halogen, C$_1$-C$_3$ alkoxy, —OCF$_3$, —NH$_2$, OH, CN, halogen, and —(CH$_2$)$_{0-2}$—O—(CH$_2$)$_{0-2}$—OH;
wherein
R$_{25}$ is selected from C$_1$-C$_6$ alkyl, —(CH$_2$)$_{0-2}$—cycloalkyl, —(CH$_2$)$_{0-2}$-aryl, where the aryl is optionally substituted with halogen, hydroxy, C$_1$-C$_6$ alkyl, C$_1$-C$_6$ alkyl, amino, mono(C$_1$-C$_6$) alkylamino, or di(C$_1$-C$_6$)alkylamino, and hydrogen, and
R and R' at each occurrence are independently hydrogen, C$_1$-C$_6$ alkyl, —(CH$_2$)$_{0-2}$-aryl, or —(CH$_2$)$_{02}$-cycloalkyl, where each aryl or cycloalkyl is optionally substituted with halogen, hydroxy, C$_1$-C$_6$ alkyl, C$_1$-C$_6$ alkyl, amino, mono(C$_1$-C$_6$)alkylamino, or di(C$_1$-C$_6$)alkylamino;
R$_{200}$ at each occurrence is independently selected from =O, C$_1$-C$_3$ alkyl, CF$_3$, F, Cl, Br, I, C$_1$-C$_3$ alkoxy, OCF$_3$, NH$_2$, OH, and C≡N;

provided that L is a bond or absent when G is absent, or

L is —C(O)—, —S(O)—, —SO$_2$—, —O—, —C(R$_{110}$)(R$_{112}$)O—, —OC(R$_{110}$) (R$_{112}$)—, —N(R$_{110}$)—, —CON(R$_{110}$)—, —N(R$_{110}$)CO—, —C(R$_{110}$)(R')—, —C(OH)R$_{110}$—, —SO$_2$NR$_{110}$—, —N(R$_{110}$)SO$_2$—, —N(R$_{110}$)CON(R$_{112}$)—, N(R$_{110}$)CSN(R$_{112}$)—, —OCO$_2$—, —NCO$_2$—, or —OCON(R$_{110}$)—, wherein
R$_{110}$ and R$_{112}$ are independently hydrogen, C$_1$-C$_4$ alkyl, C$_1$-C$_4$ hydroxyalkyl, C$_1$-C$_4$ alkoxy C$_1$-C$_4$ alkyl or C$_1$-C$_4$ fluoroalkyl;

and

G is absent or C$_1$-C$_{10}$ alkyl optionally substituted with 1, 2, or 3 groups independently selected from —CO$_2$H, —CO$_2$(C$_1$-C$_4$ alkyl), C$_1$-C$_6$ alkoxy, —OH, —NRR', —C$_1$-C$_6$ haloalkyl, —(C$_1$-C$_{10}$ alkyl)-O—(C$_3$-C$_3$ alkyl), —C$_2$-C$_{10}$ alkenyl, —C$_2$-C$_{10}$ alkynyl, —C$_4$-C$_{10}$ alkyl chain with one double bond and one triple bond, aryl optionally substituted with 1, 2, or 3 R$_{100}$, heteroaryl optionally substituted with 1, 2, or 3 R$_{100}$, and C$_1$-C$_6$ alkyl;

or

G is —(CH$_2$)$_{0-3}$—(C$_3$-C$_7$) cycloalkyl where the cycloalkyl is optionally substituted with one, two or three substituents independently selected from —CO$_2$H, —CO$_2$—(C$_1$-C$_4$ alkyl), C$_1$-C$_6$ alkoxy, OH, —NH$_2$, —C$_1$-C$_6$ haloalkyl, —(C$_1$-C$_{10}$ alkyl)-O—(C$_1$-C$_3$ alkyl), —C$_2$-C$_{10}$ alkenyl with 1 or 2 double bonds, C$_2$-C$_{10}$ alkynyl with 1 or 2 triple bonds, —C$_4$-C$_{10}$ alkyl chain with one double bond and one triple bond, aryl optionally substituted with R$_{100}$, heteroaryl optionally substituted with R$_{100}$, mono(C$_1$-C$_6$ alkyl)amino, di(C$_1$-C$_6$ alkyl) amino, and C$_1$-C$_6$ alkyl, or G is —(CH$_2$)$_{0-4}$-aryl, —(CH$_2$)$_{0-4}$-heteroaryl, or —(CH$_2$)$_{0-4}$-heterocycle, wherein the aryl, heteroaryl —(CH$_2$)$_{0-4}$-heterocycle, groups are optionally substituted with 1, 2, or 3 R$_{100}$, wherein the heterocycle group is optionally substituted with 1 or 2 R$_{200}$ groups; or G is —C(R$_{10}$)(R$_{12}$)—CO—NH—R$_{14}$ wherein
R$_{10}$ and R$_{12}$ are the same or different and are selected from H, —C$_1$-C$_6$ alkyl, —(C$_1$-C$_4$ alkyl)-aryl, where the aryl is optionally substituted with 1, 2, or 3 R$_{100}$ groups; —(C$_1$-C$_4$ alkyl)-heteroaryl where the heteroaryl is optionally substituted with 1, 2, or 3 R$_{100}$ groups; —(C$_1$-C$_4$ alkyl)-heterocycle, where the heterocycle is optionally substituted with 1 or 2 R$_{200}$ groups; heteroaryl optionally substituted with 1, 2, or 3 R$_{100}$ groups; heterocycle optionally substituted with 1 or 2 R$_{200}$ groups; —(CH$_2$)$_{1-4}$—OH, —(CH$_2$)$_{1-4}$—Y—(CH$_2$)$_{1-4}$-aryl where the aryl is optionally substituted with 1, 2, or 3 R$_{100}$ groups; —(CH$_2$)$_{1-4}$—Y—(CH$_2$)$_{1-4}$-heteroaryl where the heteroaryl is optionally substituted with 1, 2, or 3 R$_{100}$ groups; -aryl optionally substituted with 1, 2, or 3 R$_{100}$ groups, -heteroaryl optionally substituted with 1, 2, or 3 R$_{100}$ groups, and -heterocycle optionally substituted with 1, 2, or 3 R$_{200}$ groups, wherein
Y is —O—, —S—, —NH—, or —NH(C$_1$-C$_6$ alkyl); and R$_{14}$ is H, —C$_1$-C$_6$ alkyl, -aryl optionally substituted with 1, 2, or 3 R$_{100}$ groups, -heteroaryl optionally substituted with 1, 2, or 3 R$_{100}$ groups, -heterocycle optionally substituted with 1 or 2 R$_{200}$ groups, —(C$_1$-C$_4$ alkyl)-aryl, where the aryl is optionally substituted with 1, 2, or 3 R$_{100}$ groups; —(C$_1$-C$_4$ alkyl)-heteroaryl where the heteroaryl is optionally substituted with 1, 2, or 3 R$_{100}$ groups; —(C$_1$-C$_4$ alkyl)-heterocycle, where the heterocycle is optionally substituted with 1 or 2 R$_{200}$ groups, or —(CH$_2$)$_{0-2}$—O—(CH$_2$)$_{1-2}$—OH;

R$_2$ and R$_3$ are independently selected from —H, C$_1$-C$_6$ alkyl, optionally substituted with one, two or three substituents selected from C$_1$-C$_3$ alkyl, —F, —Cl, —Br, —I, —OH, —SH, —C≡N, —CF$_3$, C$_1$-C$_3$ alkoxy, and —NR$_5$R$_6$; —(CH$_2$)$_{0-4}$—R$_{17}$; —(CH$_2$)$_{0-4}$—R$_{18}$; C$_2$-C$_6$ alkenyl or C$_2$-C$_6$ alkynyl, wherein each is optionally substituted with one, two or three substituents selected from —F, —Cl, —OH, —SH, —C≡N, —CF$_3$, C$_1$-C$_3$ alkoxy, and —NR$_5$R$_6$; —(CH$_2$)$_{0-4}$—C$_3$-C$_7$ cycloalkyl, optionally substituted with one, two or three substituents selected from —F, —Cl, —OH, —SH, —C≡N, —CF$_3$, C$_1$-C$_3$ alkoxy, and —NR$_5$R$_6$; wherein R$_5$ and R$_6$ at each occurrence are independently H or C$_1$-C$_6$ alkyl; or $R_5$ and $R_6$ and the nitrogen to which they are attached, at each occurrence form a 5 or 6 membered heterocycloalkyl ring; or $R_2$, $R_3$ and the carbon to which they are attached form a carbocycle of three thru seven carbon atoms, wherein one carbon atom is optionally replaced by a group selected from —O—, —S—, —SO$_2$—, or —NR$_7$—;

$R_{15}$ at each occurrence is independently selected from hydrogen, $C_1$-$C_6$ alkyl, $C_1$-$C_6$ alkoxy, $C_1$-$C_6$ alkoxy $C_1$-$C_6$ alkyl, hydroxy $C_1$-$C_6$ alkyl, halo $C_1$-$C_6$ alkyl, $C_1$-$C_6$ alkanoyl, each of which is unsubstituted or substituted with 1, 2, 3, or 4 groups independently selected from halogen, alkyl, hydroxy, alkoxy, NH$_2$, and —R$_{26}$—R$_{27}$; and —R$_{26}$-R$_{27}$; wherein $R_{26}$ is selected from a bond, —C(O)—, —SO$_2$—, —CO$_2$—, —C(O)NR$_5$—, and —NR$_5$C(O)—, $R_{27}$ is selected from $C_1$-$C_6$ alkyl, $C_1$-$C_6$ alkoxy, aryl $C_1$-$C_6$ alkyl, heterocycloalkyl, and heteroaryl, wherein each of the above is unsubstituted or substituted with 1, 2, 3, 4, or 5 groups that are independently $C_1$-$C_4$ alkyl, $C_1$-$C_4$ alkoxy, halogen, haloalkyl, hydroxyalkyl, —NR$_5$R$_6$, —C(O)NR$_5$R$_6$.

Preferred compounds of formula A-I include those wherein $R_2$ and $R_3$ are independently selected from H; $C_1$-$C_6$ alkyl optionally substituted with 1, 2, or 3 substituents that are independently selected from $C_1$-$C_4$ alkyl, halogen, —CF$_3$, and $C_1$-$C_4$ alkoxy; and $C_2$-$C_6$ alkenyl or $C_2$-$C_6$ alkynyl wherein each is optionally substituted with one, two or three substituents selected from —F, —Cl, —OH, —SH, —C≡N, —CF$_3$, $C_1$-$C_3$ alkoxy, and —NR$_5$R$_6$; or $R_2$, $R_3$ and the carbon to which they are attached form a carbocycle of three thru seven carbon atoms, wherein one carbon atom is optionally replaced by a group selected from —O—, —S—, —SO$_2$—, or —NR$_7$—; wherein $R_7$ is selected from H, —C$_1$-C$_8$ alkyl optionally substituted with 1, 2, or 3 groups independently selected from —OH, —NH$_2$, phenyl and halogen; $C_3$-$C_8$ cycloalkyl; —($C_1$-$C_2$ alkyl)-($C_3$-$C_8$ cycloalkyl); —($C_1$-$C_6$ alkyl)-O—($C_1$-$C_4$ alkyl); $C_2$-$C_6$ alkenyl; $C_2$-$C_6$ alkynyl; phenyl; naphthyl; heteroaryl; heterocycloalkyl.

Other preferred compounds of formula A-I include those wherein $R_{15}$ at each occurrence is independently selected from hydrogen, $C_1$-$C_4$ alkyl, $C_1$-$C_4$ alkoxy, $C_1$-$C_4$ alkanoyl, each of which is unsubstituted or substituted with 1, 2, 3, or 4 groups independently selected from halogen, alkyl, hydroxy, $C_1$-$C_4$ alkoxy, and NH$_2$; and —R$_{26}$—R$_{27}$; wherein $R_{26}$ is selected from a bond, —C(O)—, —SO$_2$—, —CO$_2$—, —C(O)NR$_5$—, and —NR$_5$C(O)—; and $R_{27}$ is selected from $C_1$-$C_6$ alkyl, $C_1$-$C_6$ alkoxy, and benzyl, wherein each of the above is unsubstituted or substituted with 1, 2, 3, 4, or 5 groups that are independently $C_1$-$C_4$ alkyl, $C_1$-$C_4$ alkoxy, halogen, halo $C_1$-$C_4$ alkyl, hydroxyalkyl, —C(O)NR$_5$R$_6$, or —NR$_5$R$_6$.

Still other preferred compounds of formula A-I include those wherein $R_1$ is $C_1$-$C_{10}$ alkyl optionally substituted with 1, 2, or 3 groups independently selected from halogen, —OH, =O, —SH, —CN, —CF$_3$, —C$_1$-C$_4$ alkoxy, amino, mono- or dialkylamino, —N(R)C(O) R', —OC(=O)-amino and —OC(=O)-mono- or dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, CF$_3$, OCF$_3$, $C_1$-$C_4$ alkoxy, amino, and mono- or dialkylamino; or $R_1$ is aryl, heteroaryl, heterocyclyl, aryl $C_1$-$C_6$ alkyl, heteroaryl $C_1$-$C_6$ alkyl, or heterocycloalkyl $C_1$-$C_6$ alkyl; wherein each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O; and $R_{50}$ at each occurrence is independently selected from halogen, OH, SH, CN, —CO—($C_1$-$C_4$ alkyl), —CO$_2$—($C_1$-$C_4$ alkyl), —SO$_2$—NR$_5$R$_6$, —NR$_7$R$_8$, —CO—NR$_5$R$_6$, —CO—NR$_7$R$_8$, —SO$_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —NR$_5$R$_6$, CN, $C_1$-$C_4$ haloalkyl, $C_1$-$C_4$ haloalkoxy, phenyl, NR$_7$R$_8$, and $C_1$-$C_4$ alkoxy.

Other preferred compounds of A-I are those where the A-ring is benzo optionally substituted with one or two $R_z$ or $R_d$ groups;

$R_{15}$, $R_2$, and $R_3$ are all hydrogen; and

T is oxygen or NH, and $R_N$ is phenyl optionally substituted with 1, 2, or 3 groups independently selected from $C_1$-$C_6$ alkyl optionally substituted with 1, 2, or 3 substituents selected from the group consisting of halogen, hydroxy, —NR$_{1-a}$R$_{1-b}$ where $R_{1-a}$ and $R_{1-b}$ independently represent $C_1$-$C_6$ alkyl, —C≡N, —CF$_3$, and $C_1$-$C_3$ alkoxy; halogen; $C_1$-$C_6$ alkoxy; —NR$_{N-2}$R$_{N-3}$ where $R_{N-2}$ and $R_{N-3}$ independently represent $C_1$-$C_6$ alkyl; and hydroxy. In these preferred compounds of A-I, $R_1$ is phenyl substituted with one or, preferably, two halogens, preferably, fluoro. More preferably, $R_z$ and $R_d$ are independently hydrogen or $C_1$-$C_6$ alkyl, even more preferably one of $R_z$ and $R_d$ is hydrogen and the other is $C_1$-$C_3$ alkyl. $R_N$ is preferably phenyl optionally substituted with one or two independently selected halogen, $C_1$-$C_3$ alkyl or $C_1$-$C_3$ alkoxy groups.

Yet other preferred compounds of formula A-I include those of formula A-1-1, i.e., compounds of formula A-I wherein Rz and $R_d$ are independently selected from $C_1$-$C_6$ alkyl optionally substituted with one, two or three substituents selected from $C_1$-$C_3$ alkyl, halogen, OH, SH, C≡N, CF$_3$, $C_1$-$C_3$ alkoxy, and —NR$_5$R$_6$; hydroxy; nitro; halogen; —CO$_2$H; cyano; and —(CH$_2$)$_{0-4}$—CO—NR$_{21}$R$_{22}$; wherein $R_{21}$ and $R_{22}$ independently represent hydrogen, $C_1$-$C_6$ alkyl, hydroxyl ($C_1$-$C_6$)alkyl, amino($C_1$-$C_6$)alkyl, haloalkyl, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —C$_2$-C$_6$ alkenyl, —C$_2$-C$_6$ alkynyl, —$C_1$-$C_6$ alkyl chain with one double bond and one triple bond, phenyl, naphthyl, heteroaryl; or Rz and $R_d$ are independently selected from —(CH$_2$)$_{0-4}$—CO—($C_1$-$C_{12}$ alkyl); —(CH$_2$)$_{0-4}$—CO—($C_2$-$C_{12}$ alkenyl); —(CH$_2$)$_{0-4}$—CO—($C_2$-$C_{12}$)alkynyl; —(CH$_2$)$_{0-4}$—CO—($C_3$-$C_7$ cycloalkyl); —(CH$_2$)$_{0-4}$—CO-phenyl; —(CH$_2$)$_{0-4}$—CO-naphthyl; —(CH$_2$)$_{0-4}$—CO-heteroaryl; —(CH$_2$)$_{0-4}$—CO-heterocycloalkyl; —(CH$_2$)$_{0-4}$—CO$_2$R$_{20}$; wherein $R_{20}$ is selected from $C_1$-$C_6$ alkyl, —$(CH_2)_{0-2}$-(phenyl), —$(CH_2)_{0-2}$-(naphthyl), $C_2$-$C_6$ alkenyl, $C_2$-$C_6$ alkynyl, $C_3$-$C_7$ cycloalkyl, and —$(CH_2)_{0-2}$-(heteroaryl), or Rz and $R_d$ are independently selected from —$(CH_2)_{0-4}$—$SO_2$—$NR_{21}R_{22}$; —$(CH_2)_{0-4}$—SO—$(C_1$-$C_8$ alkyl); —$(CH_2)_{0-4}$—$SO_2$—$(C_1$-$C_{12}$ alkyl); —$(CH_2)_{0-4}$—$SO_2$—$(C_3$-$C_7$ cycloalkyl); —$(CH_2)_{0-4}$—N(H or $R_{20}$)—$CO_2R_{20}$; —$(CH_2)_{0-4}$—N(H or $R_{20}$)—CO—$N(R_{20})_2$; —$(CH_2)_{0-4}$—N—CS—$N(R_{20})_2$; —$(CH_2)_{0-4}$—N(—H or $R_{20}$)—CO—$R_{21}$; —$(CH_2)_{0-4}$—$NR_{21}R_{22}$; —$(CH_2)_{0-4}$-heterocycloalkyl; —$(CH_2)_{0-4}$—O—CO—$(C_1$-$C_6$ alkyl); —$(CH_2)_{0-4}$—O—P(O)—$(OR_5)_2$; —$(CH_2)_{0-4}$—O—CO—$N(R_{20})_2$; —$(CH_2)_{0-4}$—O—CS—$N(R_{20})_2$; —$(CH_2)_{0-4}$—O—$(R_{20})$; —$(CH_2)_{0-4}$—O—$(R_{20})$—$CO_2H$; —$(CH_2)_{0-4}$—S—$(R_{20})$; —$(CH_2)_{0-4}$—O-halo($C_1$-$C_6$)alkyl; —$(CH_2)_{0-4}$—O—$(C_1$-$C_6)$alkyl; $C_3$-$C_8$ cycloalkyl; and —$(CH_2)_{0-4}$—N(—H or $R_{20}$)—$SO_2$—$R_{21}$; or Rz and $R_d$ are independently $C_2$-$C_6$ alkenyl or $C_2$-$C_6$ alkynyl, each of which is optionally substituted with $C_1$-$C_4$ alkyl, halogen, hydroxy, SH, cyano, $CF_3$, $C_1$-$C_4$ alkoxy, or $NR_5R_6$; wherein
  each aryl group at each occurrence is optionally substituted with 1, 2, 3, 4, or 5 $R_{50}$ groups;
  each heteroaryl at each occurrence is optionally substituted with 1, 2, 3, 4, or 5 $R_{50}$ groups;
  each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—$(C_1$-$C_4$ alkyl), —$CO_2$—$(C_1$-$C_4$ alkyl), —$SO_2$—$NR_5R_6$, —$NR_7R_8$, —CO—$NR_5R_6$, —CO—$NR_7R_8$, —$SO_2$—$(C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;
  wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_6$ haloalkyl, $C_1$-$C_6$ haloalkoxy, phenyl, $NR_7R_8$, and $C_1$-$C_6$ alkoxy.

Preferred compounds of formula A-I-1 include those of formula A-II:

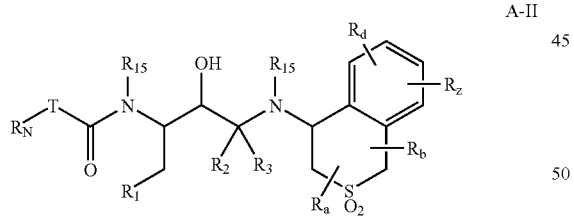

A-II

Preferred compounds of formula A-II include those wherein $R_2$ and $R_3$ are independently selected from H; $C_1$-$C_6$ alkyl optionally substituted with 1, 2, or 3 substituents that are independently selected from $C_1$-$C_4$ alkyl, halogen, —$CF_3$, and $C_1$-$C_4$ alkoxy; $C_2$-$C_6$ alkenyl or $C_2$-$C_6$ alkynyl, wherein each is optionally substituted with one, two or three substituents selected from —F, —Cl, —OH, —SH, —C≡N, —$CF_3$, $C_1$-$C_3$ alkoxy, and —$NR_5R_6$;
  $R_5$ and $R_6$ at each occurrence are independently H or $C_1$-$C_6$ alkyl; or
  $R_5$ and $R_6$ and the nitrogen to which they are attached, at each occurrence form a 5 or 6 membered heterocycloalkyl ring;

or $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein
  $R_7$ is selected from H; —$C_1$-$C_4$ alkyl optionally substituted with 1, 2, or 3 groups independently selected from —OH, —$NH_2$, and halogen; —$C_3$-$C_6$ cycloalkyl; —$(C_1$-$C_4$ alkyl)-O—$(C_1$-$C_4$ alkyl); —$C_2$-$C_4$ alkenyl; and —$C_2$-$C_4$ alkynyl.

Even more preferred compounds of formula A-II include those wherein $R_{15}$ at each occurrence is independently selected from hydrogen, $C_1$-$C_4$ alkyl, $C_1$-$C_6$ alkanoyl, benzyl optionally substituted with $OCH_3$, —C(O)-tertiary butyl, and —$CO_2$-benzyl.

Still other more preferred compounds of formula A-II include those wherein $R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino OC(=O)-mono- and dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, $CF_3$, $OCF_3$, $C_1$-$C_4$ alkoxy, amino, and mono- or dialkylamino; or $R_1$ is aryl, heteroaryl, heterocyclyl, aryl $C_1$-$C_6$ alkyl, heteroaryl $C_1$-$C_6$ alkyl, or heterocycloalkyl $C_1$-$C_6$ alkyl;
  each aryl group at each occurrence is optionally substituted with 1, 2, 3, 4, or 5 $R_{50}$ groups;
  each heteroaryl at each occurrence is optionally substituted with 1, 2, 3, 4, or 5 $R_{50}$ groups;
  each heterocycloalkyl group at each occurrence is optionally substituted with 1, 2, 3, 4, or 5 groups that are independently $R_{50}$ or =O;
    $R_{50}$ at each occurrence is independently selected from halogen, OH, SH, CN, —CO—$(C_1$-$C_4$ alkyl), —$CO_2$—$(C_1$-$C_4$ alkyl), —$SO_2$—$NR_5R_6$, —$NR_7R_8$, —CO—$NR_5R_6$, —CO—$NR_7R_8$, —$SO_2$—$(C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;
      wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_4$ haloalkyl, $C_1$-$C_4$ haloalkoxy, phenyl, $NR_7R_8$, and $C_1$-$C_4$ alkoxy.

Other preferred compounds of A-II are those where $R_{15}$, $R_2$, and $R_3$ are all hydrogen; and T is oxygen or NH, and $R_N$ is phenyl optionally substituted with 1, 2, or 3 groups independently selected from $C_1$-$C_6$ alkyl optionally substituted with 1, 2, or 3 substituents selected from the group consisting of halogen, hydroxy, —$NR_{1-a}R_{1-b}$ where $R_{1-a}$ and $R_{1-b}$ independently represent $C_1$-$C_6$ alkyl, —C≡N, —$CF_3$, and $C_1$-$C_3$ alkoxy; halogen; $C_1$-$C_6$ alkoxy; —$NR_{N-2}R_{N-3}$ where $R_{N-2}$ and $R_{N-3}$ independently represent $C_1$-$C_6$ alkyl; and hydroxy. In these preferred compounds of A-II, $R_1$ is phenyl substituted with one or, preferably, two halogens, preferably, fluoro. More preferably, $R_z$ and $R_d$ are independently hydrogen or $C_1$-$C_6$ alkyl, even more preferably one of $R_z$ and $R_d$ is hydrogen and the other is $C_1$-$C_3$ alkyl. $R_N$ is preferably phenyl optionally substituted with one or two independently selected halogen, $C_1$-$C_3$ alkyl or $C_1$-$C_3$ alkoxy groups.

Other preferred compounds of formula A-II include those of formula A-II-1, i.e., compound of formula A-II wherein $R_{50}$ at each occurrence is independently selected from halogen, OH, SH, —$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;
  wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_4$ haloalkyl, $C_1$-$C_4$ haloalkoxy, phenyl, $NR_7R_8$, and $C_1$-$C_4$ alkoxy.

Preferred compounds of formula A-II-1 include those of formula A-III:

A-III

More preferred compounds of formula A-III include those of formula A-III-1, i.e., compounds of formula A-III wherein $R_1$ is phenyl, phenyl $C_1$-$C_6$ alkyl, naphthyl, or naphthyl $C_1$-$C_6$ alkyl, wherein the phenyl or naphthyl group is optionally substituted with 1, 2, 3, 4, or 5 $R_{50}$ groups.

Still more preferred compound of formula A-III-1 include those of formula A-III-2, i.e., compound of formula A-III-1 wherein $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein
  $R_7$ is H, —$C_1$-$C_8$ alkyl optionally substituted with 1, 2, or 3 groups independently selected from —OH, —$NH_2$, and halogen; —$C_2$-$C_4$ alkenyl; or —$C_2$-$C_4$ alkynyl.

Preferred compounds of formula A-III-2 include those of formula A-III-3, i.e., compounds of formula A-III-2 wherein $R_2$, $R_3$ and the carbon to which they are attached form a carbocycle of three thru six carbon atoms.

Equally preferred compound of formula A-III-2 include those of formula A-III-4, i.e., compounds of formula A-III-2 compounds wherein $R_2$, $R_3$ and the carbon to which they are attached form a heterocycloalkyl group containing 2 to 5 carbon atoms and one group selected from —O—, —S—, —$SO_2$—, and —$NR_7$—; wherein
  $R_7$ is H, —$C_1$-$C_8$ alkyl optionally substituted with 1, 2, or 3 groups independently selected from —OH, —$NH_2$, and halogen; —$C_2$-$C_4$ alkenyl; or —$C_2$-$C_4$ alkynyl.

Other equally preferred compounds of formula A-III-1 include those compounds of formula A-III-5, i.e., compounds of formula A-III-1 wherein $R_2$ and $R_3$ are independently selected from H; $C_1$-$C_6$ alkyl optionally substituted with 1, 2, or 3 substituents that are independently selected from $C_1$-$C_4$ alkyl, halogen, —$CF_3$, and $C_1$-$C_4$ alkoxy; $C_2$-$C_6$ alkenyl; and $C_2$-$C_6$ alkynyl.

More preferred compound of formulas A-III-3, A-III-4, and A-III-5 include those of formula A-III-6, i.e., compound of formulas A-III-3, A-III-4, and A-III-5 wherein $R_a$ and $R_b$ are independently selected from $C_1$-$C_6$ alkyl, $C_1$-$C_6$ alkoxy, halogen, CN, OH, hydroxyalkyl, $C_1$-$C_6$ haloalkyl, $C_1$-$C_6$ haloalkoxy, and —$C_1$-$C_6$ alkyl-$NR_5R_6$; or $R_a$ and $R_b$ are attached to the same carbon and form a $C_3$-$C_7$ spirocycle; and $R_{20}$ at each occurrence is independently H or $C_1$-$C_4$ alkyl.

Preferred compound of formula A-III-6 include those of formula A-III-6a, i.e., compounds of formula A-III-6 wherein Rz and $R_d$ are independently selected from $C_1$-$C_6$ alkyl optionally substituted with one, two or three substituents selected from $C_1$-$C_3$ alkyl, halogen, OH, SH, C≡N, $CF_3$, $C_1$-$C_3$ alkoxy, and —$NR_5R_6$; hydroxy; halogen; $C_2$-$C_6$ alkenyl or $C_2$-$C_6$ alkynyl, wherein
  the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$.

Other preferred compound of formula A-III-6 include those wherein

Rz and $R_d$ are —$(CH_2)_{0-4}$—CO—$NR_{21}R_{22}$, —$(CH_2)_{0-4}$—$SO_2$—$NR_{21}R_{22}$; —$(CH_2)_{0-4}$—SO—($C_1$-$C_8$ alkyl); —$(CH_2)_{0-4}$—$SO_2$—($C_1$-$C_{12}$ alkyl); —$(CH_2)_{0-4}$—$SO_2$—($C_3$-$C_7$ cycloalkyl); —$(CH_2)_{0-4}$—N(H or $R_{20}$)—CO—O—$R_{20}$; —$(CH_2)_{0-4}$—N(H or $R_{20}$)—CO—N($R_{20}$)$_2$; —$(CH_2)_{0-4}$—N—CS—N($R_{20}$)$_2$; —$(CH_2)_{0-4}$—N(—H or $R_{20}$)—CO—$R_{21}$; or —$(CH_2)_{0-4}$—$NR_{21}R_{22}$; wherein
  $R_{21}$ and $R_{22}$ independently represent hydrogen, $C_1$-$C_6$ alkyl, hydroxyl ($C_1$-$C_6$)alkyl, amino($C_1$-$C_6$)alkyl, haloalkyl, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, phenyl, naphthyl, or heteroaryl;
  each aryl group at each occurrence is optionally substituted with 1, 2, 3, 4, or 5 $R_{50}$ groups;
  each heteroaryl at each occurrence is optionally substituted with 1, 2, 3, 4, or 5 $R_{50}$ groups;
  each heterocycloalkyl group at each occurrence is optionally substituted with 1, 2, 3, 4, or 5 groups that are independently $R_{50}$ or =O.

Still other preferred compound of formula A-III-6 include those wherein

Rz and $R_d$ are —$(CH_2)_{0-4}$—CO—($C_1$-$C_{12}$ alkyl); —$(CH_2)_{0-4}$—CO—($C_2$-$C_{12}$alkenyl); $(CH_2)_{0-4}$—CO—($C_2$-$C_{12}$) alkynyl; —$(CH_2)_{0-4}$—CO—($C_3$-$C_7$ cycloalkyl); —$(CH_2)_{0-4}$—CO-phenyl; —$(CH_2)_{0-4}$—CO-naphthyl; —$(CH_2)_{0-4}$—CO-heteroaryl; —$(CH_2)_{0-4}$—CO-heterocycloalkyl; —$(CH_2)_{0-4}$—$CO_2R_{20}$; where
  $R_{20}$ is selected from $C_1$-$C_6$ alkyl, —$(CH_2)_{0-2}$-(phenyl), —$(CH_2)_{0-2}$-(naphthyl), $C_2$-$C_6$ alkenyl, $C_2$-$C_6$ alkynyl, $C_3$-$C_7$ cycloalkyl, and —$(CH_2)_{0-2}$-(heteroaryl);
  each aryl group and each heteroaryl group at each occurrence is optionally substituted with 1, 2, 3, 4, or 5 $R_{50}$ groups;
  each heterocycloalkyl group at each occurrence is optionally substituted with 1, 2, 3, 4, or 5 groups that are independently $R_{50}$ or =O.

Yet still other preferred compounds of formula A-III-6 include those wherein

Rz and $R_d$ are —$(CH_2)_{0-4}$—O—CO—($C_1$-$C_6$ alkyl); —$(CH_2)_{0-4}$—O—P(O)—$(OR_5)_2$; —$(CH_2)_{0-4}$—O—CO—N$(R_{20})_2$; —$(CH_2)_{0-4}$—O—CS—N$(R_{20})_2$; —$(CH_2)_{0-4}$—O—$(R_{20})$; —$(CH_2)_{0-4}$—O—$(R_{20})$—$CO_2H$; —$(CH_2)_{0-4}$—S—$(R_{20})$; —$(CH_2)_{0-4}$—O-halo($C_1$-$C_6$)alkyl; —$(CH_2)_{0-4}$-O—($C_1$-$C_6$)alkyl; $C_3$-$C_8$ cycloalkyl; or —$(CH_2)_{0-4}$—N(—H or $R_{20}$)—$SO_2$—$R_{21}$; wherein each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—($C_1$-$C_4$ alkyl), —$CO_2$—($C_1$-$C_4$ alkyl), —$SO_2$—$NR_5R_6$, —$NR_7R_8$, —CO—$NR_5R_6$, —CO—$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;
wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_6$ haloalkyl, $C_1$-$C_6$ haloalkoxy, phenyl, $NR_7R_8$, and $C_1$-$C_6$ alkoxy.

Other preferred compounds of formula A-III include those of formula A-III-7, i.e., compounds of formula A-III wherein $R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino and —OC(=O)-mono- or dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, $CF_3$, $OCF_3$, $C_1$-$C_4$ alkoxy, amino, and mono- or dialkylamino.

More preferred compounds of formula A-III-7 include those compounds of formula A-III-8, i.e., compounds of formula A-III-7 wherein $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein
$R_7$ is selected from H or —$C_1$-$C_4$ alkyl optionally substituted with 1 group selected from —OH, —$NH_2$, and halogen.

Preferred compounds of formula A-III-8 include those compounds of formula A-III-9, i.e., compounds of formula A-III-8 wherein $R_2$, $R_3$ and the carbon to which they are attached form a carbocycle of three thru six carbon atoms.

Other preferred compounds of formula A-III-8 include those compounds of formula A-III-10, i.e., compounds of formula A-III-8 wherein $R_2$, $R_3$, and the carbon to which they are attached form a heterocycloalkyl group containing 2 to 5 carbon atoms and one group selected from —O—, —S—, —$SO_2$—, and —$NR_7$—; wherein
$R_7$ is selected from H or —$C_1$-$C_4$ alkyl optionally substituted with 1 group selected from —OH, —$NH_2$, and halogen.

Still other preferred compounds of formula A-III-8 include those compounds of formula A-III-11, i.e., compounds of formula A-III-8 wherein $R_2$ and $R_3$ are independently selected from H; $C_1$-$C_6$ alkyl optionally substituted with 1, or 2 substituents that are independently selected from $C_1$-$C_4$ alkyl, halogen, —$CF_3$, and $C_1$-$C_4$ alkoxy; $C_2$-$C_6$ alkenyl; and $C_2$-$C_6$ alkynyl.

More preferred compound according to any one of formulas A-III-9, A-III-10, or A-III-11 include those of formula A-III-12, i.e., compounds according to any one of formulas of formulas A-III-9, A-III-10, or A-III-11 wherein $R_a$ and $R_b$ are independently selected from $C_1$-$C_3$ alkyl, F, OH, C≡N, $CF_3$, $C_1$-$C_6$ alkoxy, and —$NR_5R_6$; and $R_{20}$ at each occurrence is independently H or $C_1$-$C_4$ alkyl.

Preferred compounds of formula A-III-12 include those compounds wherein

Rz and $R_d$ are independently selected from $C_1$-$C_6$ alkyl optionally substituted with one, two or three substituents selected from $C_1$-$C_3$ alkyl, halogen, OH, SH, C≡N, $CF_3$, $C_1$-$C_3$ alkoxy, and —$NR_5R_6$; hydroxy; halogen;

$C_2$-$C_6$ alkenyl and $C_2$-$C_6$ alkynyl; wherein
the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$.

Other preferred compounds of formula A-III-12 include those compounds wherein

Rz and $R_d$ are —$(CH_2)_{0-4}$—CO—$NR_{21}R_{22}$, —$(CH_2)_{0-4}$—$SO_2$—$NR_{21}R_{22}$; —$(CH_2)_{0-4}$—SO—($C_1$-$C_8$ alkyl); —$(CH_2)_{0-4}$—$SO_2$—($C_1$-$C_{12}$ alkyl); —$(CH_2)_{0-4}$—$SO_2$—($C_3$-$C_7$ cycloalkyl); —$(CH_2)_{0-4}$—N(H or $R_{20}$)—CO—O—$R_{20}$; —$(CH_2)_{0-4}$—N(H or $R_{20}$)—CO—N$(R_{20})_2$; —$(CH_2)_{0-4}$—N—CS—N$(R_{20})_2$; —$(CH_2)_{0-4}$—N(—H or $R_{20}$)—CO—$R_{21}$; or —$(CH_2)_{0-4}$—$NR_{21}R_{22}$; wherein $R_{21}$ and $R_{22}$ independently represent hydrogen, $C_1$-$C_6$ alkyl, hydroxyl($C_1$-$C_6$)alkyl, amino($C_1$-$C_6$)alkyl, haloalkyl, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, phenyl, naphthyl, or heteroaryl;

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Still other preferred compounds of formula A-III-12 include those compounds wherein Rz and $R_d$ are —$(CH_2)_{0-4}$—CO—($C_1$-$C_{12}$ alkyl); —$(CH_2)_{0-4}$—CO—($C_2$-$C_{12}$ alkenyl); $(CH_2)_{0-4}$—CO—($C_2$-$C_{12}$)alkynyl; —$(CH_2)_{0-4}$-CO—($C_3$-$C_7$ cycloalkyl); —$(CH_2)_{0-4}$—CO-phenyl; —$(CH_2)_{0-4}$—CO-naphthyl; —$(CH_2)_{0-4}$—CO-heteroaryl; —$(CH_2)_{0-4}$—CO-heterocycloalkyl; —$(CH_2)_{0-4}$—$CO_2R_{20}$; where $R_{20}$ is selected from $C_1$-$C_6$ alkyl, —$(CH_2)_{0-2}$-(phenyl), —$(CH_2)_{0-2}$-(naphthyl), $C_2$-$C_6$ alkenyl, $C_2$-$C_6$ alkynyl, $C_3$-$C_7$ cycloalkyl, —$(CH_2)_{0-2}$-(heterocycloalkyl) and —$(CH_2)_{0-2}$-(heteroaryl);

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Yet other preferred compounds of formula A-III-12 include those compounds wherein Rz and $R_d$ are —$(CH_2)_{0-4}$—O—CO—$(C_1-C_6$ alkyl); —$(CH_2)_{0-4}$—O—P(O)—$(OR_5)_2$; —$(CH_2)_{0-4}$—O—CO—N$(R_{20})_2$; —$(CH_2)_{0-4}$—O—CS—N$(R_{20})_2$; —$(CH_2)_{0-4}$—O—$(R_{20})$; —$(CH_2)_{0-4}$—O—$(R_{20})$—$CO_2H$; —$(CH_2)_{0-4}$—S—$(R_{20})$; —$(CH_2)_{0-4}$—O-halo$(C_1-C_6)$alkyl; —$(CH_2)_{0-4}$—O—$(C_1-C_6)$alkyl; $C_3-C_8$ cycloalkyl; or —$(CH_2)_{0-4}$—N(—H or $R_{20}$)—$SO_2$—$R_{21}$; wherein each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—$(C_1-C_4$ alkyl), —$CO_2$—$(C_1-C_4$ alkyl), —$SO_2$—$NR_5R_6$, —$NR_7R_8$, —CO—$NR_5R_6$, —CO—$NR_7R_8$, —$SO_2$—$(C_1-C_4$ alkyl), $C_1-C_6$ alkyl, $C_2-C_6$ alkenyl, $C_2-C_6$ alkynyl, $C_1-C_6$ alkoxy, or $C_3-C_8$ cycloalkyl;

wherein the alkyl, alkenyl, alkynyl, alkoxy, or cycloalkyl groups are optionally substituted with 1, 2, or 3 substituents independently selected from $C_1-C_4$ alkyl, halogen, OH, SH, —$NR_5R_6$, CN, $C_1-C_6$ haloalkyl, $C_1-C_6$ haloalkoxy, phenyl, $NR_7R_8$, and $C_1-C_6$ alkoxy.

Preferred compounds of formula A-III-6a include those of formula A-IV

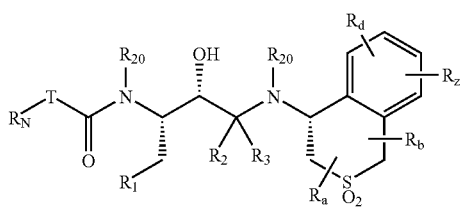

A-IV

Preferred compounds of formula A-IV include those wherein $R_2$ and $R_3$ are independently H or $C_1-C_4$ alkyl.

Other preferred compounds of formula A-IV include those of formula A-IV-1, i.e., compounds of formula A-IV wherein $R_a$ and $R_b$ are independently H or $C_1-C_3$ alkyl; and $R_1$ is phenyl, optionally substituted with 1, 2, or 3 $R_{50}$ groups; and $R_{15}$ at each occurrence is independently H or $C_1-C_4$ alkyl.

Preferred compounds of formula A-IV-1 include those of formula A-IV-2, i.e., compounds of formula A-IV-1 wherein $R_1$ is a dihalophenyl; and $R_2$ and $R_3$ are independently H or $C_1-C_4$ alkyl.

Preferred compounds of formula A-IV-2 include compounds of formula A-V

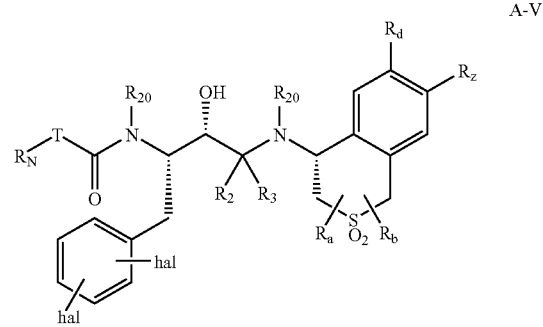

A-V wherein hal at each occurrence is independently selected from F, Cl, Br, and I.

More preferred compounds of formula A-V include those compounds wherein Rz is a $C_1-C_4$ alkyl group.

Other preferred compounds of formula A-IV-2 include compounds of formula A-VI

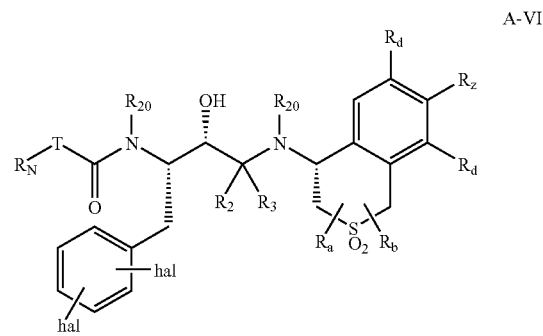

A-VI wherein hal at each occurrence is independently selected from F, Cl, Br, and I.

Preferred compounds of formula A-VI include those compounds wherein Rz is a $C_1-C_4$ alkyl group.

Other preferred compounds of formula A-IV-2 include compounds of formula A-VII

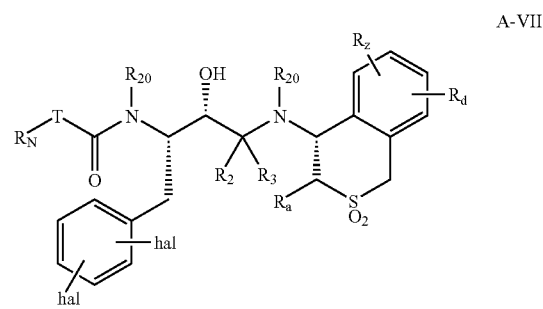

A-VII wherein $R_b$ is H.

Still other preferred compounds of formula A-IV-2 include compounds of formula A-VIII

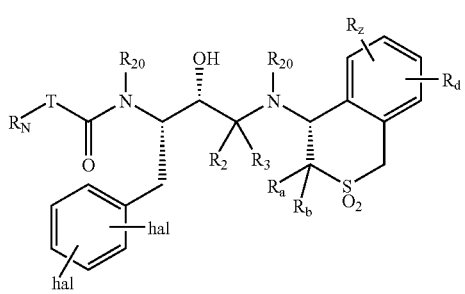

A-VIII.

Other preferred compounds of formula A-1-1 include those compounds of formula A-IX, i.e., compounds of formula A-1-1 wherein

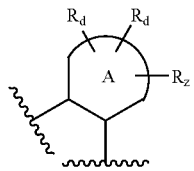

is a 5 or 6 membered heteroaryl group.

Preferred compounds of formula A-IX include compounds of formula A-IX-1, i.e., compounds of formula A-IX wherein $R_2$ and $R_3$ are independently selected from H; $C_1$-$C_6$ alkyl optionally substituted with 1, 2, or 3 substituents that are independently selected from $C_1$-$C_4$ alkyl, halogen, —$CF_3$, and $C_1$-$C_4$ alkoxy; $C_2$-$C_6$ alkenyl or $C_2$-$C_6$ alkynyl wherein each is optionally substituted with one, two, or three substituents selected from —F, —Cl, —OH, —SH, —C≡N, —$CF_3$, $C_1$-$C_3$ alkoxy, and —$NR_5R_6$; or $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein $R_7$ is selected from H; —$C_1$-$C_4$ alkyl optionally substituted with 1, 2, or 3 groups independently selected from —OH, —$NH_2$, and halogen; —$C_3$-$C_8$ cycloalkyl; —($C_1$-$C_4$ alkyl)-O—($C_1$-$C_4$ alkyl); —$C_2$-$C_4$ alkenyl; and —$C_2$-$C_4$ alkynyl.

Preferred compounds of formula A-IX-1 include those of formula A-IX-2, i.e., compounds of formula A-IX-1, wherein $R_{15}$ at each occurrence is independently selected from hydrogen, $C_1$-$C_4$ alkyl, $C_1$-$C_6$ alkanoyl, benzyl optionally substituted with $OCH_3$, —C(O)-tertiary butyl, and —$CO_2$-benzyl.

Preferred compounds of formula A-IX-2 include those of formula A-IX-3, i.e., compounds of formula A-IX-2, wherein $R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino OC(=O)-mono- and dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, $CF_3$, $OCF_3$, $C_1$-$C_4$ alkoxy, amino, and mono- or dialkylamino; or $R_1$ is aryl, heteroaryl, heterocyclyl, aryl $C_1$-$C_6$ alkyl, heteroaryl $C_1$-$C_6$ alkyl, or heterocycloalkyl $C_1$-$C_6$ alkyl;

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—($C_1$-$C_4$ alkyl), —$CO_2$—($C_1$-$C_4$ alkyl), —$SO_2$—$NR_5R_6$, —$NR_7R_8$, —CO—$NR_5R_6$, —CO—$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_4$ haloalkyl, $C_1$-$C_4$ haloalkoxy, phenyl, $NR_7R_8$, and $C_1$-$C_4$ alkoxy.

Preferred compounds of formula A-IX-3 include those of formula A-IX-4, i.e., compounds of formula A-IX-3, wherein $R_{50}$ at each occurrence is independently selected from halogen, OH, SH, —$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_4$ haloalkyl, $C_1$-$C_4$ haloalkoxy, phenyl, $NR_7R_8$, and $C_1$-$C_4$ alkoxy.

Preferred compounds of formula A-IX-4 include those of formula A-IX-5, i.e., compounds of formula A-X-4, of the formula

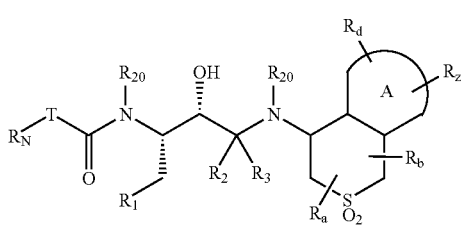

A-IX-5 wherein

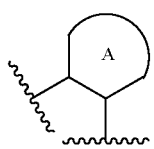

is selected from pyridinyl, pyrimidinyl, imidazolyl, oxazolyl, thiazolyl, furanyl, thienyl, pyrazole, isoxazole, and pyrrolyl.

Preferred compounds of formula A-IX-5 include compounds of formula A-IX-6, i.e., compounds of formula A-IX-5 wherein wherein, $R_1$ is phenyl $C_1$-$C_6$ alkyl or naphthyl $C_1$-$C_6$ alkyl, wherein the phenyl or naphthyl group is optionally substituted with 1, 2, 3, 4, or 5 $R_{50}$ groups.

Preferred compounds of formula A-IX-6 include compounds of formula A-IX-7, i.e., compounds of formula A-IX-6 wherein $R_2$, $R_3$ and the carbon to which they are attached form a carbocycle of three thru six carbon atoms, wherein one carbon atom is optionally replaced by a group selected from —O—, —S—, —SO$_2$—, or —NR$_7$—; wherein $R_7$ is H, —$C_1$-$C_8$ alkyl optionally substituted with 1, 2, or 3 groups independently selected from —OH, —NH$_2$, and halogen; —$C_2$-$C_4$ alkenyl; or —$C_2$-$C_4$ alkynyl.

Preferred compounds of formula A-IX-7 include compounds of formula A-IX-8, i.e., compounds of formula A-IX-7 wherein $R_2$, $R_3$ and the carbon to which they are attached form a carbocycle of three thru six carbon atoms.

Other preferred compounds of formula A-IX-7 include compounds of formula A-IX-9, i.e., compounds of formula A-IX-7 wherein $R_2$, $R_3$ and the carbon to which they are attached form a heterocycloalkyl group containing 2 to 5 carbon atoms and one group selected from —O—, —S—, —SO$_2$—, and —NR$_7$—; wherein $R_7$ is H, —$C_1$-$C_6$ alkyl optionally substituted with 1, 2, or 3 groups independently selected from —OH, —NH$_2$, and halogen; —$C_2$-$C_4$ alkenyl; or —$C_2$-$C_4$ alkynyl.

Other preferred compounds of formula A-IX-6 include compounds of formula A-IX-10, i.e., compounds of formula A-IX-6 wherein $R_2$ and $R_3$ are independently selected from H; $C_1$-$C_4$ alkyl optionally substituted with 1 substituent that is selected from halogen, —CF$_3$, and $C_1$-$C_4$ alkoxy; $C_2$-$C_4$ alkenyl; $C_2$-$C_4$ alkynyl; and —CO$_2$—($C_1$-$C_4$ alkyl); and $R_5$ and $R_6$ are at each occurrence are independently H or $C_1$-$C_6$ alkyl; or $R_5$ and $R_6$ and the nitrogen to which they are attached, at each occurrence form a 5 or 6 membered heterocycloalkyl ring.

Preferred compounds of formulas A-IX-8, A-IX-9, or A-IX-10 include those of formula A-IX-11, i.e., compounds of formulas A-IX-8, A-IX-9, or A-IX-10 wherein $R_a$ and $R_b$ are independently selected from $C_1$-$C_6$ alkyl, $C_1$-$C_6$ alkoxy, halogen, CN, OH, hydroxyalkyl, $C_1$-$C_6$ haloalkyl, $C_1$-$C_6$ haloalkoxy, and —$C_1$-$C_6$ alkyl-NR$_5$R$_6$; or $R_a$ and $R_b$ are attached to the same carbon and form a $C_3$-$C_7$ spirocycle; and $R_{20}$ at each occurrence is independently H or $C_1$-$C_4$ alkyl.

Preferred compounds of formula A-IX-11 include those wherein

Rz and $R_d$ are independently selected from $C_1$-$C_6$ alkyl optionally substituted with one, two or three substituents selected from $C_1$-$C_3$ alkyl, halogen, OH, SH, C≡N, CF$_3$, $C_1$-$C_3$ alkoxy, and —NR$_5$R$_6$; hydroxy; halogen; $C_2$-$C_6$ alkenyl or $C_2$-$C_6$ alkynyl, wherein the alkenyl or alkynyl group is optionally substituted with $C_1$-$C_4$ alkyl, halogen, hydroxy, SH, cyano, CF$_3$, $C_1$-$C_4$ alkoxy, or NR$_5$R$_6$.

Other preferred compounds of formula A-IX-11 include those wherein

Rz and $R_d$ are —(CH$_2$)$_{0-4}$—CO—NR$_{21}$R$_{22}$, —(CH$_2$)$_{0-4}$—SO$_2$—NR$_{21}$R$_{22}$; —(CH$_2$)$_{0-4}$—SO—(C$_1$-C$_8$ alkyl); —(CH$_2$)$_{0-4}$—SO$_2$—(C$_1$-C$_{12}$ alkyl); —(CH$_2$)$_{0-4}$—SO$_2$—(C$_3$-C$_7$ cycloalkyl); —(CH$_2$)$_{0-4}$—N(H or R$_{20}$)—CO—O—R$_{20}$; —(CH$_2$)$_{0-4}$—N(H or R$_{20}$)—CO—N(R$_{20}$)$_2$; —(CH$_2$)$_{0-4}$—N—CS—N(R$_{20}$)$_2$; —(CH$_2$)$_{0-4}$—N(—H or R$_{20}$)—CO—R$_{21}$; or —(CH$_2$)$_{0-4}$-NR$_{21}$R$_{22}$; wherein $R_{21}$ and $R_{22}$ independently represent hydrogen, $C_1$-$C_6$ alkyl, hydroxyl($C_1$-$C_6$)alkyl, amino($C_1$-$C_6$)alkyl, haloalkyl, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, phenyl, naphthyl, or heteroaryl;

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Still other preferred compounds of formula A-IX-11 include those wherein $R_z$ and $R_d$ are —(CH$_2$)$_{0-4}$—CO—(C$_1$-C$_{12}$ alkyl); —(CH$_2$)$_{0-4}$—CO—(C$_2$-C$_{12}$ alkenyl); CH$_2$)$_{0-4}$—CO—(C$_2$-C$_{12}$) alkynyl; —(CH$_2$)$_{0-4}$—CO—(C$_3$-C$_7$ cycloalkyl); —(CH$_2$)$_{0-4}$—CO-phenyl; —(CH$_2$)$_{0-4}$—CO-naphthyl; —(CH$_2$)$_{0-4}$—CO-heteroaryl; —(CH$_2$)$_{0-4}$—CO-heterocycloalkyl; —(CH$_2$)$_{0-4}$—CO$_2$R$_{60}$; where $R_{60}$ is selected from $C_1$-$C_6$ alkyl, —(CH$_2$)$_{0-2}$-(phenyl), —(CH$_2$)$_{0-2}$-(naphthyl), $C_2$-$C_6$ alkenyl, $C_2$-$C_6$ alkynyl, $C_3$-$C_7$ cycloalkyl, —(CH$_2$)$_{0-2}$-(heterocycloalkyl) and —(CH$_2$)$_{0-2}$-(heteroaryl);

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Yet still other preferred compounds of formula A-IX-11 include those wherein

Rz and $R_d$ are —(CH$_2$)$_{0-4}$—O—CO—(C$_1$-C$_6$ alkyl); —(CH$_2$)$_{0-4}$—O—P(O)—(OR$_5$)$_2$; —(CH$_2$)$_{0-4}$—O—CO—N(R$_{20}$)$_2$; —(CH$_2$)$_{0-4}$—O—CS—N(R$_{20}$)$_2$; —(CH$_2$)$_{0-4}$—O—(R$_{20}$); —(CH$_2$)$_{0-4}$—O—(R$_{20}$)—CO$_2$H; —(CH$_2$)$_{0-4}$-S—(R$_{20}$); —(CH$_2$)$_{0-4}$—O-halo(C$_1$-C$_6$)alkyl; —(CH$_2$)$_{0-4}$—O—(C$_1$-C$_6$)alkyl; $C_3$-$C_8$ cycloalkyl; or —(CH$_2$)$_{0-4}$—N(—H or R$_{20}$)—SO$_2$—R$_{21}$; wherein each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—(C$_1$-C$_4$ alkyl), —CO$_2$—(C$_1$-C$_4$ alkyl), —SO$_2$—NR$_5$R$_6$, —NR$_7$R$_8$, —CO—NR$_5$R$_6$, —CO—NR$_7$R$_8$, —SO$_2$—(C$_1$-C$_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_6$ haloalkyl, $C_1$-$C_6$ haloalkoxy, phenyl, $NR_7R_8$, and $C_1$-$C_6$ alkoxy.

Other preferred compounds of formula A-IX-5 include those of formula A-IX-12, i.e., compounds of formula A-IX-5, wherein $R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino and —OC(=O)-mono- or dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, $CF_3$, $OCF_3$, $C_1$-$C_4$ alkoxy, amino, and mono- or dialkylamino.

Preferred compounds of formula A-IX-12, include those of formula A-IX-13, i.e., compounds of formula A-IX-12 wherein $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein $R_7$ is selected from H or —$C_1$-$C_4$ alkyl optionally substituted with 1 group selected from —OH, —$NH_2$, and halogen.

Preferred compounds of formula A-IX-13, include those of formula A-IX-14, i.e., compounds of formula A-IX-13 wherein $R_2$, $R_3$ and the carbon to which they are attached form a carbocycle of three thru six carbon atoms.

Other preferred compounds of formula A-IX-13, include those of formula A-IX-15, i.e., compounds of formula A-IX-13 wherein $R_2$, $R_3$ and the carbon to which they are attached form a heterocycloalkyl group containing 2 to 5 carbon atoms and one group selected from —O—, —S—, —$SO_2$—, and —$NR_7$—; wherein $R_7$ is selected from H and —$C_1$-$C_4$ alkyl optionally substituted with 1 group selected from —OH, —$NH_2$, and halogen.

Other preferred compounds of formula A-IX-13, include those of formula A-IX-16, i.e., compounds of formula A-IX-13 wherein $R_2$ and $R_3$ are independently selected from H; $C_1$-$C_4$ alkyl optionally substituted with 1 substituent that is selected from halogen, —CF3, $C_1$-$C_4$ alkoxy; $C_2$-$C_4$ alkenyl; and $C_2$-$C_4$ alkynyl; and $R_5$ and $R_6$ are at each occurrence are independently —H or $C_1$-$C_6$ alkyl; or $R_5$ and $R_6$ and the nitrogen to which they are attached, at each occurrence form a 5 or 6 membered heterocycloalkyl ring.

Preferred compounds of formulas A-IX-14, A-IX-15, A-IX-16 include compounds of formula A-IX-17, i.e., compounds of formulas A-IX-14, A-IX-15, A-IX-16 wherein $R_a$ and $R_b$ are independently selected from $C_1$-$C_3$ alkyl, F, OH, SH, C≡N, $CF_3$, $C_1$-$C_6$ alkoxy, and —$NR_5R_6$; and $R_{15}$ at each occurrence is independently H or $C_1$-$C_4$ alkyl.

Preferred compounds of formula A-IX-17, include those compounds wherein

Rz and $R_d$ are independently selected from $C_1$-$C_6$ alkyl optionally substituted with one, two or three substituents selected from $C_1$-$C_3$ alkyl, halogen, OH, SH, C≡N, $CF_3$, $C_1$-$C_3$ alkoxy, and —$NR_5R_6$; hydroxy; halogen; $C_2$-$C_6$ alkenyl or $C_2$-$C_6$ alkynyl, wherein the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$.

Other preferred compounds of formula A-IX-17, include those compounds wherein

Rz and $R_d$ are —$(CH_2)_{0-4}$—CO—$NR_{21}R_{22}$, —$(CH_2)_{0-4}$—$SO_2$—$NR_{21}R_{22}$; —$(CH_2)_{0-4}$—SO—$(C_1$-$C_8$ alkyl); —$(CH_2)_{0-4}$—$SO_2$—$(C_1$-$C_{12}$ alkyl); —$(CH_2)_{0-4}$—$SO_2$—$(C_3$-$C_7$ cycloalkyl); —$(CH_2)_{0-4}$—N(H or $R_{20}$)—$CO_2R_{20}$; —$(CH_2)_{0-4}$—N(H or $R_{20}$)—CO—$N(R_{20})_2$; —$(CH_2)_{0-4}$—N—CS—$N(R_{20})_2$; —$(CH_2)_{0-4}$—N(—H or $R_{20}$)—CO—$R_{21}$; or —$(CH_2)_{0-4}$—$NR_{21}R_{22}$; wherein $R_{21}$ and $R_{22}$ independently represent hydrogen, $C_1$-$C_6$ alkyl, hydroxyl $(C_1$-$C_6)$alkyl, amino$(C_1$-$C_6)$alkyl, haloalkyl, $C_3$-$C_7$ cycloalkyl, —$(C_1$-$C_2$ alkyl)-$(C_3$-$C_7$ cycloalkyl), —$(C_1$-$C_6$ alkyl)-O—$(C_1$-$C_3$ alkyl), —$C_2$-$C_6$ alkenyl, —$C_2$-$C_6$ alkynyl, phenyl, naphthyl, or heteroaryl;

each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Still other preferred compounds of formula A-IX-17, include those compounds wherein Rz and $R_d$ are —$(CH_2)_{0-4}$—CO—$(C_1$-$C_{12}$ alkyl); —$(CH_2)_{0-4}$—CO—$(C_2$-$C_{12}$ alkenyl); $(CH_2)_{0-4}$—CO—$(C_2$-$C_{12})$ alkynyl; —$(CH_2)_{0-4}$—CO—$(C_3$-$C_7$ cycloalkyl); —$(CH_2)_{0-4}$—CO-phenyl; —$(CH_2)_{0-4}$—CO-naphthyl; —$(CH_2)_{0-4}$—CO-heteroaryl; —$(CH_2)_{0-4}$—CO-heterocycloalkyl; —$(CH_2)_{0-4}$—$CO_2R_{20}$; where $R_{20}$ is selected from $C_1$-$C_6$ alkyl, —$(CH_2)_{0-2}$-(phenyl), —$(CH_2)_{0-2}$-(naphthyl), $C_2$-$C_6$ alkenyl, $C_2$-$C_6$ alkynyl, $C_3$-$C_7$ cycloalkyl, —$(CH_2)_{0-2}$-(heterocycloalkyl) and —$(CH_2)_{0-2}$-(heteroaryl);

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Yet still other preferred compounds of formula A-IX-17, include those compounds wherein Rz and $R_d$ are —$(CH_2)_{0-4}$—O—CO—$(C_1$-$C_6$ alkyl); —$(CH_2)_{0-4}$—O—P(O)—$(OR_5)_2$; —$(CH_2)_{0-4}$—O—CO—N$(R_{20})_2$; —$(CH_2)_{0-4}$—O—CS—$N(R_{20})_2$; —$(CH_2)_{0-4}$—O—$(R_{20})$; —$(CH_2)_{0-4}$—O—$(R_{20})$—$CO_2H$; —$(CH_2)_{0-4}$—S—$(R_{20})$; —$(CH_2)_{0-4}$—O-halo$(C_1$-$C_6)$alkyl; —$(CH_2)_{0-4}$—O—$(C_1$-$C_6)$alkyl; $C_3$-$C_8$ cycloalkyl; or —$(CH_2)_{0-4}$—N(—H or $R_{20}$)—$SO_2$—$R_{21}$; wherein each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—($C_1$-$C_4$ alkyl), —CO$_2$—($C_1$-$C_4$ alkyl), —SO$_2$—$NR_5R_6$, —$NR_7R_8$, —CO—$NR_5R_6$, —CO—$NR_7R_8$, —SO$_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_6$ haloalkyl, $C_1$-$C_6$ haloalkoxy, phenyl, $NR_7R_8$, and $C_1$-$C_6$ alkoxy.

Other preferred compounds of formula A-IX-4 include those of formula A-X

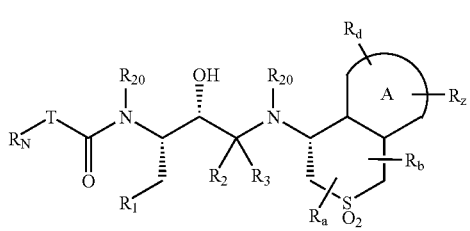

A-X

Preferred compounds of formula A-X include compounds of formula A-X-1, i.e., compounds of formula A-X wherein $R_1$ is phenyl $C_1$-$C_6$ alkyl or naphthyl $C_1$-$C_6$ alkyl, wherein the phenyl or naphthyl group is optionally substituted with 1, 2, 3, 4, or 5 $R_{50}$ groups; and $R_2$ and $R_3$ are independently H or $C_1$-$C_4$ alkyl.

Preferred compounds of formula A-X-1 include compounds of formula A-X-2, i.e., compounds of formula A-X-1 wherein $R_a$ and $R_b$ are independently H or $C_1$-$C_4$ alkyl; or $R_a$ and $R_b$ are attached to the same carbon and form a $C_3$-$C_6$ carbocycle;

$R_1$ is phenyl, optionally substituted with 1, 2, or 3 $R_{50}$ groups; and $R_{20}$ at each occurrence is independently H or $C_1$-$C_4$ alkyl.

Preferred compounds of formula A-X-2 include compounds of formula A-X-3, i.e., compounds of formula A-X-2 wherein $R_1$ is a dihalophenyl.

Preferred compounds according to any one of formulas A-IX-5, A-X or A-X-3 include compounds of formula A-X-4, i.e., compounds according to any one of formulas A-IX-5, A-X or A-X-3 having the following structure,

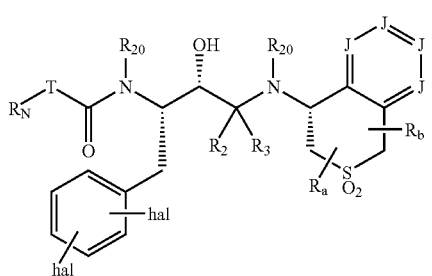

A-X-4 wherein

J at each occurrence is independently selected from N or CRz, wherein

Rz at each occurrence is independently selected from $C_1$-$C_6$ alkyl, optionally substituted with 1, 2, or 3 substituents independently selected from $C_1$-$C_3$ alkyl, halogen, OH, SH, C≡N, $CF_3$, $C_1$-$C_6$ alkoxy, $C_3$-$C_8$ cycloalkyl, and $NR_5R_6$; hydroxy; halogen; $C_2$-$C_6$ alkenyl or $C_2$-$C_6$ alkynyl, wherein the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$;

provided that at least two Js are CRz.

Other preferred compounds according to any one of formulas A-IX-5, A-X or A-X-3 include compounds of formula A-X-5, i.e., compounds according to any one of formulas A-IX-5, A-X or A-X-3 having the following structure,

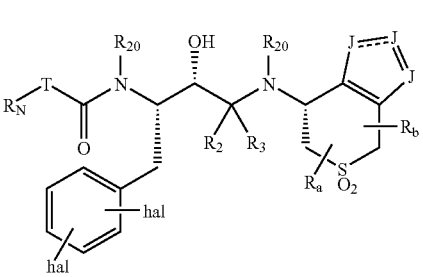

A-X-5 wherein

—represents a single or double bond, provided that only one of the dashed bonds is a double bond;

J is selected from N, S, O, and CRz, wherein

Rz at each occurrence is independently selected from $C_1$-$C_6$ alkyl, optionally substituted with 1, 2, or 3 substituents independently selected from $C_1$-$C_3$ alkyl, halogen, OH, SH, C≡N, $CF_3$, $C_1$-$C_6$ alkoxy, $C_3$-$C_8$ cycloalkyl, and $NR_5R_6$; hydroxy; halogen; $C_2$-$C_6$ alkenyl or $C_2$-$C_6$ alkynyl, wherein the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$;

provided that at least one J is CRz.

Other preferred compounds include those compounds according to any one of embodiments A-I to A-X-5, wherein T is oxygen, NH, N-methyl, or N-ethyl.

Still other preferred compounds include those compounds according to any one of embodiments A-I to A-X-5, wherein $R_5$ and $R_6$ at each occurrence are independently H or $C_1$-$C_4$ alkyl. In another aspect, the invention provides a method of preparing compounds of formula.

In another aspect, the invention provides intermediates that are useful in the preparation of the compounds of interest.

In other aspects of Formula I, $R_C$ is tetralinyl, indanyl, chromanyl, isochromanyl or a cylic or bi-cyclic sulfonyl, or an optionally substituted derivative thereof. Optional substitutents include, for example, $C_{1-6}$ alkyl, $C_{1-6}$ haloalkyl, $C_{4-7}$ cycloalkyl, —OH, —$NH_2$ or a halogen (e.g., F, Br, I, Cl). Generally speaking, $R_C$ may be attached at any point on the tetraline, indane or cyclic or bi-cyclic sulfone ring system, provide that the valancy requirements for the atom of the ring system at the point of attachment are satisfied.

In a futher preferred aspect of Formula I, X is —N($R_{20}$)—C(=O)— or —O—(C=O)—. In another preferred embodiment of formula I, X is —N($R_{20}$)—C(=O)— or —O—(C=O)—, and $R_C$ is tetralinyl, indanyl, chromanyl, isochromanyl or a cylic or bi-cyclic sulfonyl group, or an optionally substituted derivative thereof. Optional substitutents include, for example, $C_{1-6}$ alkyl, $C_{1-6}$ haloalkyl, $C_{4-7}$ cycloalkyl, —OH, —$NH_2$ or a halogen (e.g., F, Br, I, Cl). Generally speaking, $R_C$ may be attached at any point on the tetraline, indane or cyclic or bi-cyclic sulfone ring system, provide that the valancy requirements for the atom of the ring system at the point of attachment are satisfied.

In another preferred embodiment of formula I, X is —(C=O)— and T is $NR_{20}$ or O.

In a further preferred embodiment of formula I, X is —(C=O)— and T is O.

In a yet further preferred embodiment of formula I, X is —(C=O)— and T is —N—H.

With respect to Rc, aromatic rings, which are also referred to herein as aryl or aryl rings, are preferably those unsaturated carbocylic rings that have a particularly stable electronic configuration owing to resonance (delocalization) of the pi-bond electrons in their structure. Those carbon-only rings having a delocalized (4n+2) pi-electron system (this predictor is known as Huckel's rule of 4n+2, where n is 0 or an integer) in a planar or substantially planar ring system. Thus, by way of non-limiting example, benzene, naphthalene and azulene are aromatic rings, as are phenanthrene and anthracene. For further discussion of aromaticity see, for example, Fessenden R J, and Fessenden J S, 1990 Organic Chemistry, 4th ed., Brooks/Cole Publishing Company, Pacific Grove, Calif. For the purposes of the present invention this definition excludes charged aromatic compounds such as cyclopentadienyl anion and cyclopropyl cation. Preferred rings sizes are: 6 atoms for a monocyclic aromatic ring; 10 for a bicyclic ring and 14 for a tricyclic aromatic ring system.

With respect to Rc, heteroaromatic rings, which are also referred to herein as heteroaryl or heteroaryl rings, are preferably those ring systems that consist of carbon and at least one heteratom selected from oxygen, nitrogen and sulfur. Heteroaromatics are formally derived from aryl rings by replacement of one or more methine (—C=) and/or vinylene (—CH=CH—) groups by trivalent or divalent heteroatoms, respectively, in such a way as to maintain the continuous pi-electron system characteristic of aromatic systems and a number of out-of-plane pi-electrons corresponding to the Hückel rule (4n+2). For further discussion of heteroaromaticity see: *Comprehensive Heterocyclic Chemistry*, Vol. 1, Ed. O. Meth-Cohn, Pergamon, 1984, p. 3 et seq. Thus, owing to the contribution of out-of-plane pi-electrons, not only are pyridine and pryimidine heteroaryl rings, but also furan, pyrrole, thiophene and imidazole. Examples of multi-ring heteroaryls are those ring systems that contain at least one heteratom in each ring. Thus, by way of non-limiting example, napthyridine, indolizine, thiazole, isoxazole, pteridine, pyrazolo[1,5-a]pyrimidine and thieno[2,3-b]furan are all muticyclic heteroaryl compounds. N-oxides of nitrogen containing heteroaromatics are also contemplated by this definition. Preferred rings sizes are: 5 to 6 atoms for a monocyclic heteroaryl; 8 to 10 for a bicyclic ring and 11 to 14 for a tricyclic ring system.

With respect to Rc, cycloakyl rings, also referred to herein as carbocyles or carbocyclic rings, are preferably those carbon-only containing rings that may contain one to three rings in the cyclic system. These cycloalkyl rings may be saturated or unsaturated, but may not contain a 4n+2 delocalized pi-electron system as described above. Preferred rings sizes are: 5 to 8 carbon atoms for a monocyclic cycloalkyl; 6 to 11 for a bicyclic ring and 8 to 15 for a tricyclic ring system. Non-limiting examples of cycloalkyl are cyclohexane, cylcohexene, cyclopentadiene, decalin, quinone, norbornene, 2,3,6,7-tetrahydrofluorene and [2.2.2] bicyclo-octane With respect to Rc, heterocyclic rings, also referred to herein as heterocyles or heterocyclics, are preferably those ring systems that contain carbon and at least one heteroatom chosen from nitrogen, oxygen or sulfur within the ring chain and which may contain one to three rings in the cyclic system, provided that each of the fused rings contains at least one heteroatom. These heterocycles rings may be saturated or unsaturated, but may not contain a 4n+2 delocalized pi-electron system as described above in the definition of heteroaromatic rings. Preferred rings sizes are: 5 to 8 atoms for a monocyclic heterocycle; 6 to 11 for a bicyclic ring and 8 to 15 for a tricyclic heterocyclic ring system. Non-limiting examples of heterocyclics are pyrrolidine, tetrahydrofuran, dihydrothiophene, thiazoline, thiazolidine, 2,3,8,9-tetrahydropurine, piperazine, 2,3, or 4-pyridone, 5-thia-1-azabicyclo[4.2.0]oct-2-ene, and 1-azabicyclo[2.2.2]octane. Also within the scope of this definition are N-oxides, sulfoxides and sulfones formed from the ring nitrogen or sulfur.

With respect to Rc, aromatic, heteroaromatic, cycloalkyl and heterocyclic rings may be fused to one another to form fused ring systems, provided that fusion of the rings does not result in a structure that exceeds the valence of each of the constituent ring atoms (such as tertiary oxygen) and further does not result in a charged ring atom or delocalized charged species, such as a quaternary ring nitrogen. Non-limiting examples of such combinations are: quinoline (formed by fusion of aromatic and heteroaromatic rings); indane (formed by fusion of aromatic and cycloalkyl rings); 3,4-dihydroquinazoline (formed by fusion of an aromatic and a heterocyclic ring) and hexahydro-indole (formed by fusion of heterocyclic and carbocyclic rings). Additionally, fused tricyclic rings formed by several types of rings are contemplated, for example: phenothizaine (formed by combination of two aromatic and one heterocyclic rings).

In yet another preferred embodiment, the invention encompasseses intermediates of having the formula:

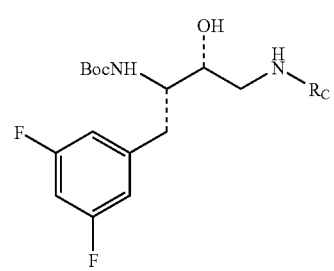

where $R_C$ is as defined above for formula IA.

In a preferred aspect of the intermediates of the invention there is provided a compound of the formula:

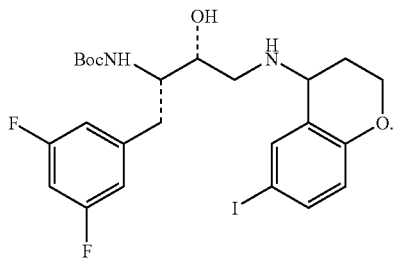

The invention encompasses a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment which comprises administration of a therapeutically effective amount of a compound selected from the group consisting of a compound of formula I or IA, or a pharmaceutically acceptable salt or ester thereof, wherein X, T, $R_{20}$, $R_1$, $R_2$, $R_3$, $R_N$ and $R_C$ are as defined as above.

Preferably, the patient is a human. More preferably, the disease is Alzheimer's disease. More preferably, the disease is dementia.

The invention includes methods for making compounds of formula I and IA.

The compounds of formula I and IA are made by methods well known to those skilled in the art from starting compounds known to those skilled in the art. The process chemistry is well known to those skilled in the art. The most general process to prepare compounds of formula I and IA of the invention is set forth in Scheme 1. One skilled in the art will appreciate that these are all wellknown reactions in organic chemistry. A chemist skilled in the art, knowing the chemical structure of the biologically end product of formula I and IA of the invention would be able to prepare them by known methods from known starting materials without any additional information. The explanation below therefore is not necessary but is deemed helpful to those skilled in the art who desire to make the compounds of the invention.

Scheme I sets forth a general method used in the invention to prepare the appropriate compounds of formula (I). All reactions were run in 4-ml vials. 0.07 mmol of the starting amine is placed in each reaction vial. Next, 0.28 mmol (4 equiv.) of diisopropylethylamine is added in each vial. 0.077 mmol (1.1 equiv.) of each isocyanate or chloroformate is then added into the reaction vial. Finally, the starting reagents are dissolved in 1.5 ml of dichloromethane. Each reaction was run overnight at room temperature. LC/MS analysis for each reaction was performed via an Agilent 1100 HPLC, utilizing a Thermo-Hypersil C18 50×3 mm 5 micron column, coupled to a Thermo-Finnigan LCQ MS. Final purification of each product was performed via a Varian Pro Star Preparative HPLC utilizing a Phenomenex C18 60×21.2 mm 5 micron column.

Scheme I

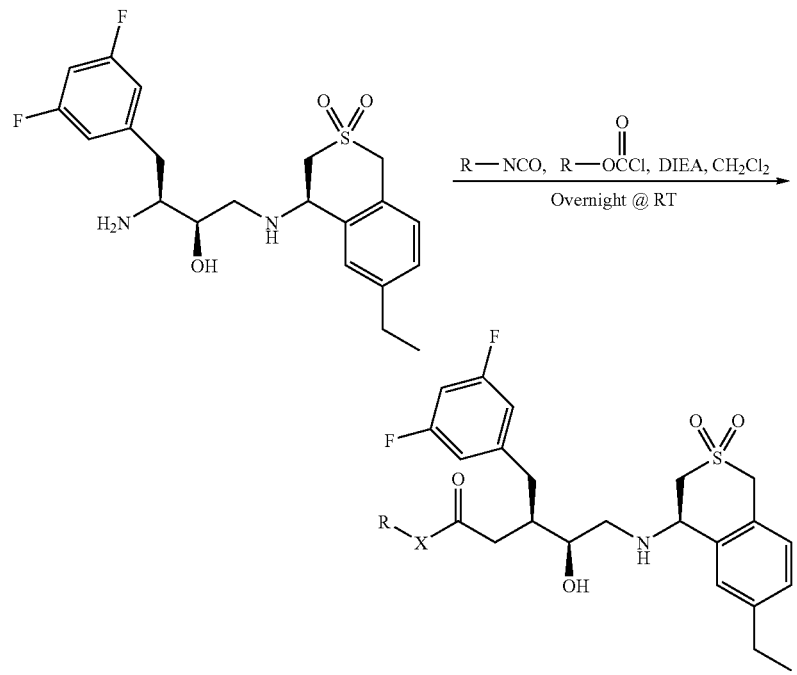

Alternatively, scheme II sets forth a general method to prepare appropriate compounds of formula (I). A protected amine is reacted with phosgene or phosgene equivalent such as triphosgene to generate an isocyanate that is subsequently reacted with an appropriate nucleophile. Finally, removal of the protecting group and purification by preparative HPLC will provide amines of formula (I).

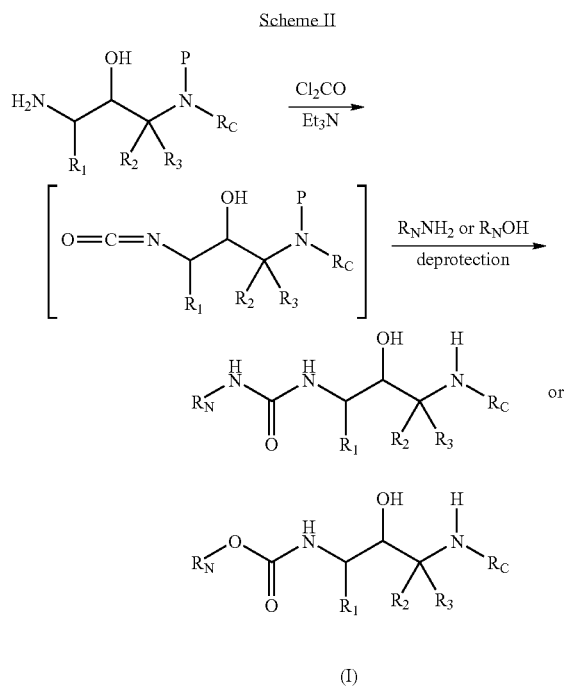

When an amino protecting group is used when preparing the inventive compounds, but no longer needed, it is removed by methods well known to those skilled in the art. By definition the amino protecting group must be readily removable as is known to those skilled in the art by methods well known to those skilled in the art. Suitable amino protecting group is selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl) prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino) ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl and 1-piperidyloxycarbonyl, 9-fluorenylmethyl carbonate, —CH—CH═CH$_2$ and phenyl-C(═N—)—H.

Suitable means for removal of the amine-protecting group depends on the nature of the protecting group. Those skilled in the art, knowing the nature of a specific protecting group, know which reagent is preferable for its removal. For example, it is preferred to remove the preferred protecting group, BOC, by dissolving the protected material in a trifluoroacetic acid/dichloromethane mixture.

Certain transformations can be carried out to generate desired $R_C$ groups after the $R_N$ group is placed in the molecule. Further, certain of these transformations can be carried out after the protecting group P is removed.

The compounds of the invention may contain geometric or optical isomers as well as tautomers. Thus, the invention includes all tautomers and pure geometric isomers, such as the E and Z geometric isomers, as well as mixtures thereof. Futhermore, the invention includes pure enantiomers and diasteriomers as well as mixtures thereof, including racemic mixtures. The individual geometric isomers, enantiomers, or diasteriomers may be prepared or isolated by methods known in the art.

Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.*, 33, 201-217 (1986) and *J. Pharm. Sci.*, 66(1), 1, (1977).

The invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

METHODS OF THE INVENTION

The compounds of the invention, and pharmaceutically acceptable salts thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the invention are useful when administered to a patient who has not been diagnosed as possibly having the disease at the time of administration, but who would normally be expected to develop the disease or be at increased risk for the disease.

The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds of the invention may be started before symptoms appear, and treatment may be continued indefinitely to prevent or delay the outset of the disease.

Dosage Forms and Amounts

The compounds of the invention can be administered orally, parenternally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenternal administration. Typically the compounds described above are formulated into pharmaceutical compositions using techniques and procedures well known in the art.

About 1 to 500 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenternally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenternally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

In an embodiment, this method of treatment can employ therapeutically effective amounts: for oral administration from about 0.1 mg/day to about 3,000, preferably about 1,000 mg/day; for parenteral, sublingual, intranasal, intrathecal administration from about 0.5 to about 500 mg/day, preferably about 100 mg/day; for depo administration and implants from about 0.5 mg/day to about 50 mg/day; for topical administration from about 0.5 mg/day to about 200 mg/day; for rectal administration from about 0.5 mg to about 500 mg. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenternal dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

The invention here is the new compounds of the invention and new methods of using the compounds of the invention. Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, *Arch. Neurol.* 57:454), and other neurotropic agents of the future.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744, 346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et. al., 1999, Mol. Cell. Neurosci. 14:419-427; Vassar et. al., 1999, Science 286:735-741; Yan et. al., 1999, Nature 402:533-537; Sinha et. al., 1999, Nature 40:537-540; and Lin et. al., 2000, PNAS USA 97:1456-1460). Synthetic forms of the enzyme have also been described (WO98/22597 and WO00/17369). Beta-secretase can be extracted and purified from human brain tissue and can be produced in cells, for example mammalian cells expressing recombinant enzyme.

Preferred compounds are effective to inhibit 50% of beta-secretase enzymatic activity at a concentration of less than about 50 micromolar, preferably at a concentration of less than about 10 micromolar, more preferably less than about 1 micromolar, and most preferably less than about 10 nanomolar.

APP Substrate

Assays that demonstrate inhibition of beta-secretase-mediated cleavage of APP can utilize any of the known forms of APP, including the 695 amino acid "normal" isotype described by Kang et. al., 1987, Nature 325:733-6, the 770 amino acid isotype described by Kitaguchi et. al., 1981, Nature 331:530-532, and variants such as the Swedish Mutation (KM670-1NL) (APP-SW), the London Mutation (V7176F), and others. See, for example, U.S. Pat. No. 5,766,846 and also Hardy, 1992, Nature Genet. 1:233-234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Pirttila et. al., 1999, Neuro. Lett. 249:21-4, and in U.S. Pat. No. 5,612,486. Useful antibodies to detect A beta include, for example, the monoclonal antibody 6E10 (Senetek, St. Louis, Mo.) that specifically recognizes an epitope on amino acids 1-16 of the A beta peptide; antibodies 162 and 164 (New York State Institute for Basic Research, Staten Island, N.Y.) that are specific for human A beta 1-40 and 1-42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744, 346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. No. 5,942,400 and 5,744,346. Such assays can be performed in cell-free incubations or in cellular incubations using cells expressing a beta-secretase and an APP substrate having a beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4-7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399; 5,612,486; 5,387,742; 5,720,936; 5,850,003; 5,877,015, and 5,811,633, and in Ganes et. al., 1995, Nature 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Unless defined otherwise, all scientific and technical terms used herein have the same meaning as commonly understood by one of skill in the art to which this invention belongs. All patents and publications referred to herein are hereby incorporated by reference for all purposes.

Definitions and Conventions

The definitions and explanations below are for the terms as used throughout this entire document including both the specification and the claims.

Definitions

All temperatures are in degrees Celsius.

TLC refers to thin-layer chromatography.

psi refers to pounds/in$^2$.

HPLC refers to high pressure liquid chromatography.

THF refers to tetrahydrofuran.

DMF refers to dimethylformamide.

EDC refers to ethyl-1-(3-dimethylaminopropyl)carbodiimide or 1-(3-dimethylaminopropyl)-3-ethylcarbodiimide hydrochloride.

HOBt refers to 1-hydroxy benzotriazole hydrate.

NMM refers to N-methylmorpholine.

NBS refers to N-bromosuccinimide.

TEA refers to triethylamine.

BOC refers to 1,1-dimethylethoxy carbonyl or t-butoxycarbonyl, represneted schematically as-CO—O—C(CH$_3$)$_3$.

CBZ refers to benzyloxycarbonyl, —CO—O—CH$_2$-φ.

FMOC refers to 9-fluorenylmethyl carbonate.

TFA refers to trifluoracetic acid, CF$_3$—COOH.

CDI refers to 1,1'-carbonyldiimidazole.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (d) downfield from TMS.

IR refers to infrared spectroscopy.

-phenyl refers to phenyl (C$_6$H$_5$).

MS refers to mass spectrometry expressed as m/e, m/z or mass/charge unit. MH$^+$ refers to the positive ion of a parent plus a hydrogen atom. EI refers to electron impact. CI refers to chemical ionization. FAB refers to fast atom bombardment.

HRMS refers to high resolution mass spectrometry.

Ether refers to diethyl ether.

When solvent pairs are used, the ratios of solvents used are volume/volume (v/v).

When the solubility of a solid in a solvent is used the ratio of the solid to the solvent is weight/volume (wt/v).

BOP refers to benzotriazol-1-yloxy-tris(dimethylamino) phosphonium hexafluorophosphate.

TBDMSCl refers to t-butyldimethylsilyl chloride.

TBDMSOTf refers to t-butyldimethylsilyl trifluosulfonic acid ester.

Trisomy 21 refers to Down's Syndrome.

APP, amyloid precursor protein, is defined as any APP polypeptide, including APP variants, mutations, and isoforms, for example, as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (BACE1, Asp2, Memapsin 2) is an aspartyl protease that mediates cleavage of APP at the amino-terminal edge of A beta. Human beta-secretase is described, for example, in WO00/17369.

By "alkyl" and "$C_1$-$C_6$ alkyl" in the invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons.

By "alkoxy" and "$C_1$-$C_6$ alkoxy" in the invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the invention is meant fluorine, bromine, chlorine, and iodine.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. For example, such cycloalkyl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, —COOH, —C(=O)O($C_1$-$C_6$ alkyl), —C(=O)$NH_2$, —C(=O)N(mono- or di-$C_1$-$C_6$ alkyl), —S($C_1$-$C_6$ alkyl), —$SO_2$($C_1$-$C_6$ alkyl), —O—C(=O) ($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—$SO_2$—($C_1$-$C_6$ alkyl), —N($C_1$-$C_6$ alkyl)-$SO_2$—($C_1$-$C_6$ alkyl), —NH—C(=O)$NH_2$, —NH—C(=O)N(mono- or di-$C_1$-$C_6$ alkyl), —NH($C_1$-$C_6$ alkyl)-C(=O)—$NH_2$ or —NH($C_1$-$C_6$ alkyl)-C(=O)—N-(mono- or di-$C_1$-$C_6$ alkyl).

By "heteroaryl" is meant one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl, —COOH, —C(=O)O($C_1$-$C_6$ alkyl), —C(=O)$NH_2$, —C(=O)N(mono- or di-$C_1$-$C_6$ alkyl), —S($C_1$-$C_6$ alkyl), —$SO_2$($C_1$-$C_6$ alkyl), —O—C(=O)($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—$SO_2$—($C_1$-$C_6$ alkyl), —N($C_1$-$C_6$ alkyl)-$SO_2$—($C_1$-$C_6$ alkyl), —NH—C(=O)$NH_2$, —NH—C(=O)N(mono- or di-$C_1$-$C_6$ alkyl), —NH($C_1$-$C_6$ alkyl)-C(=O)—$NH_2$ or —NH($C_1$-$C_6$ alkyl)-C(=O)—N-(mono- or di-$C_1$-$C_6$ alkyl).

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. For example, such heterocycle groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl or =O.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

BIOLOGY EXAMPLES

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et. al, 1999, *Nature* 40:537-540) or recombinantly produced as the full-length enzyme (amino acids 1-501), and can be prepared, for example, from 293 cells expressing the recombinant cDNA, as described in WO00/47618. Human brain □-Secretase from concentrated HiQ pool prepared Jul. 16, 1997 in 0.20% Triton was used in the assay. Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure:

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well was transferred to a corresponding anti-MBP antibody coated ELISA plate for capture, containing 80 microliters/well specimen diluent. This reaction is incubated overnight at 4 degrees C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

```
Biotin-SEVNL-DAEFRC[Oregon green]KK      [SEQ ID NO:1]

Biotin-SEVKM-DAEFRC[Oregon green]KK      [SEQ ID NO:2]

Biotin-GLNIKTEEISEISY-EVEFRC             [SEQ ID NO:3]
[Oregon green]KK

Biotin-ADRGLTTRPGSGLTNIKTEEISEVNL-       [SEQ ID NO:4]
DAEFRC
[Oregon green]KK

Biotin-FVNQHLCoxGSHLVEALY-               [SEQ ID NO:5]
LVCoxGERGFFYTPKAC[Oregon green]KK
```

The enzyme (0.1 nanomolar) and test compounds (0.001-100 micromolar) are incubated in pre-blocked, low affinity, black plates (384 well) at 37 degrees for 30 minutes. The reaction is initiated by addition of 150 millimolar substrate to a final volume of 30 microliter per well. The final assay conditions are: 0.001-100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate.

Example C

Beta-Secretase Inhibition: P26-P4'SW Assay

Synthetic substrates containing the beta-secretase cleavage site of APP are used to assay beta-secretase activity, using the methods described, for example, in published PCT application WO00/47618. The P26-P4'SW substrate is a peptide of the sequence: (biotin)CGGADRGLTTRPGS-GLTNIKTEEISEVNLDAEF [SEQ ID NO: 6] The P26-P1 standard has the sequence: (biotin)CGGADRGLTTRPGS-GLTNIKTEEISEVNL [SEQ ID NO: 7].

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with streptavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays Using Synthetic Oligopeptide-Substrates

Synthetic oligopeptides are prepared that incorporate the known cleavage site of beta-secretase, and optionally detectable tags, such as fluorescent or chromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et. al., 1992, *Nature* 360:672-674), as described in U.S. Pat. No. 5,604, 102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et. al., 1995, *Nature* 373:523-527 are useful to analyze in vivo suppression of A beta release in the presence of putative inhibitory compounds. As described in U.S. Pat. No. 6,191, 166, 4 month old PDAPP mice are administered compound formulated in vehicle, such as corn oil. The mice are dosed with compound (1-30 mg/ml; preferably 1-10 mg/ml). After time, e.g., 3-10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

Chemistry Examples

The following detailed examples describe how to prepare various compounds and/or perform various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

N³-[({(1S,2R)-1-(3,5-difluorobenzyl)-2-hydroxy-3-[(3-methoxybenzyl)amino]propyl}amino)carbonyl]-N¹,N¹-dipropyl-beta-alaninamide (Compound 1)

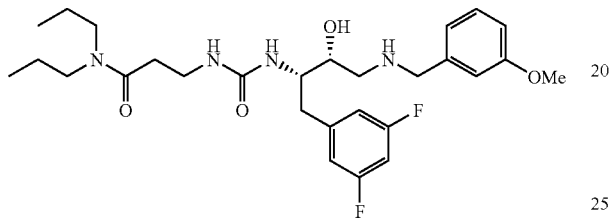

Step 1: [3-tert-butoxycarbonylamino-4-(3,5-difluorophenyl)-2-hydroxy-butyl]-(3-methoxybenzyl)-carbamic acid benzyl ester.

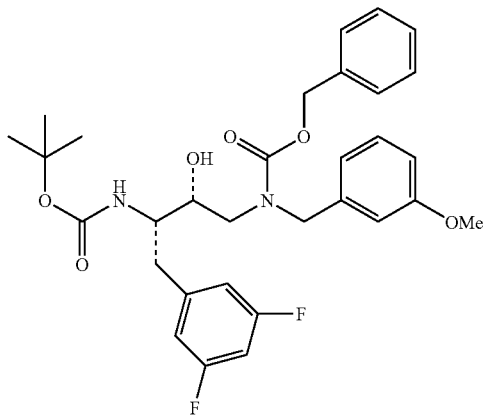

A mixture of tert-butyl (1S)-2-(3,5-difluorophenyl)-1-[(2S)-oxiran-2-yl]ethylcarbamate (1.0 g, 3.3 mmol) and 3-methoxybenzylamine (1.8 g, 13.3 mmol) in isopropyl alcohol (30 ml) was stirred at room temperature for 6.5 h. The reaction mixture was diluted with EtOAc (100 ml) and washed with 1 N HCl (3×30 ml), sat'd aq. NaHCO₃ (1×50 ml) and brine. The organic layer was dried over Na₂SO₄ and concentrated in vacuo to yield an off white solid. The residue was dissolved in THF (20 ml) and chilled to 0° C. followed by the addition of Et₃N (0.6 ml, 4.4 mmol) and benzylchloroformate (0.5 ml, 3.6 mmol). The reaction mixture was warmed spontaneously for 3 h. The reaction mixture was diluted with EtOAc, washed with 1N HCl, NaHCO₃, and brine. The organic layer was dried over Na₂SO₄ and concentrated in vacuo. Flash chromatography 30% EtOAC/Heptanes yields 1.3 g (70%) of [3-tert-butoxycarbonylamino-4-(3,5-difluoro-phenyl)-2-hydroxy-butyl]-(3-methoxybenzyl)-carbamic acid benzyl ester. MS (ESI+) for $C_{31}H_{36}F_2N_2O_6$ m/z 570.8 (M+H)⁺.

Step 2: Benzyl (2R,3S)-3-amino-4-(3,5-difluorophenyl)-2-hydroxybutyl(3-methoxybenzyl)carbamate

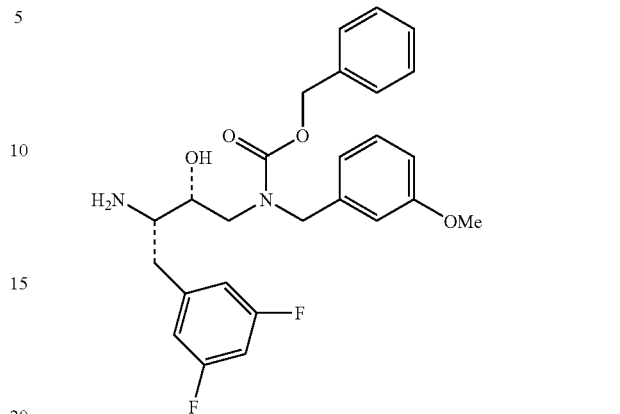

To a 20 ml solution of [3-tert-butoxycarbonylamino-4-(3,5-difluoro-phenyl)-2-hydroxy-butyl]-(3-methoxybenzyl)-carbamic acid benzyl ester (0.5 g, 0.9 mmol) at 0° C. was added trifluoroacetic acid (4 ml). The cold bath was removed and the mixture stirred at r.t. for 1 h. The solvent was removed in vacuo and the residue dissolved in 10% aq. NaHCO₃, extracted with EtOAc (3×115 ml). The combined organic layers were dried over Na₂SO₄ and concentrated in vacuo to yield an amorphous solid. MS (ESI+) for $C_{26}H_{28}F_2N_2O_4$ m/z 471.2 (M+H)⁺. The crude amine was used in subsequent steps without purification.

Step 3. {4-(3,5-Difluoro-phenyl)-3-[3-(2-dipropylcarbamoyl-ethyl)-ureido]-2-hydroxy-butyl}-(3-methoxybenzyl)-carbamic acid benzyl ester

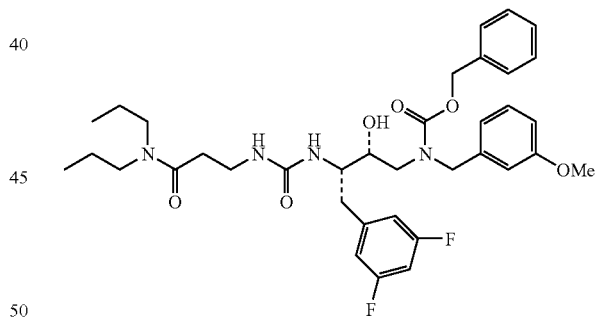

4-(dipropylamino)-4-oxobutanoic acid (0.08 g, 0.40 mmol) generated by the addition of dipropyl amine to succinic anhydride was treated with Et₃N (62 µL, 0.44 mmol) and (PhO)₂P(O)N₃ (77 µL, 0.36 mmol) in 3 ml of toluene. The mixture was stirred at r.t. for 30 min. then immersed in a 90° C. oil bath for 45 min. The mixture was rapidly cooled to 0° C. followed by the addition of the amine from step 2 (0.19 g, 0.40 mmol). The mixture was warmed to r.t. and stirred for 1 h. The mixture was diluted with EtOAc 30 mL and washed with 1N HCl (2×10 mL), NaHCO₃ (1×10 mL) and brine. The organic layer was dried over Na₂SO₄ and concentrated in vacuo to yield 190 mg of as a clear glass after radial chromatography 60% EtOAc/Heptanes. MS (ESI+) for $C_{36}H_{46}F_2N_4O_6$ m/z 668.9 (M+H)⁺.

Step 4 N³-[({(1S,2R)-1-(3,5-difluorobenzyl)-2-hydroxy-3-[(3-methoxybenzyl)amino]propyl}amino)carbonyl]-N¹,N¹-dipropyl-beta-alaninamide

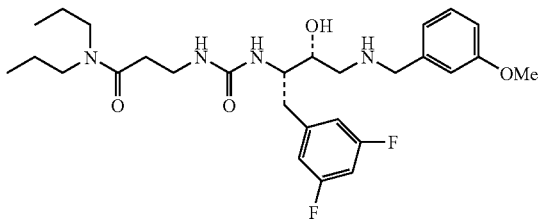

To a MeOH (3 mL) solution of the product from step 3 (0.14 g, 0.20 mmol) was added NH₄OAc (0.008 g, 0.1 mmol) and 70 mg of Pd/C(10% by wt. on carbon). The mixture was purged with H₂ then stirred at r.t. under a ballon of H₂. After 1.5 h the mixture was filtered through Celite® and the solvent removed in vacuo to yield a clear glass. Preparative HPLC with H₂O/CH₃CN (1 formic acid) yields the title compound as a white solid. MS (ESI+) for C₂₈H₄₀F₂N₄O₄ m/z 535.3 (M+H)⁺.

Example 2

2-{[({(1S,2R)-1-(3,5-difluorobenzyl)-2-hydroxy-3-[(3-methoxybenzyl)amino]propyl}amino)carbonyl]amino}-N,N-dipropylethanesulfonamide (Compound 2):

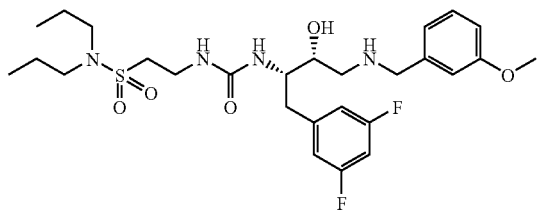

Step 1 {4-(3,5-Difluoro-phenyl)-3-[3-(2-dipropylsulfamoyl-ethyl)-ureido]-2-hydroxy-butyl}-(3-methoxybenzyl)-carbamic acid benzyl ester

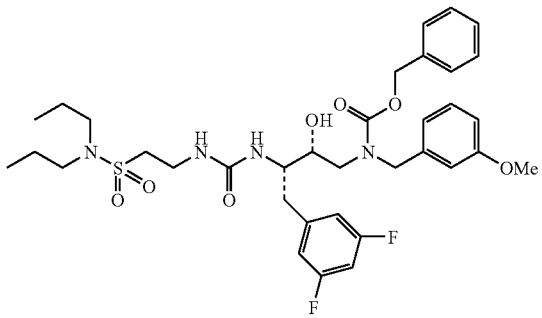

3-Dipropylsulfamoyl-proprionic acid (0.96 g, 0.40 mmol) was treated with Et₃N (62 μL, 0.44 mmol) and (PhO)₂P(O)N₃ (77 μL, 0.36 mmol) in 3 ml of toluene. The mixture was stirred at r.t. for 30 min. then immersed in a 90° C. oil bath for 45 min. The mixture was rapidly cooled to 0° C. followed by the addition of the amine from step 2 (0.19 g, 0.40 mmol). The mixture was warmed to r.t. and stirred for 1 h. The mixture was diluted with EtOAc 30 mL and washed with 1N HCl (2×10 mL), NaHCO₃ (1×10 mL) and brine. The organic layer was dried over Na₂SO₄ and concentrated in vacuo to yield 120 mg of as a clear glass after radial chromatography 60% EtOAc/Heptanes. MS (ESI+) for C₃₅H₄₆F₂N₄O₇S m/z 705.9 (M+H)⁺.

Step 2 2-{[({(1S,2R)-1-(3,5-difluorobenzyl)-2-hydroxy-3-[(3-methoxybenzyl)amino]propyl}amino)carbonyl]amino}-N,N-dipropylethanesulfonamide

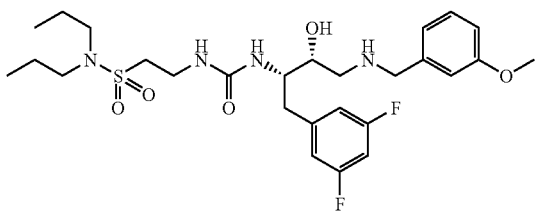

To a MeOH (3 mL) solution of the product from step 1 (0.12 g, 0.17 mmol) was added NH₄OAc (0.007 g, 0.1 mmol) and 50 mg of Pd/C(10% by wt. on carbon). The mixture was purged with H₂ then stirred at r.t. under a ballon of H₂. After 40 min. the mixture was filtered through Celite® and the solvent removed in vacuo to yield an off white solid. Recyrstallization from EtOAc/MeOH yields the title compound as a white solid. MS (ESI+) for C₂₇H₄₀F₂N₄O₅S m/z 571.2 (M+H)⁺.

Example 3 tert-butyl (1S,2R)-1-(3,5-difluorobenzyl)-2-hydroxy-3-[(6-iodo-3,4-dihydro-2H-chromen-4-yl)amino]propylcarbamate intermediate (Compound 3):

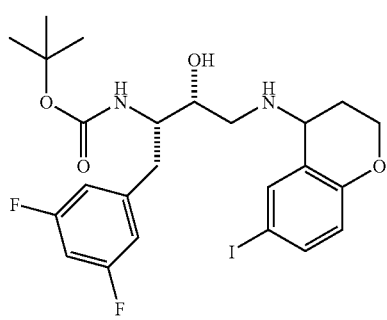

Step 1 6-Iodo-chroman-4-ylamine

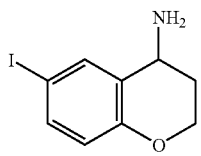

To a CH$_2$Cl$_2$ (80 ml) solution of 6-iodo-4-chromanol (10.0 g, 36 mmol) and diisopropylethyl amine (19 ml, 108 mmol), at 0° C., was added the MsCl (4.2 ml, 54 mmol). After stirring for 1.5 h the solvent was removed in vacuo and the resulting residue dissolved in 150 ml of DMF followed by the addition of Na N$_3$ (3.5 g, 54 mmol). The reaction was heated to 70° C. for 6.5 h then cooled to rt. followed by the addition of 900 ml 0f 1 N HCl and extraction with Et$_2$O (4×200 ml). The combined Et$_2$O layers were dried over MgSO$_4$ and concentrated in vacuo to yield 9.5 g of the azide as yellow oil. MS (ESI+) for C$_9$H$_8$IN$_3$O m/z 300.97 (M+H)$^+$. The crude azide (5.0 g, 16.6 mmol) was dissolved in THF (50 ml) and treated with PPh$_3$ (5.2 g, 20.0 mmol). The mixture stirred at rt. for 30 min. followed by the addition of 4 ml of H$_2$O. The mixture was then heated to 60° C. overnight. After cooling the mixture was concentrated in vacuo and the resulting residue treated with 1 N HCl. The aqueous layer was washed with CH$_2$Cl$_2$ and then adjusted to pH=12 with NaOH pellets. The basic aqueous layer was extracted with CH$_2$Cl$_2$ and the combined organic layers dried over Na$_2$SO$_4$ and treated with activated carbon. The mixture was filtered through Celite® and concentrated in vacuo to yield 6-Iodo-chroman-4-ylamine 3.6 g (79%) as clear oil that solidifies upon standing. MS (ESI+) for C$_9$H$_{10}$INO m/z 275.98 (M+H)$^+$.

Step 2 tert-butyl (1S,2R)-1-(3,5-difluorobenzyl)-2-hydroxy-3-[(6-iodo-3,4-dihydro-2H-chromen-4-yl)amino]propylcarbamate:

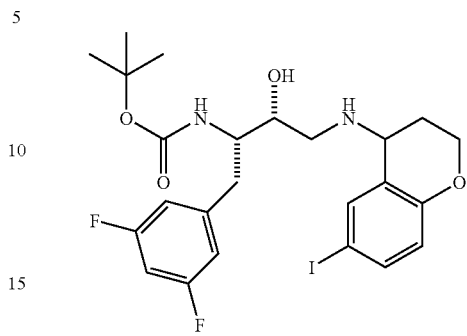

An isopropyl alcohol (25 ml) solution of tert-butyl (1S)-2-(3,5-difluorophenyl)-1-[(2S)-oxiran-2-yl]ethylcarbamate (2.2 g, 7.2 mmol) and 6-Iodo-chroman-4-ylamine (3.0 g, 10.9 mmol) was stirred at 75° C. for 0 h. The IPA was removed in vacuo and the resulting residue dissolved in EtOAc (200 ml). The organic layer was washed with 1 N HCl (4×50 ml), followed by NaHCO$_3$ (2×50 ml), and brine (1×50 ml). The organic layer was dried over Na$_2$SO$_4$ and concentrated in vacuo to yield 3.5 g (85%) of the title compound as an off white solid. MS (ESI+) for C$_{24}$H$_{29}$F$_2$IN$_2$O$_4$ m/z 574.8 (M+H)$^+$.

Example 4

The following compounds are prepared essentially according to the procedures outlined above and described in the above examples. The substituents R and R$_c$ are defined for formula A in the table.

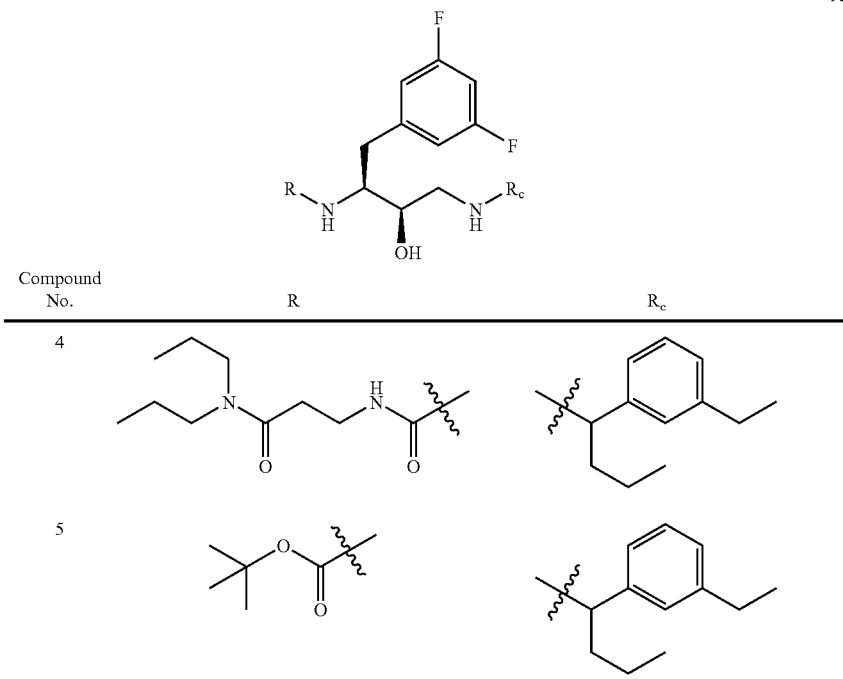

-continued
| | A |
|---|---|
| | 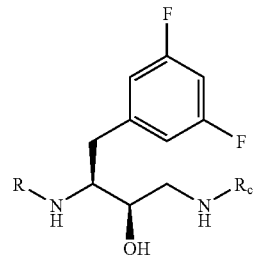 |
| Compound No. | R | R_c |
| 6 |  | 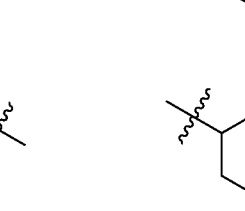 |
| 7 | 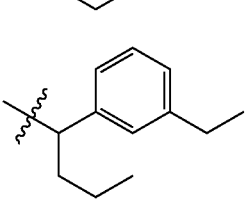 | 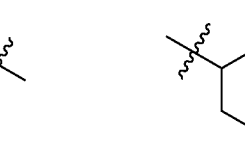 |
| 8 | 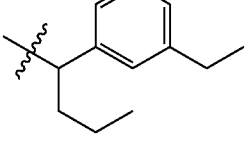 |  |
| 9 | 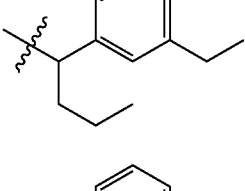 |  |
| 10 | 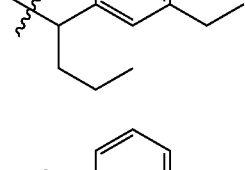 |  |
| 11 | 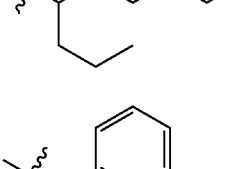 |  |
| 12 | 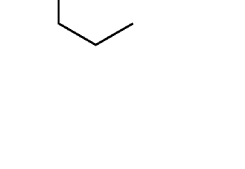 | |

-continued

A

| Compound No. | R | R_c |
|---|---|---|
| 13 | sec-butyl-NH-C(=O)-C(CH3)- | 3-ethylphenyl-CH(CH2CH2CH3)- |
| 14 | ethyl-O-C(=O)-C(CH3)- | 3-ethylphenyl-CH(CH2CH2CH3)- |
| 15 | (n-Pr)2N-C(=O)-CH2CH2-NH-C(=O)-C(CH3)- | 1-(3-ethylphenyl)cyclohexyl- |
| 16 | tert-butyl-O-C(=O)- | 1-(3-ethylphenyl)cyclohexyl- |
| 17 | (n-Pr)2N-S(=O)2-CH2CH2-NH-C(=O)-C(CH3)- | 1-(3-ethylphenyl)cyclohexyl- |
| 18 | phenyl-NH-C(=O)-C(CH3)- | 1-(3-ethylphenyl)cyclohexyl- |
| 19 | phenyl-O-C(=O)-C(CH3)- | 1-(3-isopropylphenyl)cyclohexyl- |

-continued

A

| Compound No. | R | R_c |
|---|---|---|
| 20 | PhNHC(O)C(CH₃)₂– | 1-(3-ethylphenyl)cyclohexyl |
| 21 | CH₃SO₂C(CH₃)₂– | 1-(3-isopropylphenyl)cyclohexyl |
| 22 | BnNHC(O)C(CH₃)₂– | 1-(3-ethylphenyl)cyclohexyl |
| 23 | n-PrNHC(O)C(CH₃)₂– | 1-(3-ethylphenyl)cyclohexyl |
| 24 | sec-BuNHC(O)C(CH₃)₂– | 1-(3-ethylphenyl)cyclohexyl |
| 25 | EtOC(O)C(CH₃)₂– | 1-(3-ethylphenyl)cyclohexyl |
| 26 | (n-Pr)₂NC(O)CH₂CH₂NHC(O)C(CH₃)₂– | 6-iodochroman-4-yl |

-continued

A

| Compound No. | R | R_c |
|---|---|---|
| 27 | tert-butyl ester (OC(=O)C(CH3)2-) | 6-iodo-chroman-4-yl |
| 28 | (propyl)2N-SO2-CH2CH2-NH-C(=O)-C(CH3)2- | 6-iodo-chroman-4-yl |
| 29 | Ph-NH-C(=O)-C(CH3)2- | 6-iodo-chroman-4-yl |
| 30 | Ph-O-C(=O)-C(CH3)2- | 6-iodo-chroman-4-yl |
| 31 | Ph-NH-C(=O)-C(CH3)2- | 6-iodo-chroman-4-yl |
| 32 | CH3-SO2-C(CH3)2- | 6-iodo-chroman-4-yl |
| 33 | PhCH2-NH-C(=O)-C(CH3)2- | 6-iodo-chroman-4-yl |

-continued
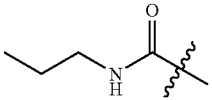
A
| Compound No. | R | R_c |
|---|---|---|
| 34 | 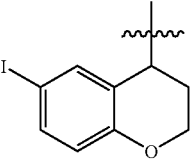 | 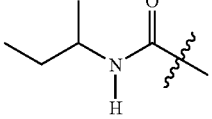 |
| 35 | 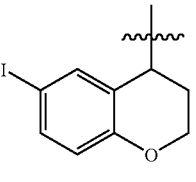 | 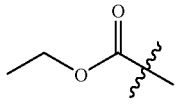 |
| 36 | 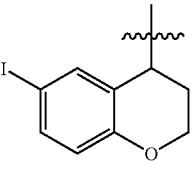 | 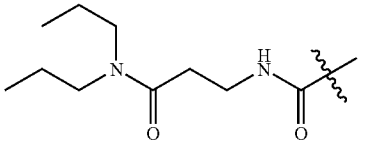 |
| 37 | 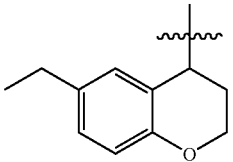 | 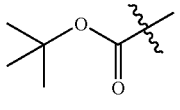 |
| 38 | 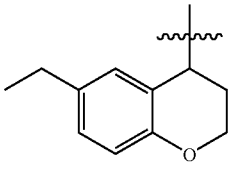 | 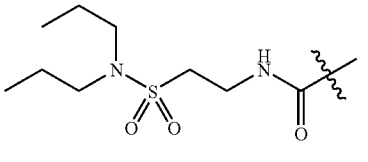 |
| 39 | 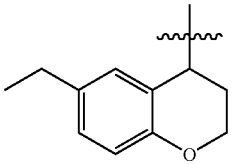 | 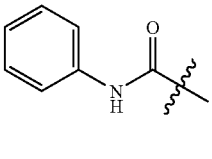 |
| 40 | 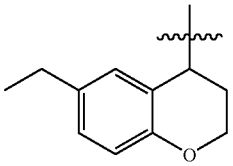 | |

-continued
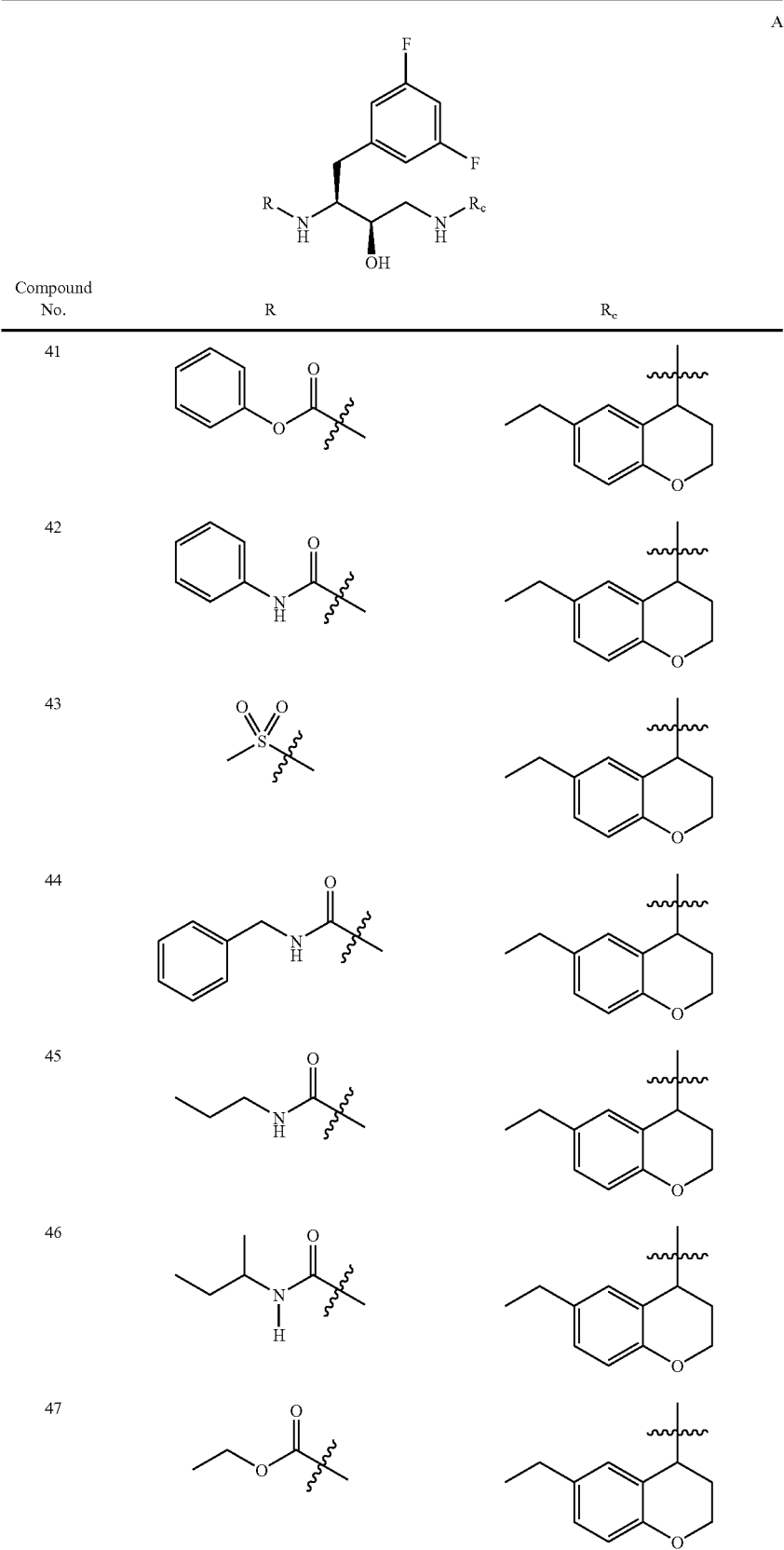

-continued
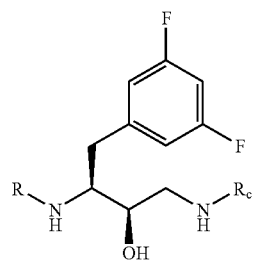
A
| Compound No. | R | R_c |
|---|---|---|
| 48 | 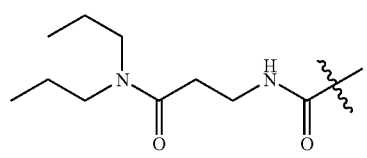 | 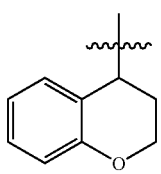 |
| 49 | 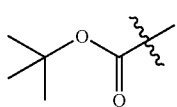 | 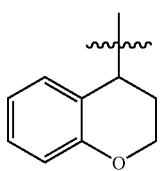 |
| 50 | 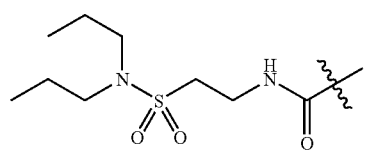 | 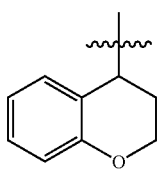 |
| 51 | 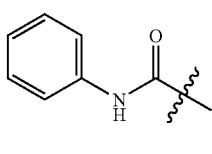 | 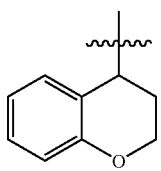 |
| 52 | 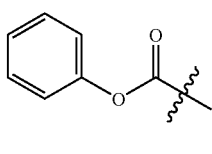 | 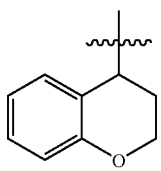 |
| 53 | 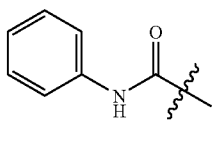 | 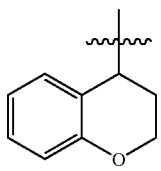 |
| 54 | 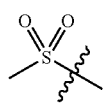 | 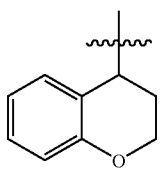 |

-continued

| | A |
|---|---|

Structure A: 3,5-difluorobenzyl group attached to a carbon bearing NHR, with adjacent CH(OH)-CH2-NHRc

| Compound No. | R | Rc |
|---|---|---|
| 55 | PhCH2-NH-C(=O)-C(CH3)(wavy)- | chroman-4-yl |
| 56 | CH3CH2CH2-NH-C(=O)-C(CH3)(wavy)- | chroman-4-yl |
| 57 | sec-butyl-NH-C(=O)-C(CH3)(wavy)- | chroman-4-yl |
| 58 | CH3CH2-O-C(=O)-C(CH3)(wavy)- | chroman-4-yl |
| 59 | (n-Pr)2N-C(=O)-CH2CH2-NH-C(=O)-C(CH3)2(wavy)- | 6-(2-cyanophenyl)chroman-4-yl |
| 60 | t-BuO-C(=O)-C(CH3)(wavy)- | 6-(2-cyanophenyl)chroman-4-yl |
| 61 | (n-Pr)2N-SO2-CH2CH2-NH-C(=O)-C(CH3)2(wavy)- | 6-(2-cyanophenyl)chroman-4-yl |

-continued
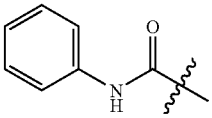
A
| Compound No. | R | R_c |
|---|---|---|
| 62 | 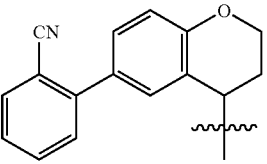 | 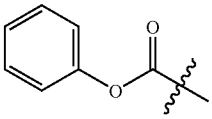 |
| 63 | 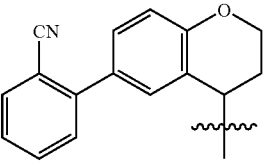 | 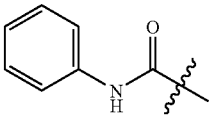 |
| 64 | 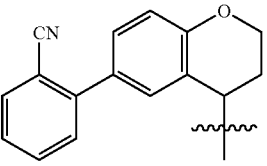 | 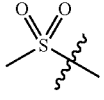 |
| 65 | 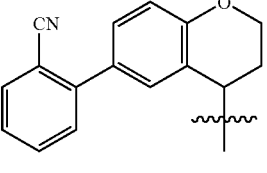 | 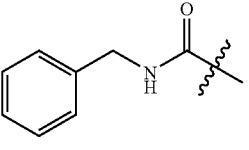 |
| 66 | 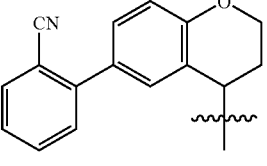 | 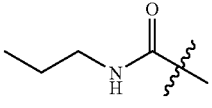 |
| 67 | 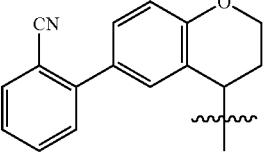 | 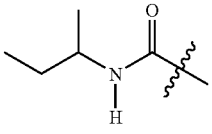 |
| 68 | 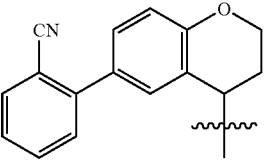 | |

-continued

A

| Compound No. | R | $R_c$ |
|---|---|---|
| 69 | ethyl 2-methylpropanoate group | 2-cyanophenyl chroman-4-yl |
| 70 | N,N-dipropyl-β-alanyl amide group | 6-cyclopentyl chroman-4-yl |
| 71 | tert-butyl 2-methylpropanoate group | 6-cyclopentyl chroman-4-yl |
| 72 | N,N-dipropylsulfamoyl ethylamide group | 6-cyclopentyl chroman-4-yl |
| 73 | phenylcarbamoyl dimethyl group | 6-cyclopentyl chroman-4-yl |
| 74 | phenyl 2-methylpropanoate group | 6-cyclopentyl chroman-4-yl |
| 75 | phenylcarbamoyl dimethyl group | 6-cyclohexyl chroman-4-yl |

-continued
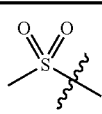
A
| Compound No. | R | R_c |
|---|---|---|
| 76 | 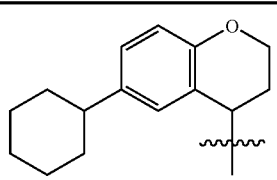 | 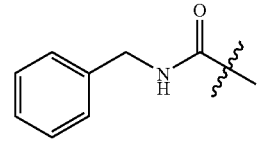 |
| 77 | 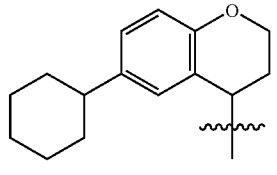 | 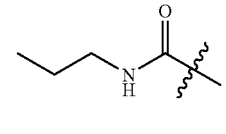 |
| 78 | 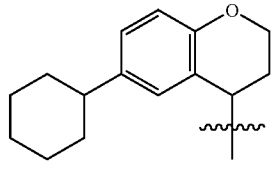 | 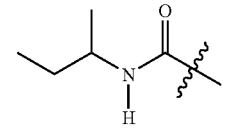 |
| 79 | 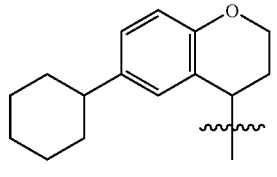 | 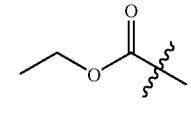 |
| 80 | 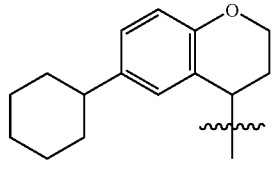 | 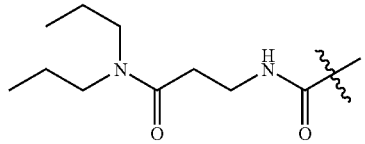 |
| 81 | 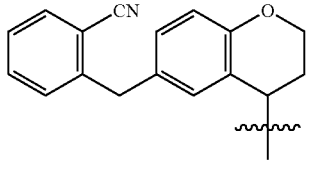 | 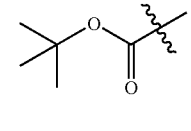 |
| 82 | 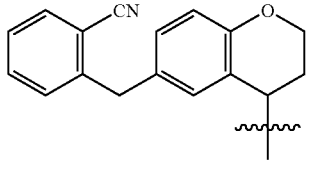 | |

-continued
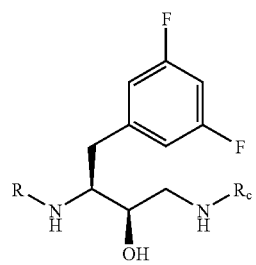
A
| Compound No. | R | $R_c$ |
|---|---|---|
| 83 | 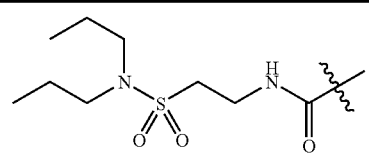 | 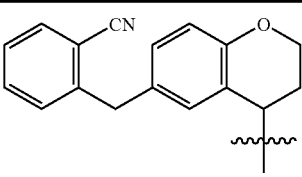 |
| 84 | 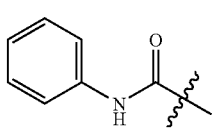 | 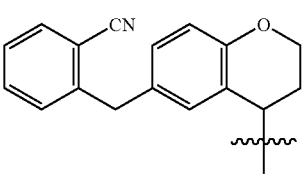 |
| 85 | 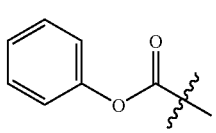 | 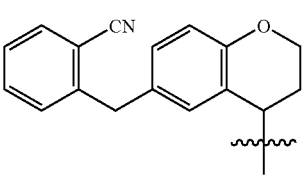 |
| 86 | 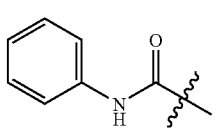 | 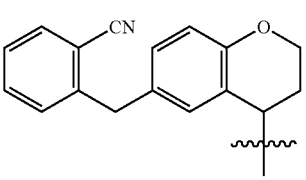 |
| 87 | 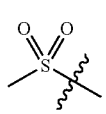 | 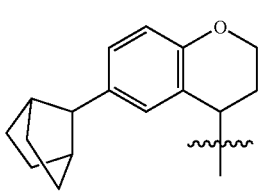 |
| 88 | 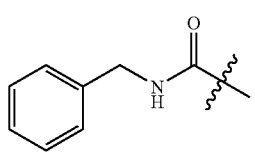 | 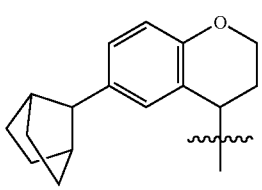 |
| 89 | 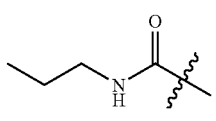 | 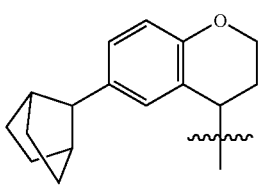 |

-continued

| Compound No. | R | R_c |
|---|---|---|
| 90 | N-sec-butyl carbamoyl-dimethyl | 6-(norbornyl)chroman-4-yl |
| 91 | ethoxycarbonyl-dimethyl | 6-(norbornyl)chroman-4-yl |
| 92 | N,N-dipropyl-succinamido-dimethyl | 6-(hexan-2-yl)chroman-4-yl |
| 93 | tert-butoxycarbonyl-dimethyl | 6-(pentan-3-yl)chroman-4-yl |
| 94 | N,N-dipropylsulfamoyl-ethylamido-dimethyl | 6-(hexan-3-yl)chroman-4-yl |
| 95 | N-phenylcarbamoyl-dimethyl | 6-(cyclohexylmethyl)chroman-4-yl |
| 96 | phenoxycarbonyl-dimethyl | 6-(cyclohexylmethyl)chroman-4-yl |

-continued

| Compound No. | R | R_c |
|---|---|---|
| 97 | N-phenyl 2-methylpropanamide | 6-(cyclohexylmethyl)chroman-4-yl |
| 98 | methanesulfonyl (isopropyl) | 6-(cyclohexylmethyl)chroman-4-yl |
| 99 | N-benzyl 2-methylpropanamide | 6-(4-methoxyphenyl)chroman-4-yl |
| 100 | N-propyl 2-methylpropanamide | 6-(4-methoxyphenyl)chroman-4-yl |
| 101 | N-sec-butyl 2-methylpropanamide | 6-(4-methoxyphenyl)chroman-4-yl |
| 102 | ethyl 2-methylpropanoate | 6-(6-methylpyridin-2-yl)chroman-4-yl |
| 103 | N,N-dipropyl-3-(amido)propanamide | 6-(5-methylpyridin-2-yl)chroman-4-yl |

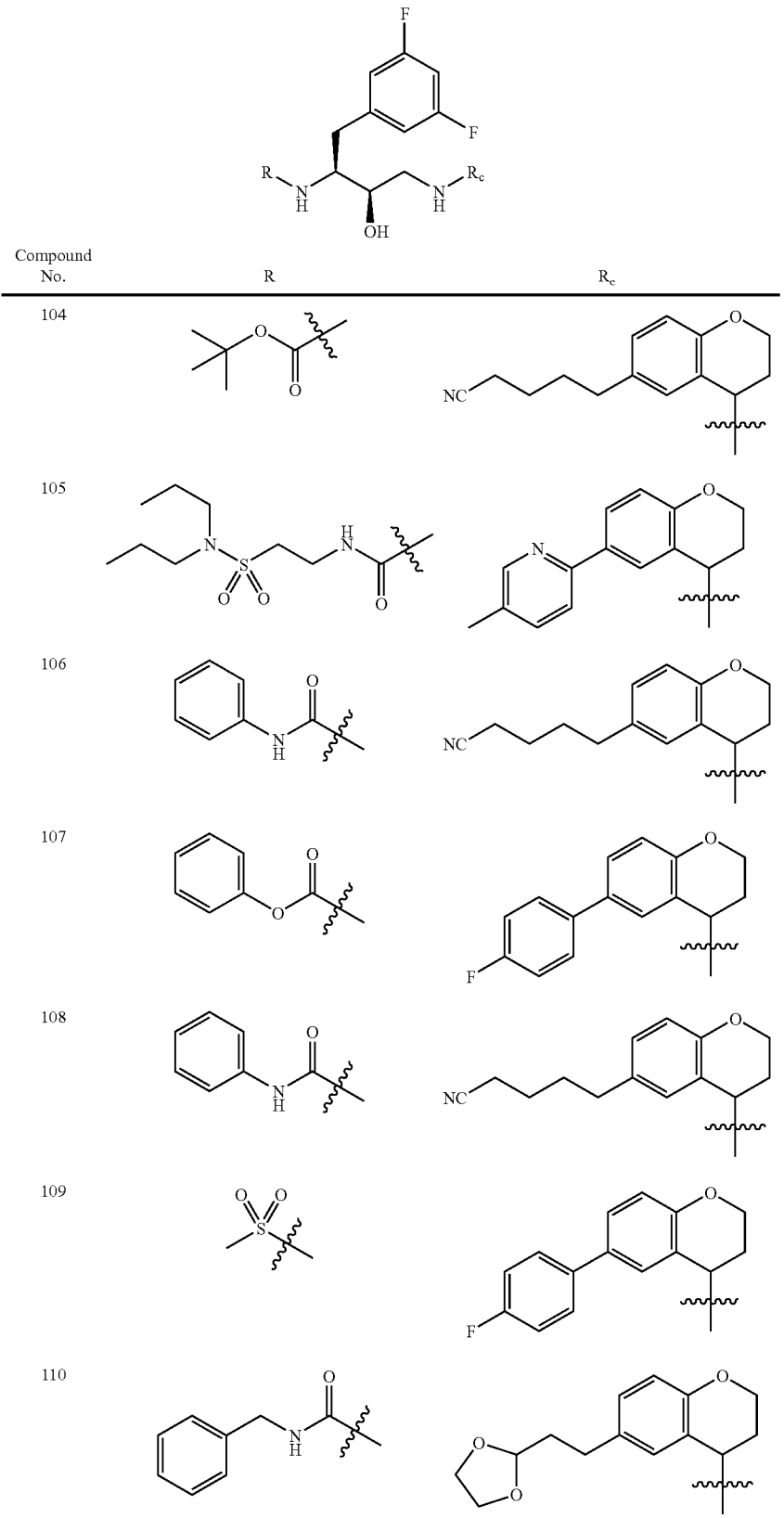

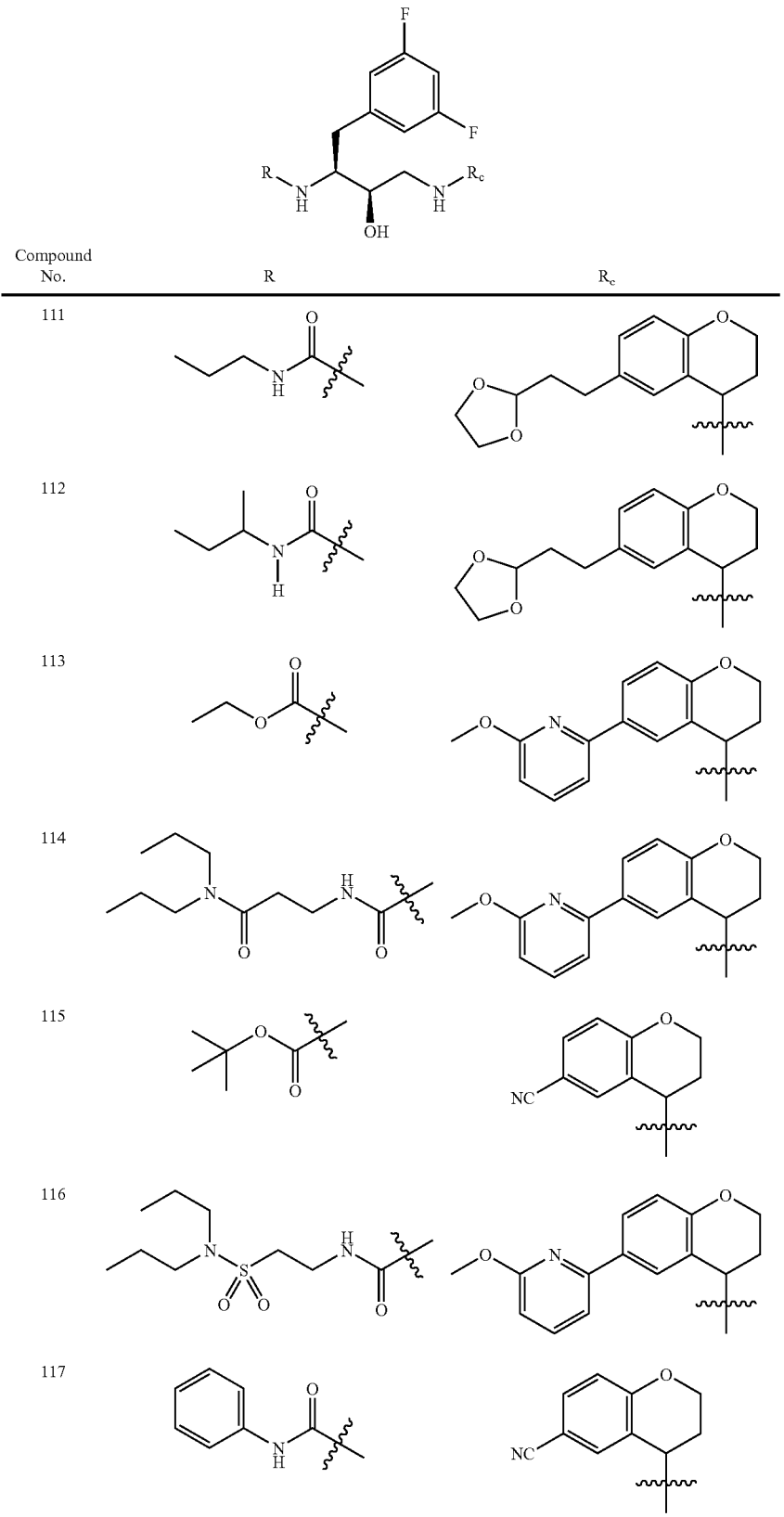

-continued
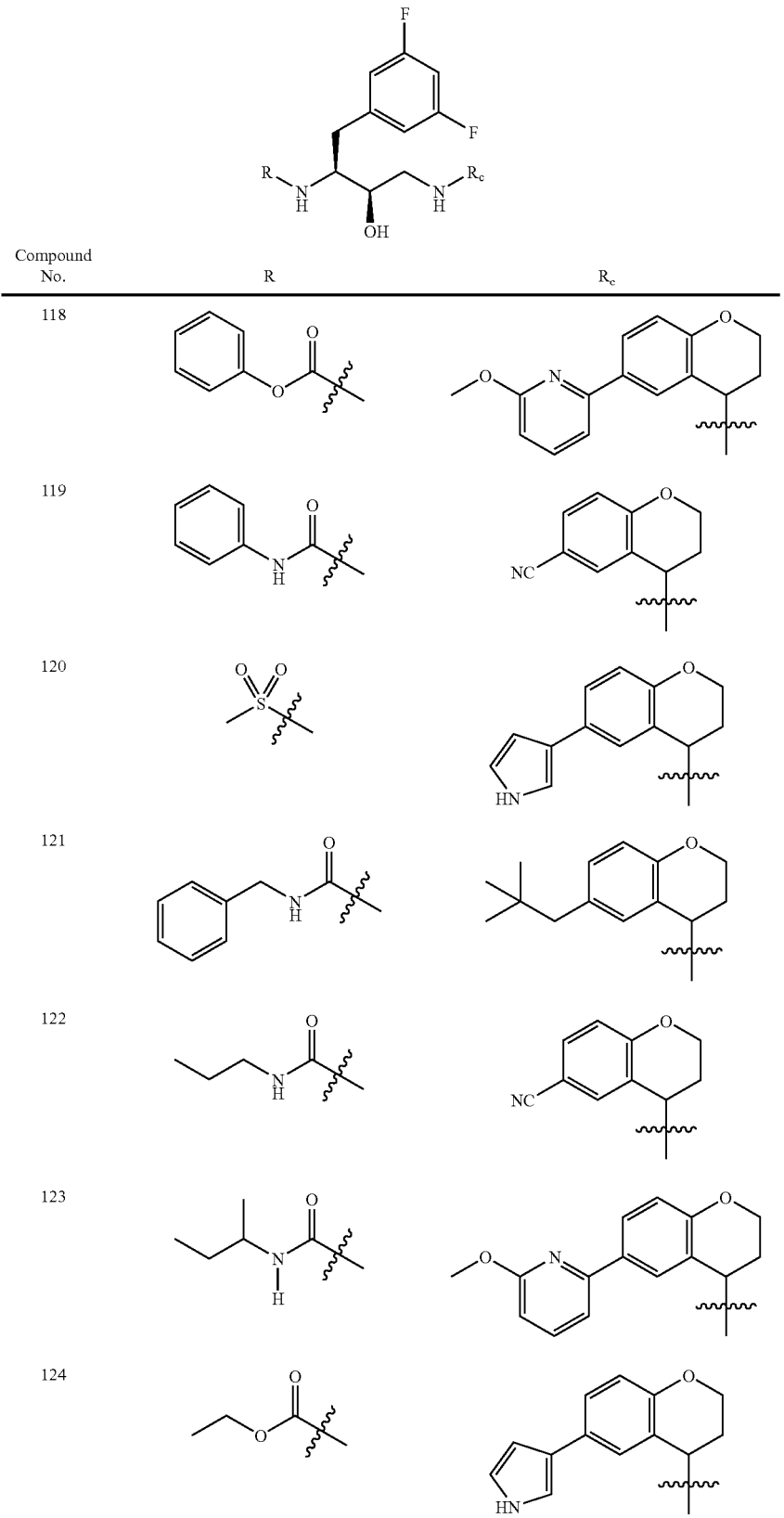

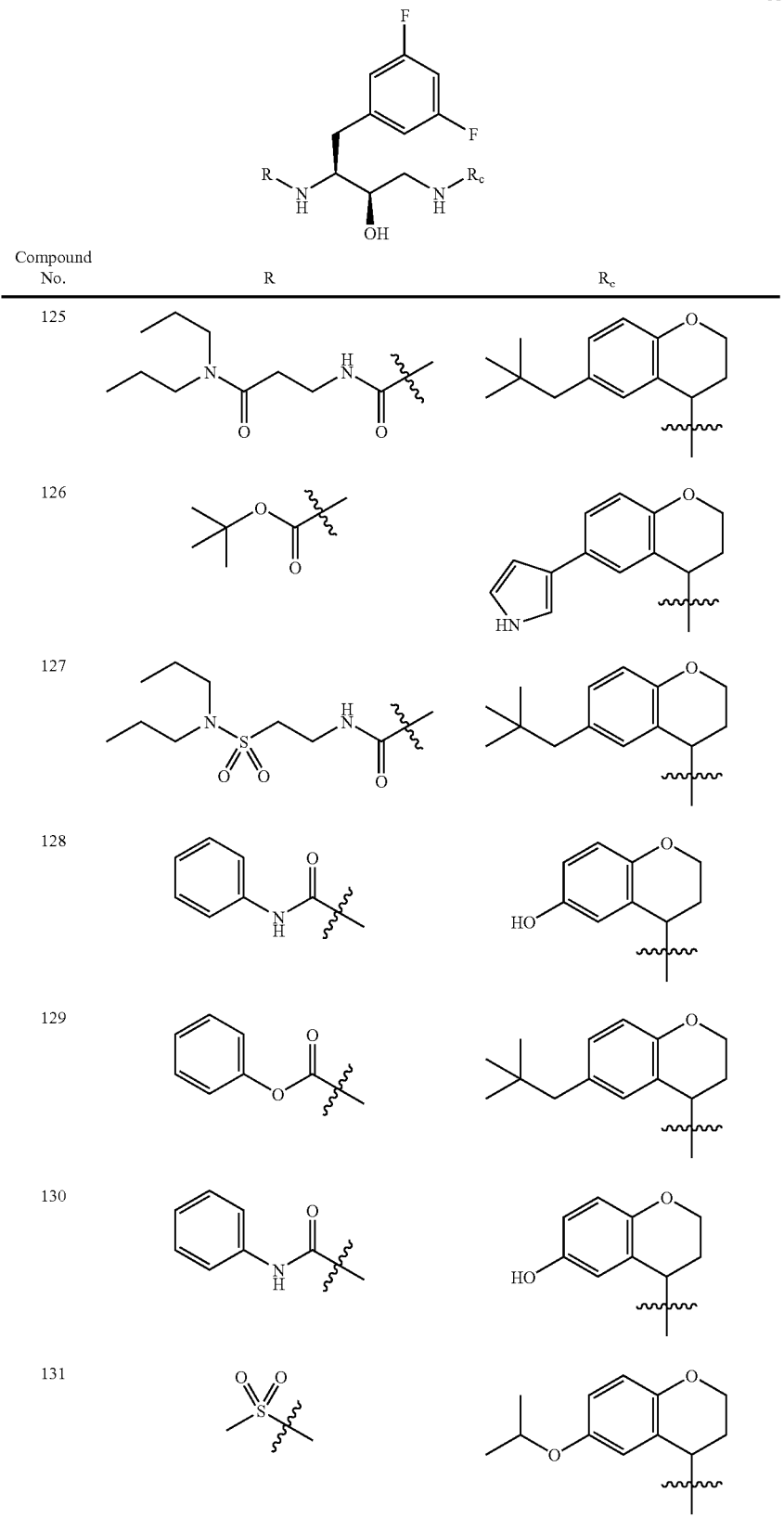

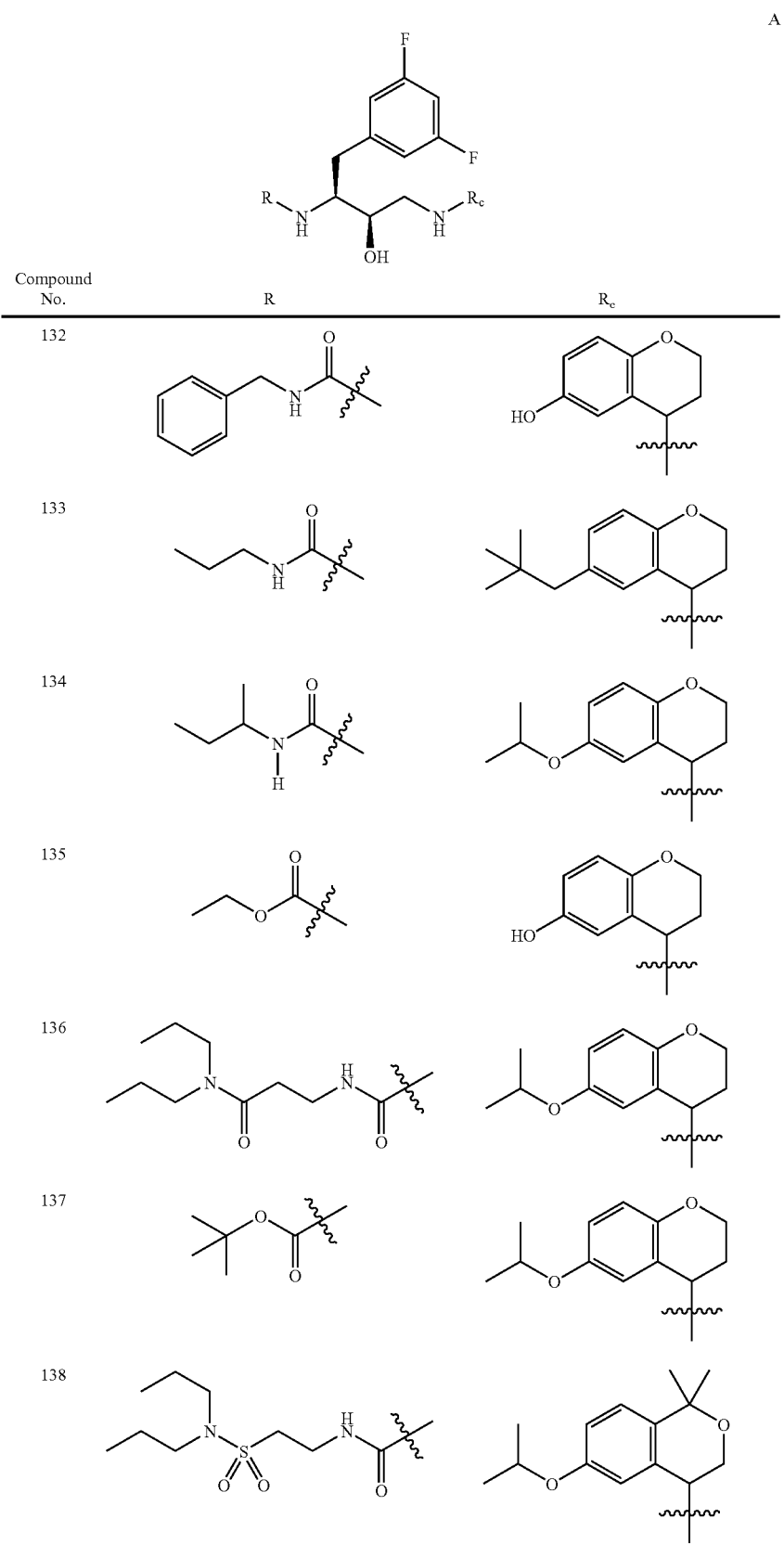

-continued
A
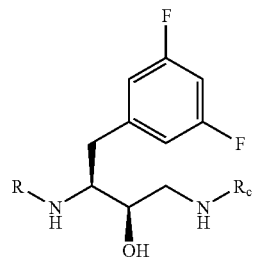
| Compound No. | R | R_c |
|---|---|---|
| 139 | 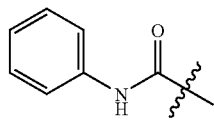 | 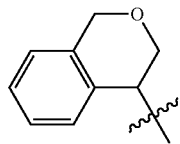 |
| 140 | 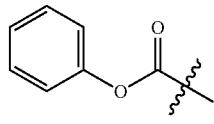 | 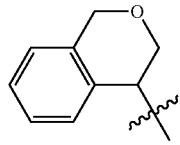 |
| 141 | 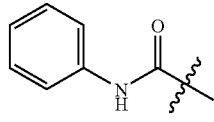 | 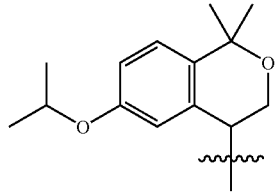 |
| 142 | 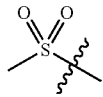 | 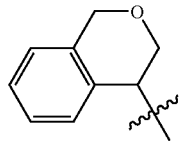 |
| 143 | 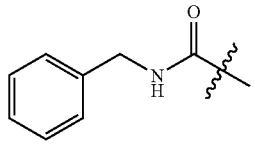 | 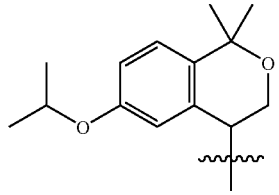 |
| 144 | 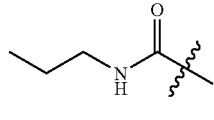 | 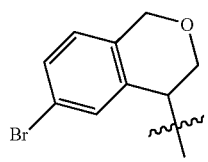 |
| 145 | 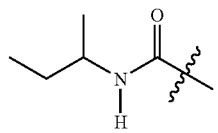 | 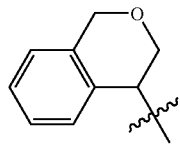 |

-continued
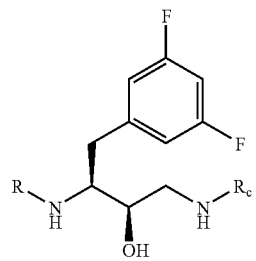
A
| Compound No. | R | R_c |
|---|---|---|
| 146 | 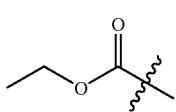 | 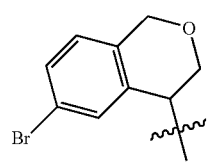 |
| 147 | 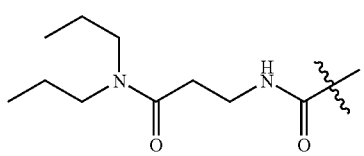 | 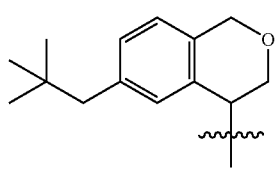 |
| 148 | 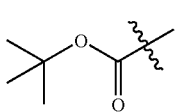 | 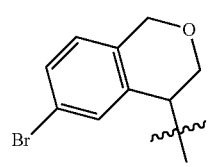 |
| 149 | 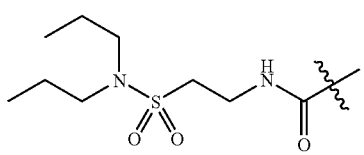 | 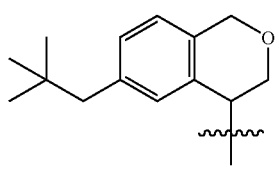 |
| 150 | 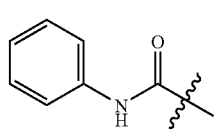 | 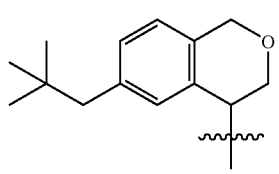 |
| 151 | 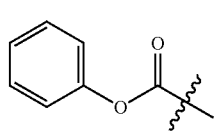 | 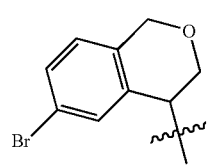 |
| 152 | 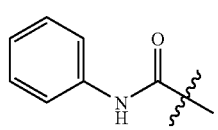 | 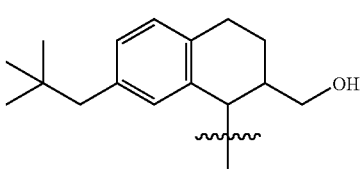 |

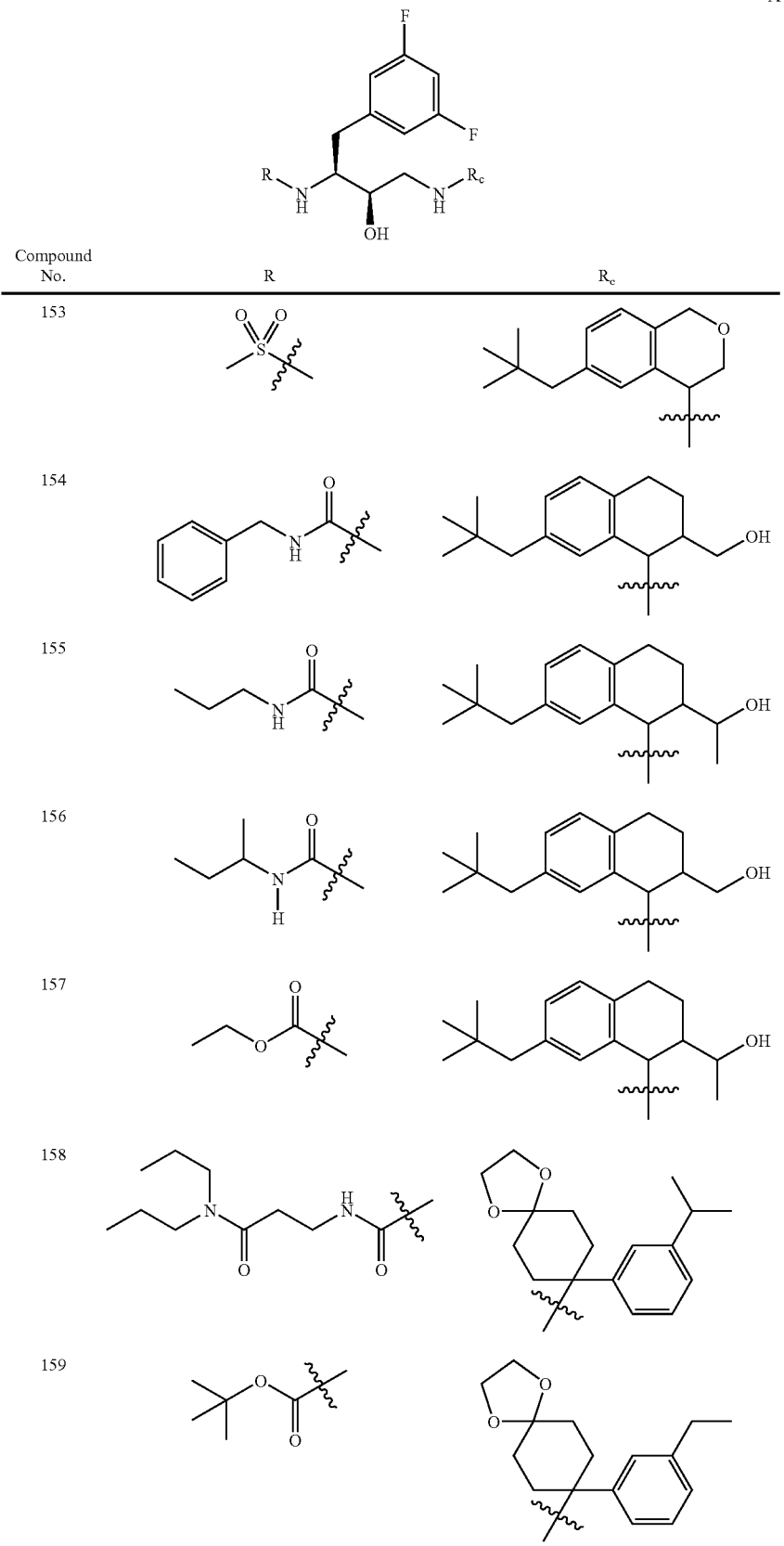

-continued
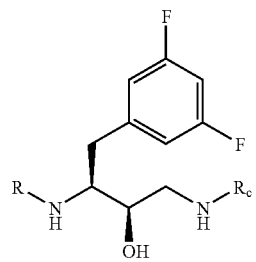
A
| Compound No. | R | $R_c$ |
|---|---|---|
| 160 | 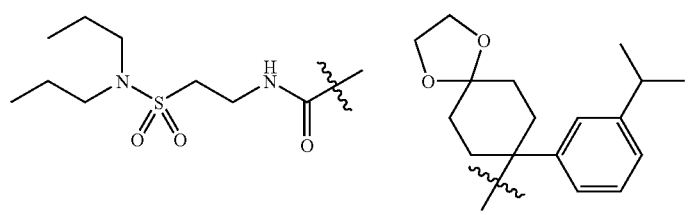 | |
| 161 | 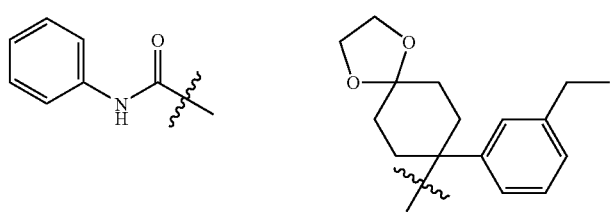 | |
| 162 | 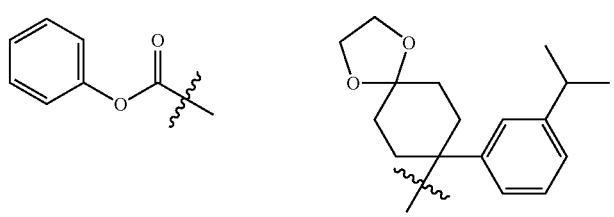 | |
| 163 | 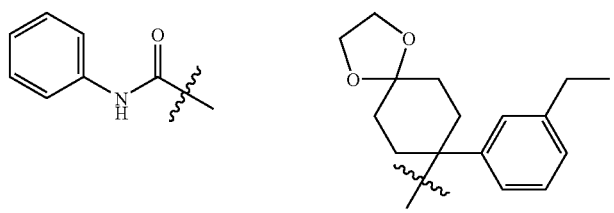 | |
| 164 | 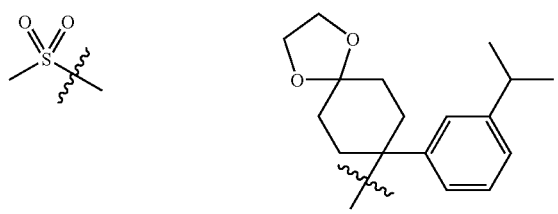 | |

-continued
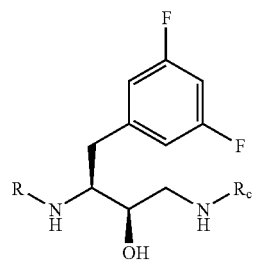
A
| Compound No. | R | R_c |
|---|---|---|
| 165 | 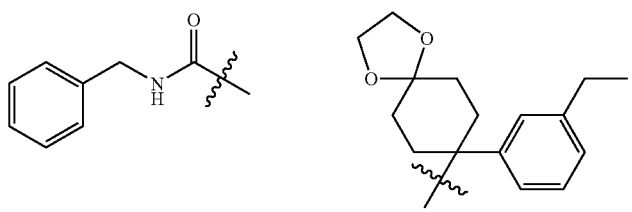 | |
| 166 | 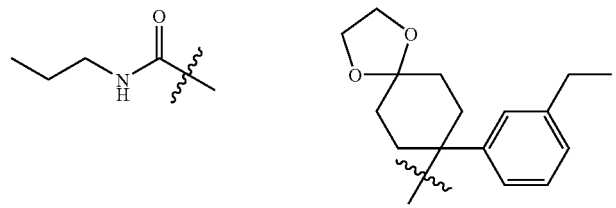 | |
| 167 | 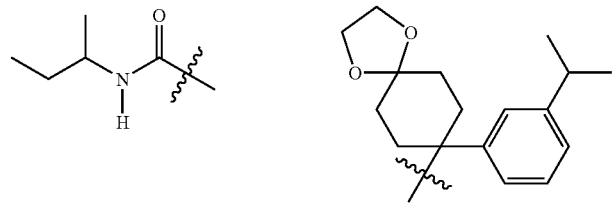 | |
| 168 | 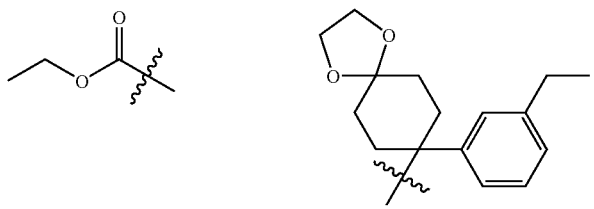 | |
| 169 | 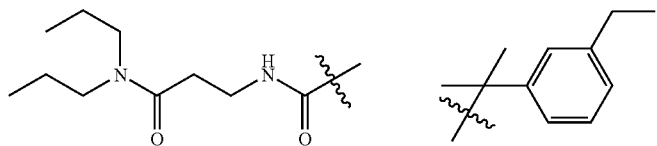 | |
| 170 |  | |

-continued
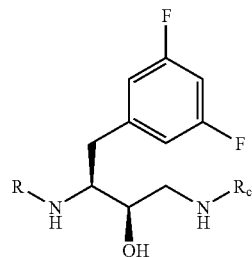
A
| Compound No. | R | R_c |
|---|---|---|
| 171 | 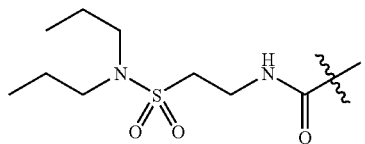 | 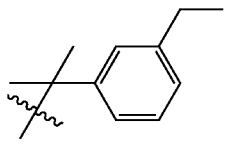 |
| 172 | 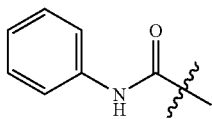 | 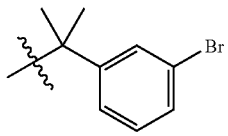 |
| 173 | 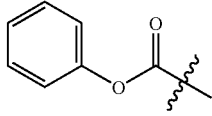 | 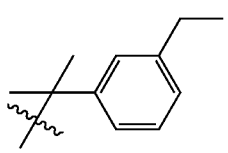 |
| 174 | 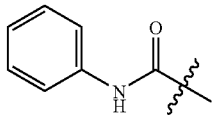 | 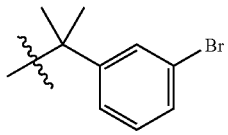 |
| 175 | 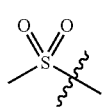 | 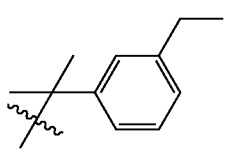 |
| 176 | 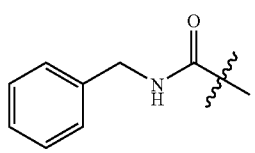 | 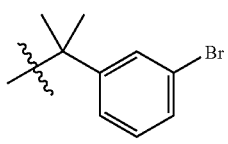 |
| 177 | 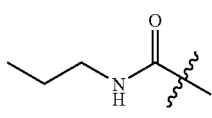 | 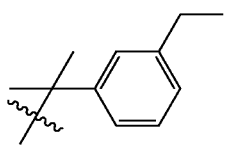 |
| 178 | 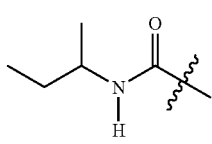 | 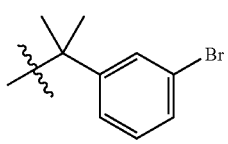 |

-continued
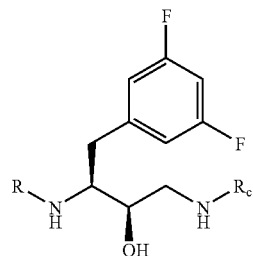
A
| Compound No. | R | $R_c$ |
|---|---|---|
| 179 | 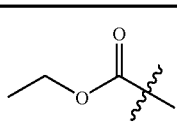 | 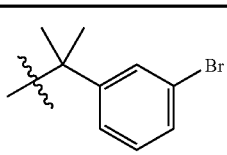 |
| 180 | 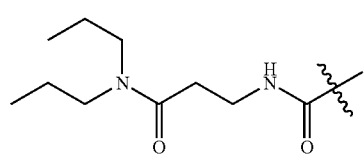 | 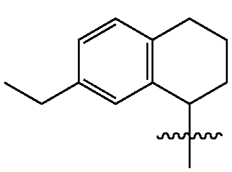 |
| 181 | 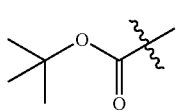 | 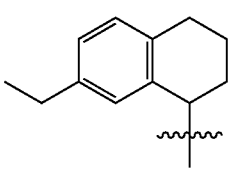 |
| 182 | 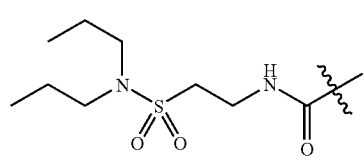 | 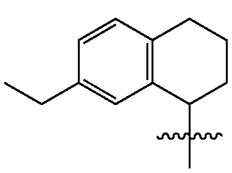 |
| 183 | 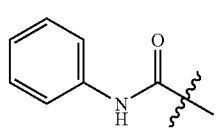 | 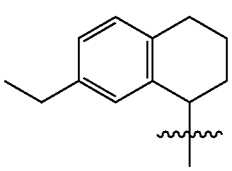 |
| 184 | 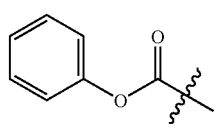 | 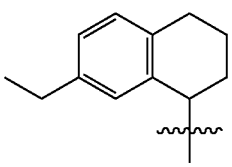 |
| 185 | 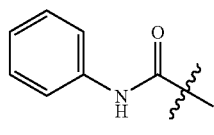 | 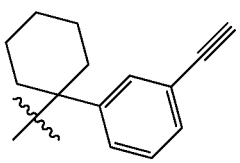 |

-continued
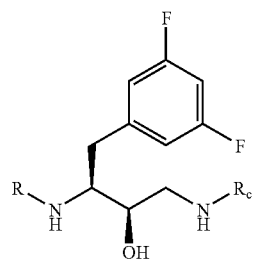
A
| Compound No. | R | R_c |
|---|---|---|
| 186 | 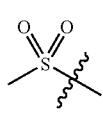 | 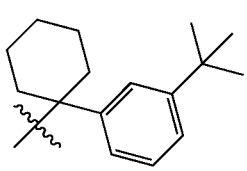 |
| 187 | 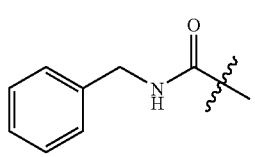 | 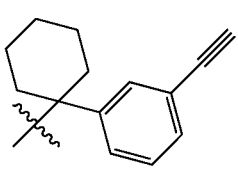 |
| 188 | 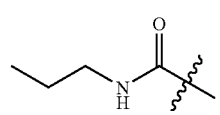 | 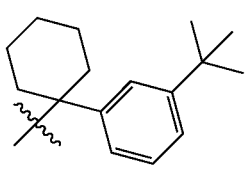 |
| 189 | 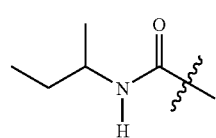 | 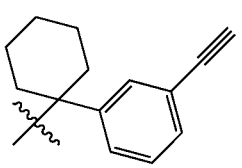 |
| 190 | 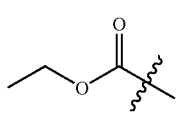 | 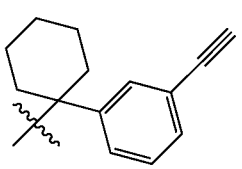 |
| 191 | 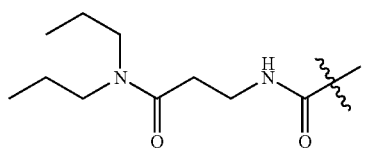 | 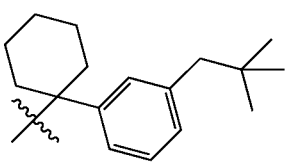 |
| 192 | 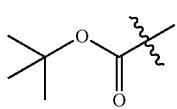 | 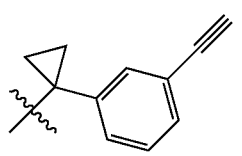 |

-continued

| Compound No. | R | R_c |
|---|---|---|
| 193 | dipropylsulfamoyl-ethyl-NH-C(CH3)2-C(O)- | 1-(3-neopentylphenyl)cyclohexyl |
| 194 | PhNH-C(O)-C(CH3)2- | 1-(3-ethynylphenyl)cyclopropyl |
| 195 | PhO-C(O)-C(CH3)2- | 1-(3-neopentylphenyl)cyclohexyl |
| 196 | PhNH-C(O)-C(CH3)2- | 1-(3-ethynylphenyl)cyclopropyl |
| 197 | CH3-S(O)2-C(CH3)2- | 1-(3-ethylphenyl)cyclopropyl |
| 198 | PhCH2-NH-C(O)-C(CH3)2- | 1-(3-ethylphenyl)cyclopropyl |
| 199 | n-Pr-NH-C(O)-C(CH3)2- | 1-(3-ethynylphenyl)cyclopropyl |
| 200 | sec-Bu-NH-C(O)-C(CH3)2- | 1-(3-ethylphenyl)cyclopropyl |

-continued
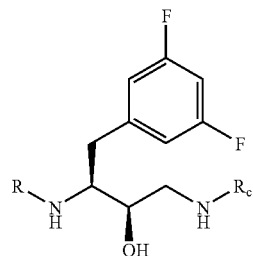
A
| Compound No. | R | R_c |
|---|---|---|
| 201 | 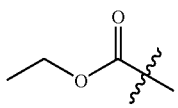 | 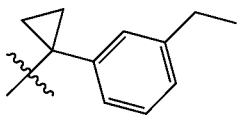 |
| 202 | 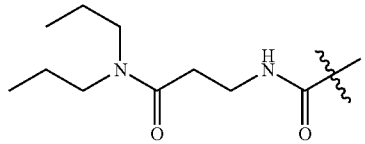 | 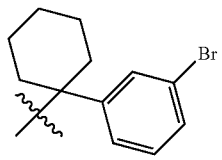 |
| 203 | 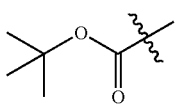 | 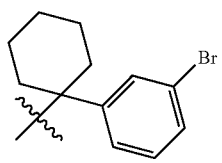 |
| 204 | 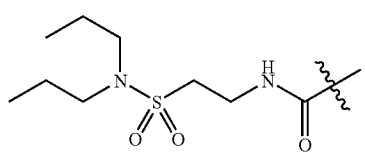 | 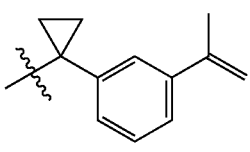 |
| 205 | 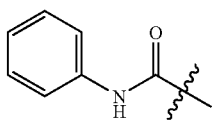 | 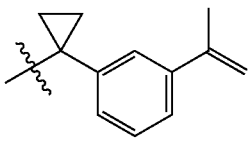 |
| 206 | 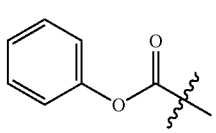 | 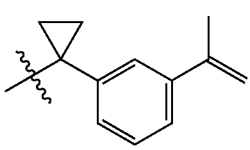 |
| 207 | 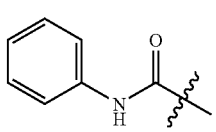 | 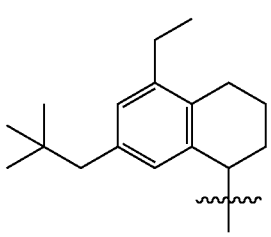 |

-continued
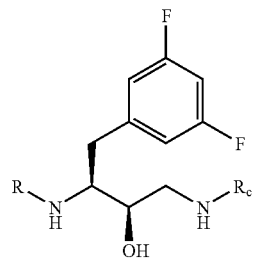
A
| Compound No. | R | R_c |
|---|---|---|
| 208 | 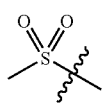 | 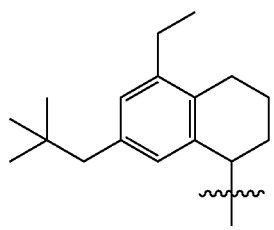 |
| 209 | 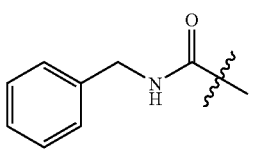 | 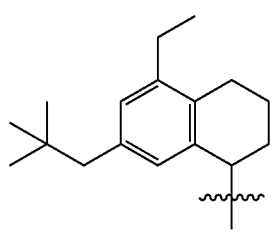 |
| 210 | 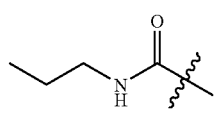 | 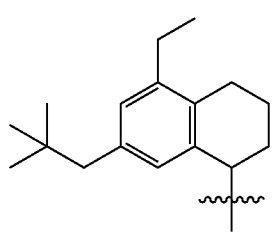 |
| 211 | 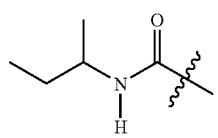 | 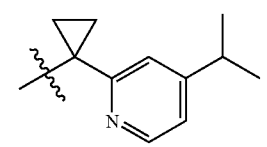 |
| 212 | 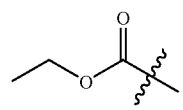 | 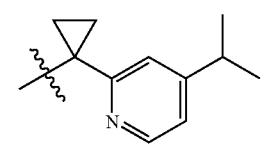 |
| 213 | 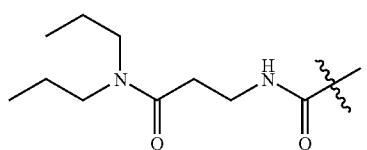 | 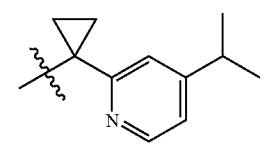 |

-continued
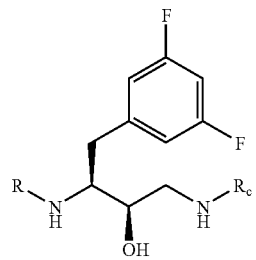
| Compound No. | R | $R_c$ |
|---|---|---|
| 214 | 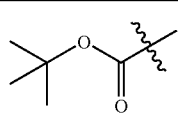 | 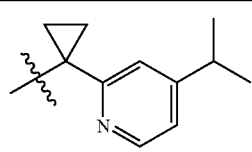 |
| 215 | 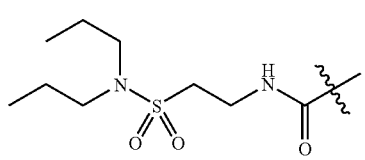 | 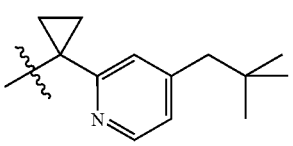 |
| 216 | 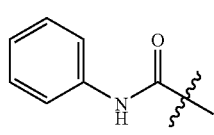 | 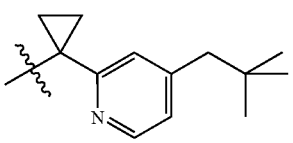 |
| 217 | 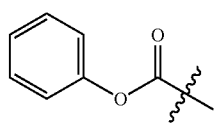 | 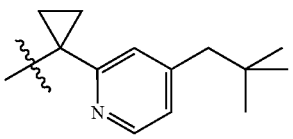 |
| 218 | 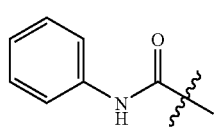 | 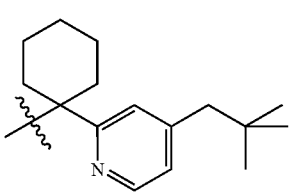 |
| 219 | 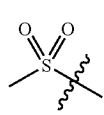 | 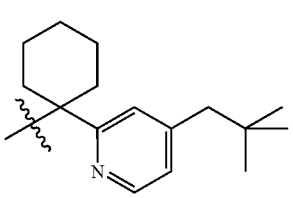 |
| 220 | 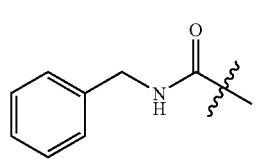 | 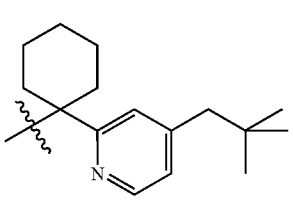 |

-continued
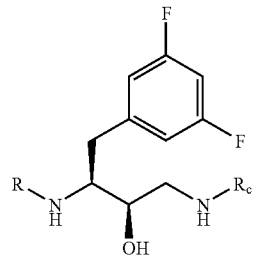
| Compound No. | R | $R_c$ |
|---|---|---|
| 221 | 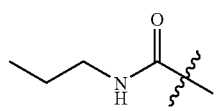 | 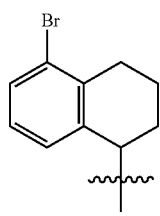 |
| 222 | 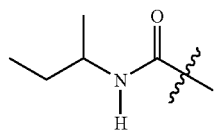 | 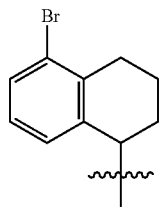 |
| 223 | 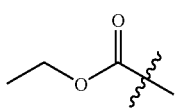 | 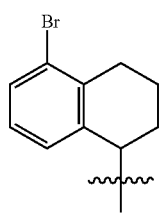 |
| 224 | 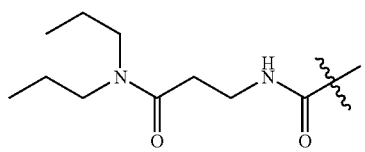 | 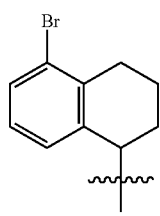 |
| 225 | 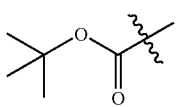 | 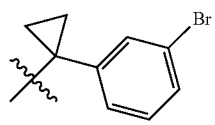 |
| 226 | 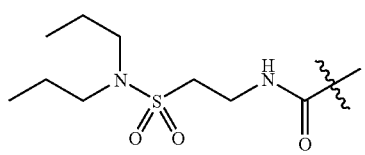 | 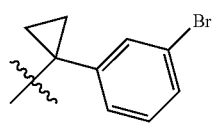 |

-continued
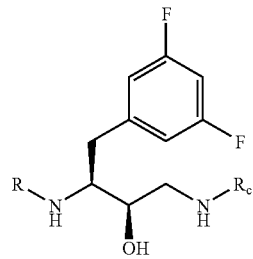
A
| Compound No. | R | $R_c$ |
|---|---|---|
| 227 | 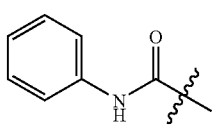 | 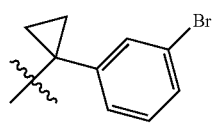 |
| 228 | 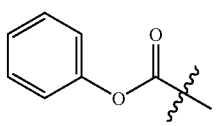 | 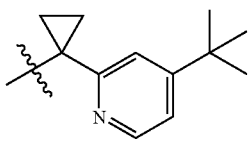 |
| 229 | 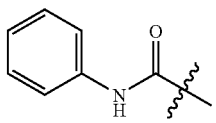 | 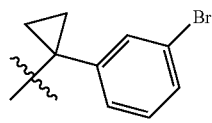 |
| 230 | 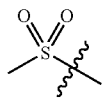 | 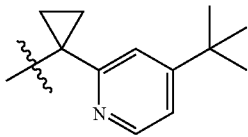 |
| 231 | 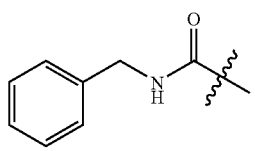 | 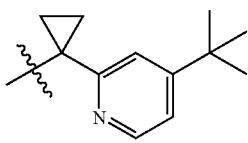 |
| 232 | 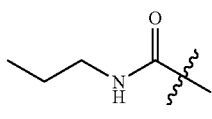 | 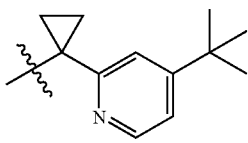 |
| 233 | 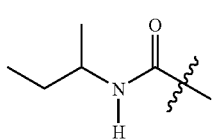 | 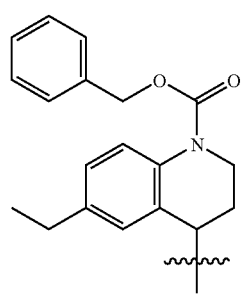 |

-continued
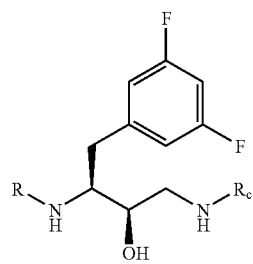
A
| Compound No. | R | $R_c$ |
|---|---|---|
| 234 | 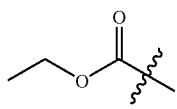 | 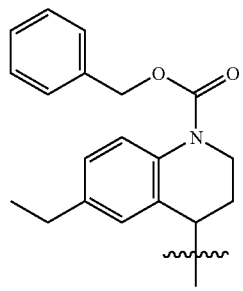 |
| 235 | 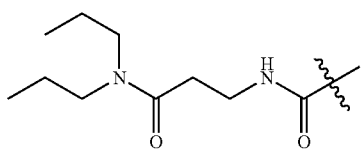 | 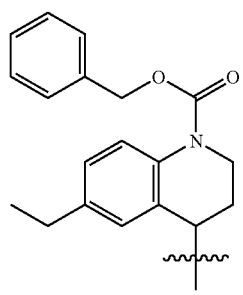 |
| 236 | 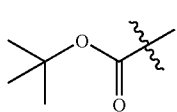 | 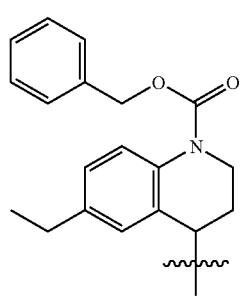 |
| 237 | 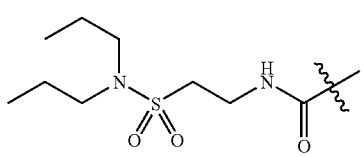 | 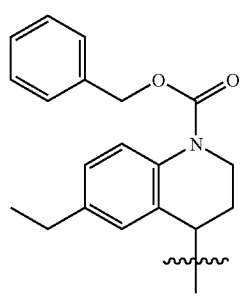 |

-continued
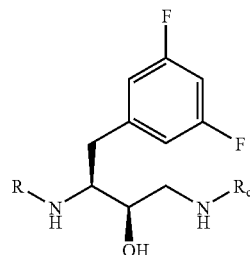
A
| Compound No. | R | $R_c$ |
|---|---|---|
| 238 | 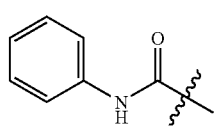 | 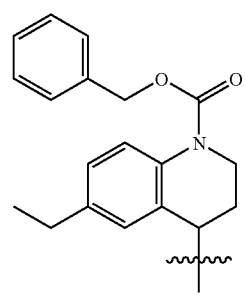 |
| 239 | 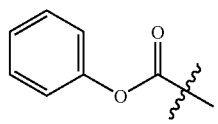 | 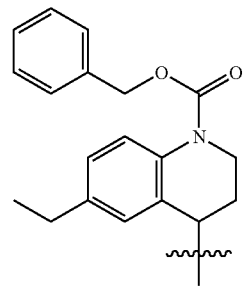 |
| 240 | 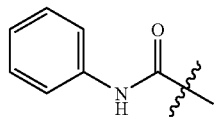 | 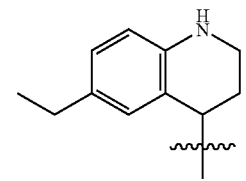 |
| 241 | 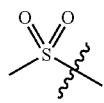 | 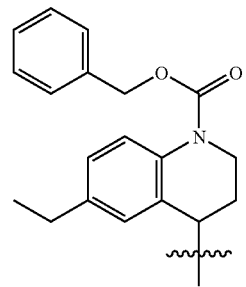 |

-continued
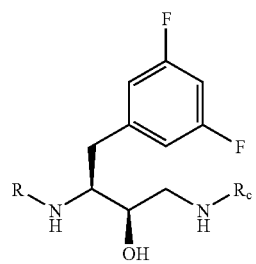
A
| Compound No. | R | $R_c$ |
|---|---|---|
| 242 | 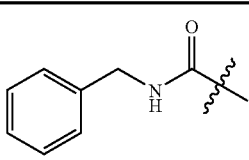 | 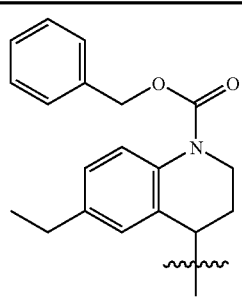 |
| 243 | 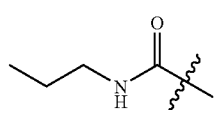 | 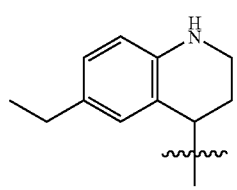 |
| 244 | 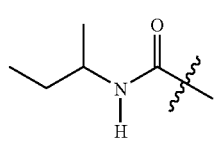 | 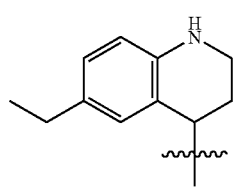 |
| 245 | 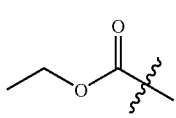 | 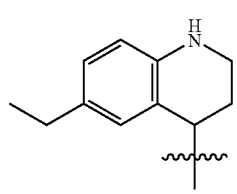 |
| 246 | 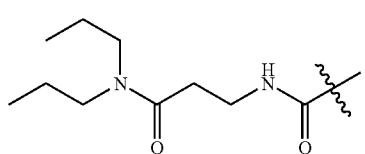 | 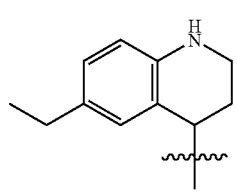 |
| 247 | 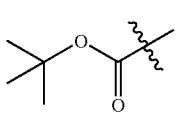 | 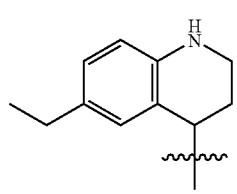 |

-continued
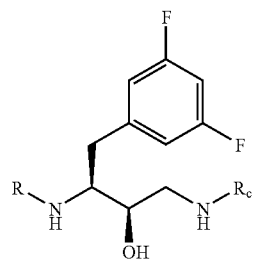
A
| Compound No. | R | R_c |
|---|---|---|
| 248 | 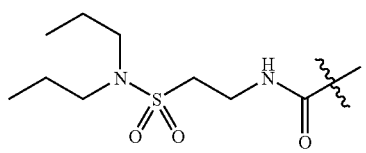 | 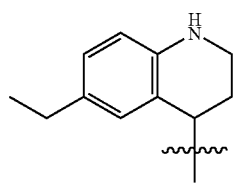 |
| 249 | 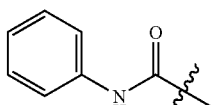 | 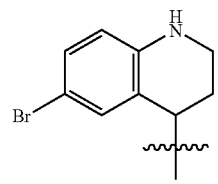 |
| 250 | 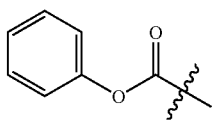 | 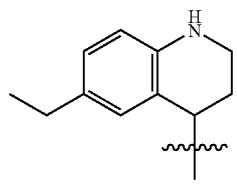 |
| 251 | 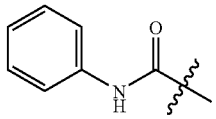 | 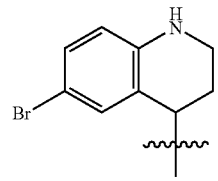 |
| 252 | 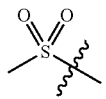 | 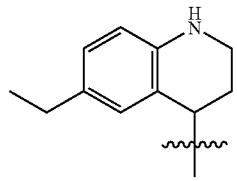 |
| 253 | 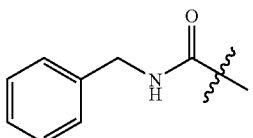 | 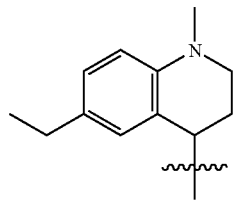 |

-continued
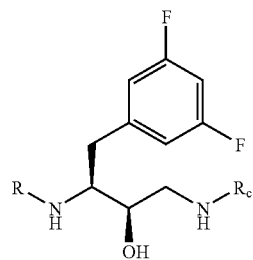
A
| Compound No. | R | $R_c$ |
|---|---|---|
| 254 | 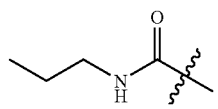 | 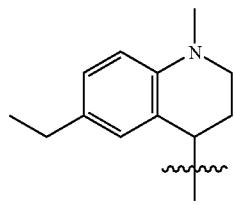 |
| 255 | 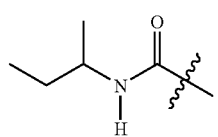 | 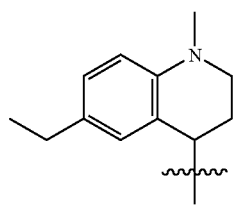 |
| 256 | 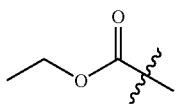 | 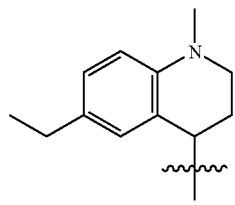 |
| 257 | 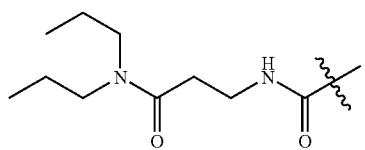 | 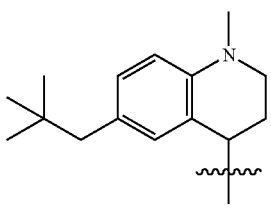 |
| 258 | 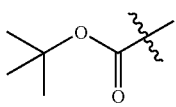 | 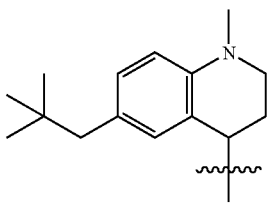 |
| 259 | 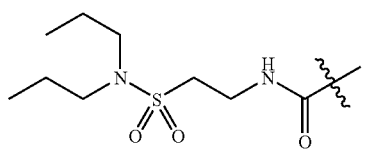 | 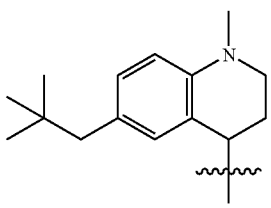 |

-continued
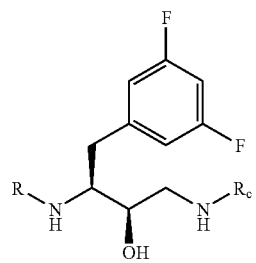
A
| Compound No. | R | R_c |
|---|---|---|
| 260 | 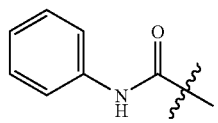 | 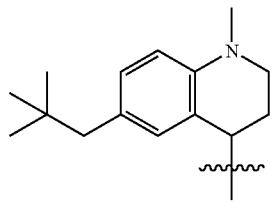 |
| 261 | 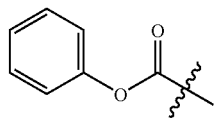 | 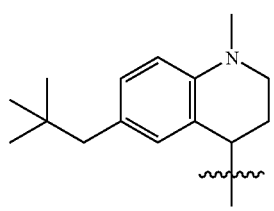 |
| 262 | 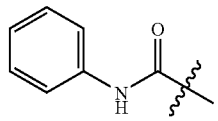 | 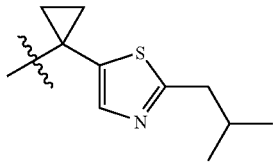 |
| 263 | 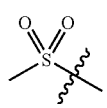 | 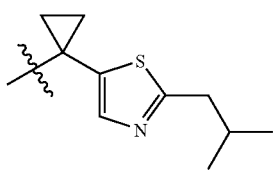 |
| 264 | 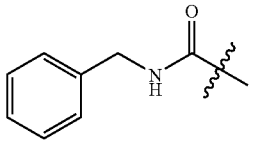 | 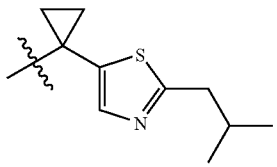 |
| 265 | 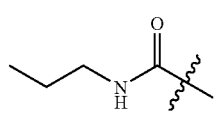 | 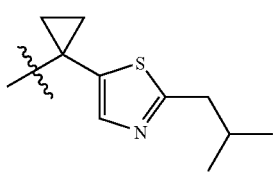 |

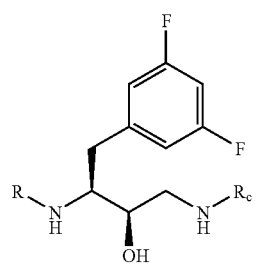
A
| Compound No. | R | R_c |
|---|---|---|
| 266 | 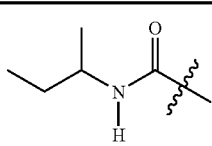 | 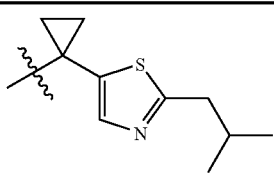 |
| 267 | 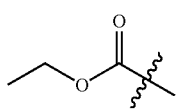 | 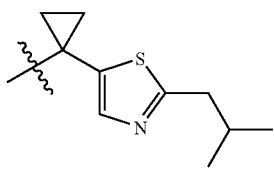 |
| 268 | 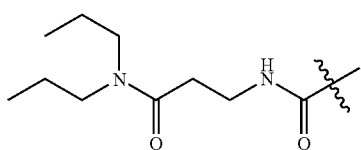 | 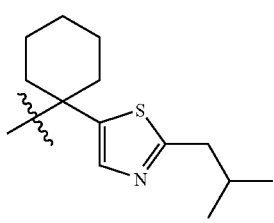 |
| 269 | 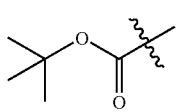 | 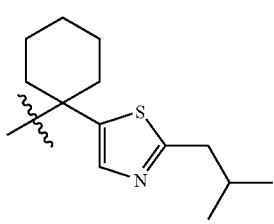 |
| 270 | 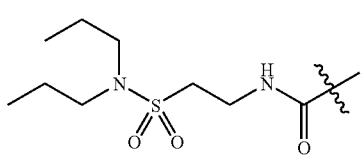 | 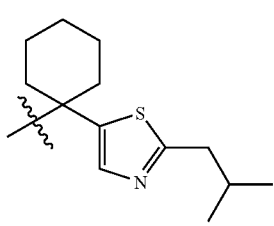 |
| 271 | 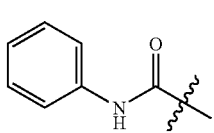 | 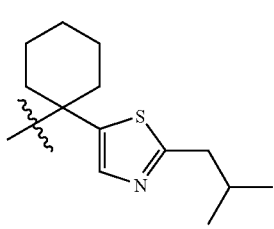 |

-continued
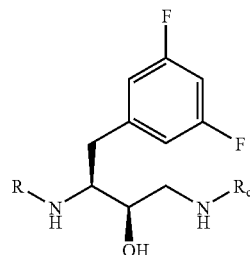
A
| Compound No. | R | $R_c$ |
|---|---|---|
| 272 | 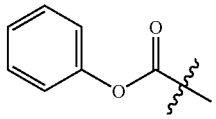 | 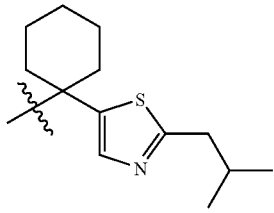 |
| 273 | 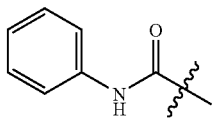 | 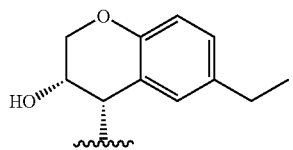 |
| 274 | 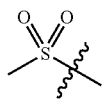 | 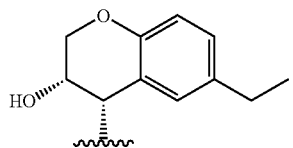 |
| 275 | 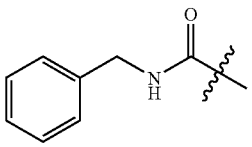 | 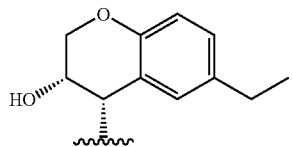 |
| 276 | 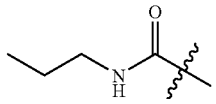 | 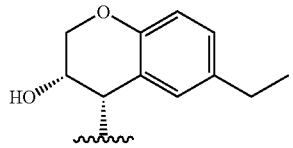 |
| 277 | 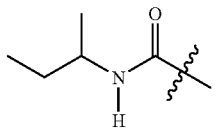 | 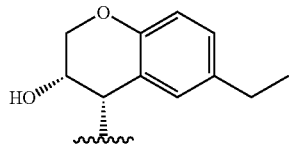 |
| 278 | 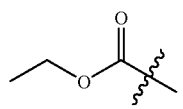 | 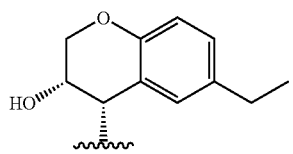 |

Example 5

The following compounds are prepared essentially according to the procedures outlined above and described in the above examples. The substituents R and $R_c$ are defined for formula A in the table.

| Compound No. | Structure/Name |
|---|---|
| 279 | 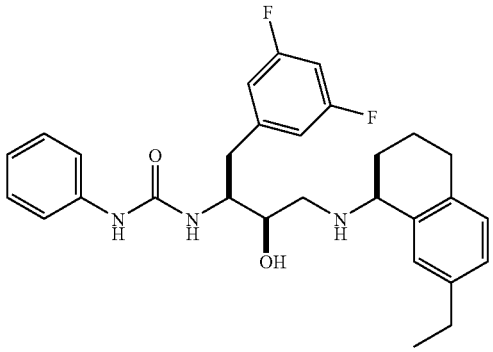  N-((1S,2R)-1-(3,5-difluorobenzyl)-3-{[(1S)-7-ethyl-1,2,3,4-tetrahydronaphthalen-1-yl]amino}-2-hydroxypropyl)-N'-phenylurea; |
| 280 | 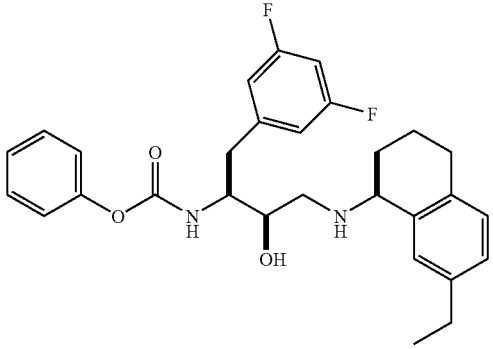  phenyl((1S,2R)-1-(3,5-difluorobenzyl)-3-{[(1S)-7-ethyl-1,2,3,4-tetrahydronaphthalen-1-yl]amino}-2-hydroxypropyl)carbamate; |
| 281 | 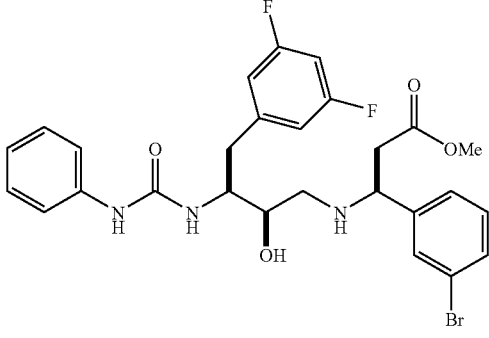  methyl (3S)-3-{[(2R,3S)-3-[(anilinocarbonyl)amino]-4-(3,5-difluorophenyl)-2-hydroxybutyl]amino}-3-(3-bromophenyl)propanoate; |

| Compound No. | Structure/Name |
|---|---|
| 282 | 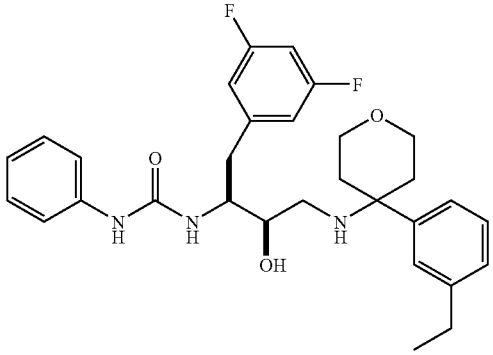<br>N-((1S,2R)-1-(3,5-difluorobenzyl)-3-{[4-(3-ethylphenyl)tetrahydro-2H-pyran-4-yl]amino}-2-hydroxypropyl)-N'-phenylurea; |
| 283 | 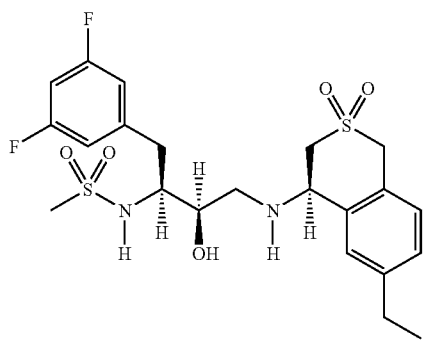<br>Mass spec. 503.1<br>N-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)methanesulfonamide; |
| 284 | 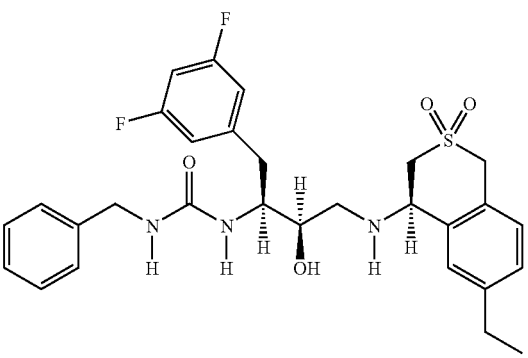<br>Mass spec. 558.1<br>N-benzyl-N'-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)urea; |

-continued

| Compound No. | Structure/Name |
|---|---|
| 285 | Mass spec. 544.1<br>N-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)-N'-phenylurea; |
| 286 | Mass spec. 510.1<br>N-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)-N'-propylurea; |
| 287 | Mass spec. 524.1<br>N-(sec-butyl)-N'-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)urea; |

| Compound No. | Structure/Name |
|---|---|
| 288 | Mass spec. 545.1<br>phenyl((1S,2R)-1-(3,5-difluorobenzyl)-3-{[(4R)-6-ethyl-2,2-dioxido-3,4-dihydro-1H-isothiochromen-4-yl]amino}-2-hydroxypropyl)carbamate; |
| 289 | Mass spec. 497.1<br>ethyl((1S,2R)-1-(3,5-difluorobenzyl)-3-{[(4R)-6-ethyl-2,2-dioxido-3,4-dihydro-1H-isothiochromen-4-yl]amino}-2-hydroxypropyl)carbamate; |
| 290 | N-{(1S,2R)-1-(3,5-difluorobenzyl)-3-[(6-ethyl-3,4-dihydro-2H-chromen-4-yl)amino]-2-hydroxypropyl}-N'-phenylurea; |

| Compound No. | Structure/Name |
|---|---|
| 291 | 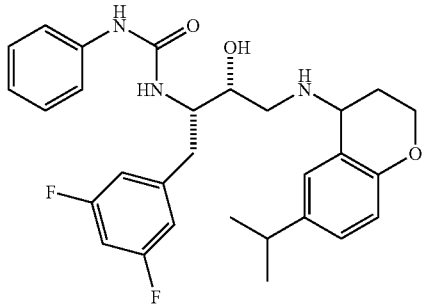<br>N-{(1S,2R)-1-(3,5-difluorobenzyl)-2-hydroxy-3-[(6-isopropyl-3,4-dihydro-2H-chromen-4-yl)amino]propyl}-N'-phenylurea; |
| 292 | 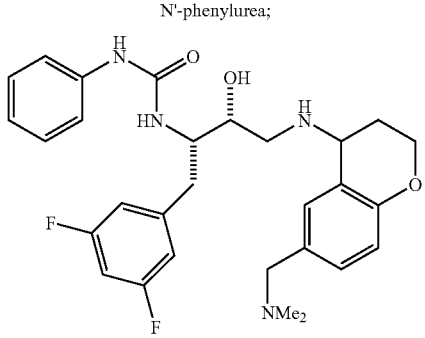<br>N-[(1S,2R)-1-(3,5-difluorobenzyl)-3-({6-[(dimethylamino)methyl]-3,4-dihydro-2H-chromen-4-yl}amino)-2-hydroxypropyl]-N'-phenylurea; |
| 293 | 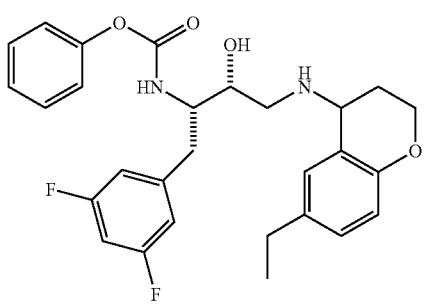<br>phenyl {(1S,2R)-1-(3,5-difluorobenzyl)-3-[(6-ethyl-3,4-dihydro-2H-chromen-4-yl)amino]-2-hydroxypropyl}carbamate; |
| 294 | 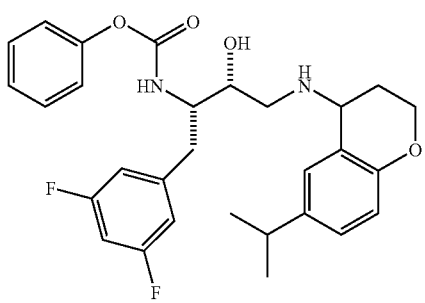<br>phenyl {(1S,2R)-1-(3,5-difluorobenzyl)-2-hydroxy-3-[(6-isopropyl-3,4-dihydro-2H-chromen-4-yl)amino]propyl}carbamate; |

| Compound No. | Structure/Name |
|---|---|
| 295 | 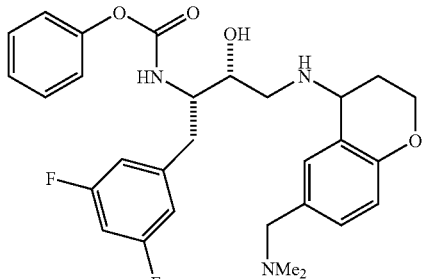<br>phenyl [(1S,2R)-1-(3,5-difluorobenzyl)-3-({6-[(dimethylamino)methyl]-3,4-dihydro-2H-chromen-4-yl}amino)-2-hydroxypropyl]carbamate; |
| 296 | 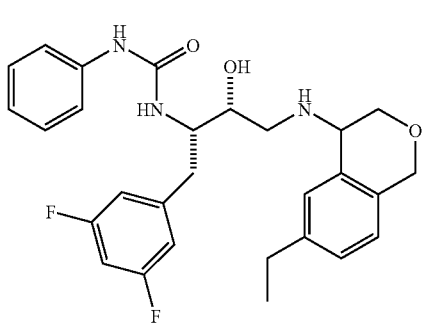<br>N-{(1S,2R)-1-(3,5-difluorobenzyl)-3-[(6-ethyl-3,4-dihydro-1H-isochromen-4-yl)amino]-2-hydroxypropyl}-N-phenylurea; |
| 297 | 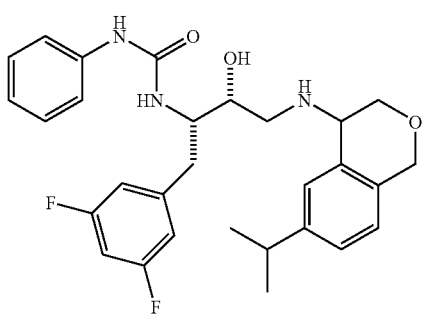<br>N-{(1S,2R)-1-(3,5-difluorobenzyl)-2-hydroxy-3-[(6-isopropyl-3,4-dihydro-1H-isochromen-4-yl)amino]propyl}-N'-phenylurea; |
| 298 | 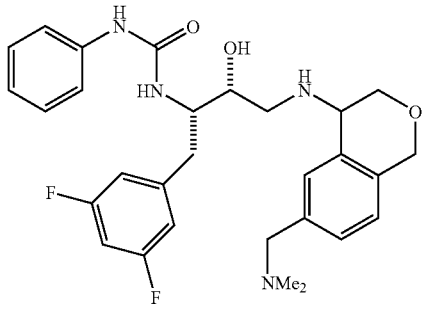<br>N-[(1S,2R)-1-(3,5-difluorobenzyl)-3-({6-[(dimethylamino)methyl]-3,4-dihydro-1H-isochromen-4-yl}amino)-2-hydroxypropyl]-N'-phenylurea; |

| Compound No. | Structure/Name |
|---|---|
| 299 | 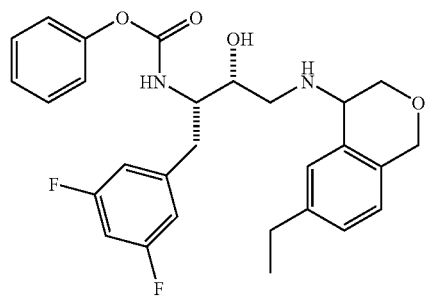<br>phenyl {(1S,2R)-1-(3,5-difluorobenzyl)-3-[(6-ethyl-3,4-dihydro-1H-isochromen-4-yl)amino]-2-hydroxypropyl}carbamate; |
| 300 | 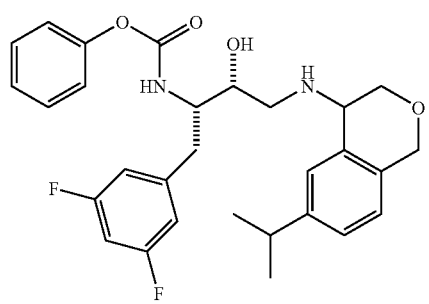<br>phenyl {(1S,2R)-1-(3,5-difluorobenzyl)-2-hydroxy-3-[(6-isopropyl-3,4-dihydro-1H-isochromen-4-yl)amino]propyl}carbamate; |
| 301 | 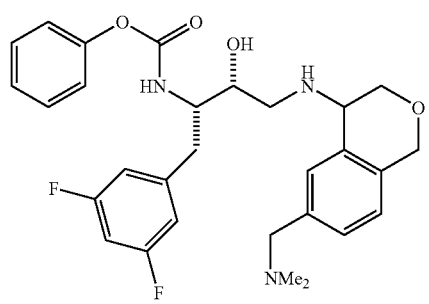<br>phenyl [(1S,2R)-1-(3,5-difluorobenzyl)-3-({6-[(dimethylamino)methyl]-3,4-dihydro-1H-isochromen-4-yl}amino)-2-hydroxypropyl]carbamate; |
| 302 | 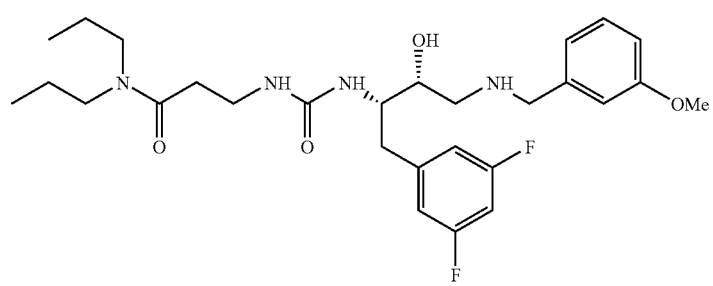<br>$N^3$-[({(1S,2R)-1-(3,5-difluorobenzyl)-2-hydroxy-3-[(3-methoxybenzyl)amino]propyl}amino)carbonyl]-$N^1$,$N^1$-dipropyl-b-alaninamide; |

| Compound No. | Structure/Name |
|---|---|
| 303 | 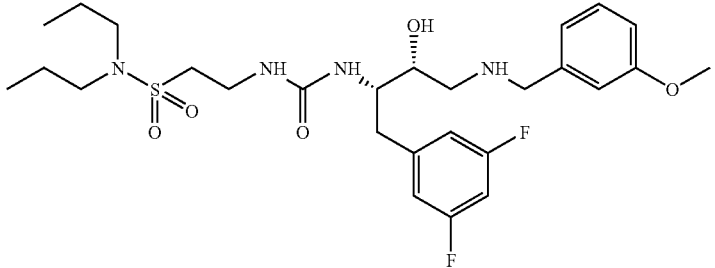<br>2-{[({(1S,2R)-1-(3,5-difluorobenzyl)-2-hydroxy-3-[(3-methoxybenzyl)amino]propyl}amino)carbonyl]amino}-N,N-dipropylethanesulfonamide. |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Unless defined otherwise, all scientific and technical terms used herein have the same meaning as commonly understood by one of skill in the art to which this invention belongs.

All patents and publications referred to herein are hereby incorporated by reference for all purposes.

The invention has been described with reference to various specific and preferred embodiments and techniques. However, it should be understood that many variations and modifications may be made while remaining within the spirit and scope of the invention.

What is claimed is:

1. A compound of the formula:

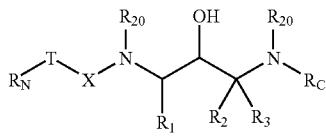

or pharmaceutically acceptable salts or esters thereof;
wherein X is —(C=O)—, —(C=S)—, or —(C=N—Z),
wherein Z is $R_{20}$ or —$OR_{20}$;
T is $NR_{20}$;
wherein each $R_{20}$ is independently H, —CN, $C_1$-$C_6$ alkyl $C_2$-$C_6$alkenyl, $C_1$-$C_6$ haloalkyl or $C_4$-$C_7$ cycloalkyl, with the proviso that when Z is $R_{20}$ or —$OR_{20}$, $R_{20}$ is not —CN;
wherein $R_1$ is —$(CH_2)_{1-2}$—$S(O)_{0-2}$—($C_1$-$C_6$ alkyl), or $C_1$-$C_{10}$ alkyl optionally substituted with 1, 2, or 3 groups independently selected from halogen, —OH, =O, —SH, —C≡N, —$CF_3$, —$C_1$-$C_3$ alkoxy, amino, mono or dialkylamino, —N(R)C(O)R'—, —OC(=O)-amino and —OC(=O)-mono- or dialkylamino, or $C_2$-$C_6$ alkenyl or $C_2$-$C_6$ alkynyl, each of which is optionally substituted with 1, 2, or 3 groups independently selected from halogen, —OH, —SH, —C≡N, —$CF_3$, $C_1$-$C_3$ alkoxy, amino, and mono- or dialkylamino, or aryl, heteroaryl, heterocyclyl, —$C_1$-$C_6$ alkyl-aryl, —$C_1$-$C_6$ alkyl-heteroaryl, or —$C_1$-$C_6$ alkyl-heterocyclyl, where the ring portions of each are optionally substituted with 1, 2, 3, or 4 groups independently selected from halogen, —OH, —SH, —C≡N, —$NR_{105}R'_{105}$, —$CO_2R$, —N(R)COR', —N(R)$SO_2$R', —C(=O)—($C_1$-$C_4$) alkyl, —$SO_2$-amino, —$SO_2$-mono or dialkylamino, —C(=O)-amino, —C(=O)-mono or dialkylamino, —$SO_2$—($C_1$-$C_4$) alkyl, or $C_1$-$C_6$ alkoxy optionally substituted with 1, 2, or 3 halogens, or $C_3$-$C_7$ cycloalkyl optionally substituted with 1, 2, or 3 groups independently selected from halogen, —OH, —SH, —C≡N, —$CF_3$, $C_1$-$C_3$ alkoxy, amino, —$C_1$-$C_6$ alkyl and mono- or dialkylamino, or $C_1$-$C_{10}$ alkyl optionally substituted with 1, 2, or 3 groups independently selected from halogen, —OH, —SH, —C≡N, —$CF_3$, —$C_1$-$C_3$ alkoxy, amino, mono- or dialkylamino and —$C_1$-$C_3$ alkyl, or $C_2$-$C_{10}$ alkenyl or $C_2$-$C_{10}$ alkynyl each of which is optionally substituted with 1, 2, or 3 groups independently selected from halogen, —OH, —SH, —C≡N, —$CF_3$, $C_1$-$C_3$ alkoxy, amino, $C_1$-$C_6$ alkyl and mono- or dialkylamino; and the heterocyclyl group is optionally further substituted with oxo;

R and R' independently are hydrogen, $C_1$-$C_{10}$ alkyl, $C_1$-$C_{10}$ alkylaryl or $C_1$-$C_{10}$ alkylheteroaryl;

wherein Rc is (I) —[—$(CH_2)_{(0-8)}$—(CH)($alkyl_1$) ($alkyl_2$)], where $alkyl_1$ and $alkyl_2$ are stratight or branched $C_{2-10}$ alkanyl, alkenyl or alkynyl, and wherein $alkyl_1$ and $alkyl_2$ attach to the same or different methylene carbon with the remaining open methylene valences occupied by hydrogen, thus forming a branched alkyl chain having between 8 and 20 carbon atoms in total;

the alkyl groups, $alkyl_1$ and $alkyl_2$ being optionally substituted with one, two or three substituents selected from the group consisting of $C_1$-$C_3$ alkyl, halogen, —OH, —SH, —C≡N, —$CF_3$, $C_1$-$C_3$ alkoxy, —O-phenyl, —C(O)$C_1$-$C_3$ alkyl, —$NR_{1-a}R_{1-b}$ where $R_{1-a}$ and $R_{1-b}$ are —H or $C_1$-$C_6$ alkyl, —OC=O $NR_{1-a}R_{1-b}$, —S(=O)$_{0-2}$, —$NR_{1-a}$C=O $NR_{1-a}R_{1-b}$, —C=O $NR_{1-a}R_{1-b}$, and —S(=O)$_2$ $NR_{1-a}R_{1-b}$;

(II) —(C(Rc-x)(Rc-y))$_{(0-4)}$-Rc-cycle wherein each Rc-x and Rc-y is independently chosen from:

H $C_1$-$C_6$ alkyl $C_1$-$C_6$ alkoxy $C_2$-$C_6$ alkenyl or alkynyl

—$(CH_2)_{0-4}$-Rc-cycle where Rc-cycle is as defined below or Rc-x and Rc-y may be taken together with the methylene carbon to which they jointly attach to form a spirocyclic ring of 3 to 7 atoms comprising carbon and up to 2 of O, S(O)$_{(0-2)}$ and $NR_{a'}$, wherein is $R_{a'}$ is H or $C_{1-4}$ alkyl;

wherein the spirocyclic ring may be fused to another ring to provide a bicyclic ring system comprising carbon and up to 2 of O, S(O)$_{(0-2)}$ and $NR_{a'}$, and comprising up to 9 atoms in total including, Rc-cycle is aryl, heteroaryl, cycloalkyl or a fused-ring system consisting of no more than three rings where each of the rings is the same or different and is an aryl, heteroaryl, or cycloalkyl ring wherein Rc-cycle is optionally substituted with up to four substituents independently selected from:

(1) $C_1$-$C_6$ alkyl optionally substituted with one, two or three substituents selected from the group consisting of $C_1$-$C_3$ alkyl, halogen, —OH, —SH, —C≡N, —$CF_3$, $C_1$-$C_3$ alkoxy, and —$NR_{1-a}R_{1-b}$, (2) $C_2$-$C_6$ alkenyl or alkynyl with one or two unsaturated bonds, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$, (3) halogen, (4) $C_1$-$C_6$ alkoxy, (5) —$C_1$-$C_6$ alkoxy optionally substituted with one, two, or three of —F, (6) —$NR_{N-6}R_{N-7}$ where $R_{N-6}$ and $R_{N-7}$ are the same or different and are selected from the group consisting of:
  (a) —H,
  (b) —$C_1$-$C_6$ alkyl optionally substituted with one substitutent selected from the group consisting of:
    (i) —OH, and
    (ii) —$NH_2$,
  (c) —$C_1$-$C_6$ alkyl optionally substituted with one to three —F, —Cl, —Br, or —I,
  (d) —$C_3$-$C_7$ cycloalkyl,
  (e) —($C_1$-$C_2$ alkyl)-($C_3$-$C_7$ cycloalkyl),
  (f) —($C_1$-$C_6$ alkyl)-O—($C_1$-$C_3$ alkyl),
  (g) —$C_2$-$C_6$ alkenyl with one or two double bonds,
  (h) —$C_2$-$C_6$ alkynyl with one or two triple bonds,
  (i) —$C_1$-$C_6$ alkyl chain with one double bond and one triple bond,
  (j) aryl, and
  (k) heteroaryl,
(7) —OH,
(8) —C≡N,
(9) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$,
(10) —CO—($C_1$-$C_4$ alkyl),
(11) —$SO_2$—$NR_{1-a}R_{1-b}$,
(12) —CO—$NR_{1-a}R_{1-b}$,
(13) —$SO_2$—($C_1$-$C_4$ alkyl),
and when there is a saturated carbon atom in Rc-cycle
(14) oxo,
(15) oxime
(16) ketal rings of 5 to 7 members, and
(17) a spirocyclic ring having from 3 to 7 atoms comprising carbon and when the ring size is 4-7 atoms optionally up to 2 of O, $S(O)_{(0-2)}$ and $NR_{a'}$
(III) —$(CR_{C-x}R_{C-y})_{0-4}$-aryl-aryl,
(IV) —$(CR_{C-x}R_{C-y})_{0-4}$-aryl-heteroaryl,
(V) —$(CR_{C-x}R_{C-y})_{0-4}$-heteroaryl-aryl,
(VI) —$(CR_{C-x}R_{C-y})_{0-4}$-heteroaryl-heteroaryl,
(VII) —$(CR_{C-x}R_{C-y})_{0-4}$-aryl-heterocycle,
(VIII) —$(CR_{C-x}R_{C-y})_{0-4}$-heteroaryl-heterocycle,
(IX) —$(CR_{C-x}R_{C-y})_{0-4}$-heterocycle-aryl,
(X) —$(CR_{C-x}R_{C-y})_{0-4}$-heterocycle-heteroaryl,
(XI) —$(CR_{C-x}R_{C-y})_{0-4}$-heterocycle-heterocycle,
(XII) —$[C(R_{C-1})(R_{C-2})]_{1-3}$—$[CO]_{0-1}$—N—$(R_{C-3})_2$ where each $R_{C-1}$ is the same or different and is selected from the group consisting of H, $C_{1-4}$ alkyl and $C_{1-4}$ alkoxy where each $R_{C-2}$ and $R_{C-3}$ is independently selected from
  (A) —$C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O— phenyl, and —$NR_{1-a}R_{1-b}$,
  (B) $C_2$-$C_6$ alkenyl or alkynyl with one or two unsaturated bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
  (C) —$(CH_2)_{1-2}$—$S(O)_{0-2}$—($C_1$-$C_6$ alkyl),
  (D) —$(CH_2)_{0-4}$—$C_3$-$C_7$ cycloalkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O— phenyl, —$NR_{1-a}R_{1-b}$,
  (E) —$(CH_2)_{0-4}$-5-7 membered heterocycle optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O— phenyl, oxo, and —$NR_{1-a}R_{1-b}$,
(XIII) —$CH(aryl)_2$ where each aryl is the same or different,
(XIV) —$CH(heteroaryl)_2$ where each heteroaryl is the same or different and are as defined above,
(XVIII) —CH(aryl)(heteroaryl);
wherein $R_N$ is $R'_{100}$, —$(CRR')_{1-6}R'_{100}$, —$(CRR')_{0-6}R_{100}$, —$(CRR')_{1-6}$—O—$R'_{100}$, —$(CRR')_{1-6}$—S—$R'_{100}$, —$(CRR')_{1-6}$—C(=O)—$R_{100}$, —$(CRR')_{1-6}$—$SO_2$—$R_{100}$, —$(CRR')_{1-6}$—$NR_{100}$—$R'_{100}$ or —$SO_2R'_{100}$, with the proviso that when $R_N$ is —$SO_2R'_{100}$, X is not —$S(=O)_n$— or —C(=S)—; wherein
$R_{100}$ and $R'_{100}$ are independently represent aryl, heteroaryl, -aryl-W-aryl, -aryl-W-heteroaryl, -aryl-W-heterocyclyl, -heteroaryl-W-aryl, -heteroaryl-W-heteroaryl, -heteroaryl-W-heterocyclyl, -heterocyclyl-W-aryl, -heterocyclyl-W-heteroaryl, -heterocyclyl-W-heterocyclyl, —CH [$(CH_2)_{0-2}$—O—$R_{150}$]—$(CH_2)_{0-2}$-aryl, —CH [$(CH_2)_{0-2}$—O—$R_{150}$]—$(CH_2)_{0-2}$-heterocyclyl or —CH[$(CH_2)_{0-2}$—O—$R_{150}$]—$(CH_2)_{0-2}$-heteroaryl, where the ring portions of each are optionally substituted with 1, 2, or 3 groups independently selected from
  —OR, —$NO_2$, halogen, —C≡N, —$OCF_3$, —$CF_3$, —$(CH_2)_{0-4}$—O—P(=O)(OR)(OR'), —$(CH_2)_{0-4}$—CO—$NR_{105}R'_{105}$, —$(CH_2)_{0-4}$—O—$(CH_2)_{0-4}$—$CONR_{102}R_{102}'$, —$(CH_2)_{0-4}$—CO—($C_1$-$C_{12}$ alkyl), —$(CH_2)_{0-4}$—CO—($C_2$-$C_{12}$ alkenyl), —$(CH_2)_{0-4}$—CO—($C_2$-$C_{12}$ alkynyl), —$(CH_2)_{0-4}$—CO—$(CH_2)_{0-4}$—($C_3$-$C_7$ cycloalkyl), —$(CH_2)_{0-4}$—$R_{110}$, —$(CH_2)_{0-4}$—$R_{120}$, —$(CH_2)_{0-4}$—$R_{130}$, —$(CH_2)_{0-4}$—CO—$R_{110}$, —$(CH_2)_{0-4}$—CO—$R_{120}$, —$(CH_2)_{0-4}$—CO—$R_{130}$, —$(CH_2)_{0-4}$—CO—$R_{140}$, —$(CH_2)_{0-4}$—CO—O—$R_{150}$, —$(CH_2)_{0-4}$—$SO_2$—$NR_{105}R'_{105}$, —$(CH_2)_{0-4}$—SO—($C_1$-$C_8$ alkyl), —$(CH_2)_{0-4}$—$SO_2$—($C_1$-$C_{12}$ alkyl), —$(CH_2)_{0-4}$—$SO_2$—$(CH_2)_{0-4}$—($C_3$-$C_7$ cycloalkyl), —$(CH_2)_{0-4}$—$N(R_{150})$—CO—O—$R_{150}$, —$(CH_2)_{0-4}$—$N(R_{150})$—CO—$N(R_{150})_2$, —$(CH_2)_{0-4}$—$N(R_{150})$—CS—$N(R_{150})_2$, —$(CH_2)_{0-4}$—$N(R_{150})$—CO—$R_{105}$, —$(CH_2)_{0-4}$—$NR_{105}R'_{105}$, —$(CH_2)_{0-4}$—$R_{140}$, —$(CH_2)_{0-4}$—O—CO—($C_1$-$C_6$ alkyl), —$(CH_2)_{0-4}$—O—P(O)—(O—$R_{110})_2$, —$(CH_2)_{0-4}$—O—CO—N$(R_{150})_2$, —$(CH_2)_{0-4}$—O—CS—$N(R_{150})_2$, —$(CH_2)_{0-4}$—O—$(R_{150})$, —$(CH_2)_{0-4}$—O—$R_{150}'$-COOH, —$(CH_2)_{0-4}$—S—$(R_{150})$, —$(CH_2)_{0-4}$—N$(R_{150})$—$SO_2$—$R_{105}$, —$(CH_2)_{0-4}$—$C_3$-$C_7$ cycloalkyl, ($C_2$-$C_{10}$)alkenyl, or ($C_2$-$C_{10}$)alkynyl, or $R_{100}$ is $C_1$-$C_{10}$ alkyl optionally substituted with 1, 2, or 3 $R_{115}$ groups, or $R_{100}$ is —($C_1$-$C_6$ alkyl)—O—$C_1$-$C_6$ alkyl) or —($C_1$-$C_6$ alkyl)—S—($C_1$-$C_6$ alkyl), each $C_1$-$C_6$ alkyl is optionally substituted with 1, 2, or 3 $R_{115}$ groups, or $R_{100}$ is $C_3$-$C_8$ cycloalkyl optionally substituted with 1, 2, or 3 $R_{115}$ groups;

W is a bond —$(CH_2)_{1-4}$—, —O—, —$S(O)_{0-2}$—, —$N(R_{135})$—, —CR(OH)— or —C(O)—;

$R_{102}$ and $R_{102}'$ independently are hydrogen, or
  $C_1$-$C_{10}$ alkyl optionally substituted with 1, 2, or 3 groups that are independently halogen, aryl or —$R_{110}$;

$R_{105}$ and $R'_{105}$ independently are —H, —$R_{110}$, —$R_{120}$, $C_3$-$C_7$ cycloalkyl, —($C_1$-$C_2$ alkyl)-($C_3$-$C_7$ cycloalkyl), —($C_1$-$C_6$ alkyl)—O—($C_1$-$C_3$ alkyl), $C_2$-$C_6$ alkenyl, $C_2$-$C_6$ alkynyl, or $C_1$-$C_6$ alkyl chain with one double bond and one triple bond, $C_1$-$C_6$ alkyl optionally substituted with —OH or —$NH_2$; or $C_1$-$C_6$ alkyl optionally substituted with 1, 2, or 3 halogen, or $R_{105}$ and $R'_{105}$ together with the atom to which they are attached form a 3 to 7 membered carbocylic ring, where one member is optionally a heteratom selected from —O—, —$S(O)_{0-2}$—, —$N(R_{135})$—, the ring being optionally substituted with 1, 2 or three $R_{140}$ groups;

$R_{115}$ at each occurrence is independently halogen, —OH, —$CO_2R_{102}$, —$C_1$-$C_6$ thioalkoxy, —$CO_2$-phenyl, —$NR_{105}R'_{135}$, —$SO_2$—($C_1$-$C_8$ alkyl), —C(=O)$R_{180}$, $R_{180}$, —$CONR_{105}R'_{105}$, —$SO_2NR_{105}R'_{105}$, —NH—CO—($C_1$-$C_6$ alkyl), —NH—C(=O)—OH, —NH—C(=O)—OR, —NH—C(=O)—O-phenyl, —O—C(=O)—($C_1$-$C_6$ alkyl), —O—C(=O)-amino, —O—C(=O)-mono- or dialkylamino, —O—C(=O)-phenyl, —O—($C_1$-$C_6$ alkyl)—$CO_2H$, —NH—$SO_2$—($C_1$-$C_6$ alkyl), $C_1$-$C_6$ alkoxy or $C_1$-$C_6$ haloalkoxy;

$R_{135}$ is $C_1$-$C_6$ alkyl, $C_2$-$C_6$ alkenyl, $C_2$-$C_6$ alkynyl, $C_3$-$C_7$ cycloalkyl, —$(CH_2)_{0-2}$-(aryl), —$(CH_2)_{0-2}$-(heteroaryl), or —$(CH_2)_{0-2}$-(heterocyclyl);

$R_{140}$ is heterocyclyl optionally substituted with 1, 2, 3, or 4 groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, and =O;

$R_{150}$ is hydrogen, $C_3$-$C_7$ cycloalkyl, —($C_1$-$C_2$ alkyl)-($C_3$-$C_7$ cycloalkyl), $C_2$-$C_6$ alkenyl, $C_2$-$C_6$ alkynyl, $C_1$-$C_6$ alkyl with one double bond and one triple bond, —$R_{110}$, —$R_{120}$, or $C_1$-$C_6$ alkyl optionally substituted with 1, 2, 3, or 4 groups independently selected from —OH, —$NH_2$, $C_1$-$C_3$ alkoxy, $R_{110}$, and halogen;

$R_{150}'$ is $C_3$-$C_7$ cycloalkyl, —($C_1$-$C_3$ alkyl)-($C_3$-$C_7$ cycloalkyl), $C_2$-$C_6$ alkenyl, $C_2$-$C_6$ alkynyl, $C_1$-$C_6$ alkyl with one double bond and one triple bond, —$R_{110}$, —$R_{120}$, or $C_1$-$C_6$ alkyl optionally substituted with 1, 2, 3, or 4 groups independently selected from —OH, —$NH_2$, $C_1$-$C_3$ alkoxy, $R_{110}$, and halogen;

$R_{180}$ is selected from morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl, each of which is optionally substituted with 1, 2, 3, or 4 groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$) alkyl, and =O;

$R_{110}$ is aryl optionally substituted with 1 or 2 $R_{125}$ groups;

$R_{125}$ at each occurrence is independently halogen, amino, mono- or dialkylamino, —OH, —C≡N, —$SO_2$—$NH_2$, —$SO_2$—NH—$C_1$-$C_6$ alkyl, —$SO_2$—N($C_1$-$C_6$ alkyl)$_2$, —$SO_2$—($C_1$-$C_4$ alkyl), —CO—$NH_2$, —CO—NH—$C_1$-$C_6$ alkyl, or —CO—N($C_1$-$C_6$ alkyl)$_2$, or $C_1$-$C_6$ alkyl, $C_2$-$C_6$ alkenyl or $C_2$-$C_6$ alkynyl, wherein each $C_1$-$C_6$alkyl, $C_2$-$C_6$ alkenyl or $C_2$-$C_6$ alkynyl is optionally substituted with 1, 2, or 3 groups that are independently selected from $C_1$-$C_3$ alkyl, halogen, —OH, —SH, —C≡N, —$CF_3$, $C_1$-$C_3$ alkoxy, amino, and mono- and dialkylamino, or $C_1$-$C_6$ alkoxy optionally substituted with one, two or three halogens;

$R_{120}$ is heteroaryl optionally substituted with 1 or 2 $R_{125}$ groups; and $R_{130}$ is heterocyclyl optionally substituted with 1 or 2 $R_{125}$ groups;

$R_2$ is selected from the group consisting of H; $C_1$-$C_6$ alkyl, optionally substituted with 1, 2, or 3 substituents independently selected from the group consisting of $C_1$-$C_3$ alkyl, halogen, —OH, —SH, —C≡N, —$CF_3$, $C_1$-$C_3$ alkoxy, and —$NR_{1-a}R_{1-b}$; wherein $R_{1-a}$ and $R_{1-b}$ are —H or $C_1$-$C_6$ alkyl; —$(CH_2)_{0-4}$-aryl; —$(CH_2)_{0-4}$-heteroaryl; $C_2$-$C_6$ alkenyl; $C_2$-$C_6$ alkynyl; —$CONR_{N-2}R_{N-3}$; —$SO_2NR_{N-2}R_{N-3}$; —$CO_2H$; and —$CO_2$—($C_1$-$C_4$ alkyl);

$R_3$ is selected from the group consisting of H; $C_1$-$C_6$ alkyl optionally substituted with 1, 2, or 3 substituents independently selected from the group consisting of $C_1$-$C_3$ alkyl, halogen, —OH, —SH, —C≡N, —$CF_3$, $C_1$-$C_3$ alkoxy, and —$NR_{1-a}R_{1-b}$; —$(CH_2)_{0-4}$-aryl; —$(CH_2)_{0-4}$-heteroaryl; $C_2$-$C_6$ alkenyl; $C_2$-$C_6$ alkynyl; —CO—$NR_{N-2}R_{N-3}$; —$SO_2$—$NR_{N-2}R_{N-3}$; —$CO_2H$; and —CO—O—($C_1$-$C_4$ alkyl);

wherein $R_{N-2}$ and $R_{N-3}$ at each occurrence are independently selected from the group consisting of —$C_1$-$C_8$ alkyl optionally substituted with 1, 2, or 3 groups independently selected from the group consisting of —OH, —$NH_2$, phenyl and halogen; —$C_3$-$C_8$ cycloalkyl; —($C_1$-$C_2$ alkyl)-($C_3$-$C_8$ cycloalkyl); —($C_1$-$C_6$ alkyl)—O—($C_1$-$C_3$ alkyl); —$C_2$-$C_6$ alkenyl; —$C_2$-$C_6$ alkynyl; —$C_1$-$C_6$ alkyl chain with one double bond and one triple bond; aryl; heteroaryl; heterocycloalkyl; or $R_{N-2}$, $R_{N-3}$ and the nitrogen to which they are attached form a 5, 6, or 7 membered heterocycloalkyl or heteroaryl group, wherein said heterocycloalkyl or heteroaryl group is optionally fused to a benzene, pyridine, or pyrimidine ring, and said groups are unsubstituted or substituted with 1, 2, 3, 4, or 5 groups that at each occurrence are independently $C_1$-$C_6$ alkyl, $C_1$-$C_6$ alkoxy, halogen, halo $C_1$-$C_6$ alkyl, halo $C_1$-$C_6$ alkoxy, —CN, —$NO_2$, —$NH_2$, NH($C_1$-$C_6$ alkyl), N($C_1$-$C_6$ alkyl) ($C_1$-$C_6$ alkyl), —OH, —C(O)$NH_2$, —C(O)NH ($C_1$-$C_6$ alkyl), —C(O)N($C_1$-$C_6$ alkyl) ($C_1$-$C_6$ alkyl), $C_1$-$C_6$ alkoxy $C_1$-$C_6$ alkyl, $C_1$-$C_6$ thioalkoxy, and $C_1$-$C_6$ thioalkoxy $C_1$-$C_6$ alkyl; or $R_2$, $R_3$ and the carbon to which they are attached form a carbocycle of three thru seven carbon atoms, wherein one carbon atom is optionally replaced by a group selected from —O—, —S—, —$SO_2$—, or —$NR_{N-2}$—.

2. A compound according to claim 1 of the formula

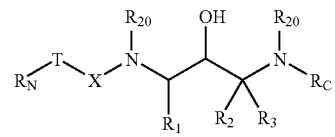

or a pharmaceutically acceptable salt or ester thereof wherein $R_C$ is selected from —$(CH_2)_{0-3}$—($C_3$-$C_8$) cycloalkyl wherein the cycloalkyl is optionally substituted with 1, 2, or 3 groups independently selected from —$R_{205}$; and —$CO_2$—($C_1$-$C_4$ alkyl); —$(CR_{245}R_{250})_{0-4}$-aryl; —$(CR_{245}R_{250})_{0-4}$-heteroaryl; —$(CR_{245}R_{250})_{0-4}$-heterocycloalkyl; —$(CR_{245}R_{250})_{0-4}$-aryl-heteroaryl; —$(CR_{245}R_{250})_{0-4}$-aryl-heterocycloalkyl; —$(CR_{245}R_{250})_{0-4}$-aryl-aryl;

—$(CR_{245}R_{250})_{0-4}$-heteroaryl-aryl; —$(CR_{245}R_{250})_{0-4}$-heteroaryl-heterocycloalkyl; —$(CR_{245}R_{250})_{0-4}$-heteroaryl-heteroaryl; —$CHR_{245}$-$CHR_{250}$-aryl; —$(CR_{245}R_{250})_{0-4}$-heterocycloalkyl-heteroaryl; —$(CR_{245}R_{250})_{0-4}$-heterocycloalkyl-heterocycloalkyl; —$(CR_{245}R_{250})_{0-4}$-heterocycloalkyl-aryl; a monocyclic or bicyclic ring of 5, 6, 7 8, 9, or 10 carbons fused to 1 or 2 aryl, heteroaryl, or heterocycloalkyl groups; wherein 1, 2 or 3 carbons of the monocyclic or bicyclic ring are optionally replaced with —NH—, —$N(CO)_{0-1}R_{215}$—, —$N(CO)_{0-1}$—$R_{220}$—, —O—, or —$S(=O)_{0-2}$—, and wherein the monocyclic or bicyclic ring is optionally substituted with 1, 2 or 3 groups that are independently —$R_{205}$, —$R_{245}$, —$R_{250}$ or =O;

and —$C_2$-$C_6$ alkenyl optionally substituted with 1, 2, or 3 $R_{205}$ groups;

wherein each aryl or heteroaryl group attached directly or indirectly to the —$(CR_{245}R_{250})_{0-4}$ group is optionally substituted with 1, 2, 3 or 4 $R_{200}$ groups;

wherein each heterocycloalkyl attached directly or indirectly to the —$(CR_{245}R_{250})_{0-4}$ group is optionally substituted with 1, 2, 3, or 4 $R_{210}$;

$R_{200}$ at each occurrence is independently selected from —$C_1$-$C_6$ alkyl optionally substituted with 1, 2, or 3 $R_{205}$ groups; —OH; —$NO_2$; -halogen; —C≡N; —$(CH_2)_{0-4}$—CO—$NR_{220}R_{225}$; —$(CH_2)_{0-4}$—CO—$(C_1$-$C_8$ alkyl); —$(CH_2)_{0-4}$—CO—$(C_2$-$C_8$ alkenyl); —$(CH_2)_{0-4}$—CO—$(C_2$-$C_8$ alkynyl); —$(CH_2)_{0-4}$—CO—$(C_3$-$C_7$ cycloalkyl); —$(CH_2)_{0-4}$—$(CO)_{0-1}$-aryl; —$(CH_2)_{0-4}$—$(CO)_{0-1}$-heteroaryl; —$(CH_2)_{0-4}$—$(CO)_{0-1}$-heterocycloalkyl; —$(CH_2)_{0-4}$—$CO_2R_{215}$; —$(CH_2)_{0-4}$—$SO_2$—$NR_{220}R_{225}$; —$(CH_2)_{0-4}$—$S(O)_{0-2}$—$(C_1$-$C_8$ alkyl); —$(CH_2)_{0-4}$—$S(O)_{0-2}$—$(C_3$-$C_7$ cycloalkyl); —$(CH_2)_{0-4}$—N(H or $R_{215}$)—$CO_2R_{215}$; —$(CH_2)_{0-4}$—N(H or $R_{215}$)—$SO_2$—$R_{220}$; —$(CH_2)_{0-4}$—N(H or $R_{215}$)—CO—$N(R_{215})_2$; —$(CH_2)_{0-4}$—N (—H or $R_{215}$)—CO—$R_{220}$; —$(CH_2)_{0-4}$—$NR_{220}R_{225}$; —$(CH_2)_{0-4}$—O—CO—$(C_1$-$C_6$ alkyl); —$(CH_2)_{0-4}$—O—$(R_{215})$; —$(CH_2)_{0-4}$—S—$(R_{215})$; —$(CH_2)_{0-4}$—O—$(C_1$-$C_6$ alkyl optionally substituted with 1, 2, 3, or 5—F); —$C_2$-$C_6$ alkenyl optionally substituted with 1 or 2 $R_{205}$ groups; —$C_2$-$C_6$ alkynyl optionally substituted with 1 or 2 $R_{205}$ groups; adamantly, and —$(CH_2)_{0-4}$—$C_3$-$C_7$ cycloalkyl;

each aryl and heteroaryl group included within $R_{200}$ is optionally substituted with 1, 2, or 3 groups that are independently —$R_{205}$, —$R_{210}$ or —$C_1$-$C_6$ alkyl substituted with 1, 2, or 3 groups that are independently $R_{205}$ or $R_{210}$;

each heterocycloalkyl group included within $R_{200}$ is optionally substituted with 1, 2, or 3 groups that are independently $R_{210}$;

$R_{205}$ at each occurrence is independently selected from —$C_1$-$C_6$ alkyl, —$C_2$-$C_6$ alkenyl, —$C_2$-$C_6$ alkynyl, —$C_1$-$C_6$ haloalkoxy, —$(CH_2)_{0-3}$ $(C_3$-$C_7$ cycloalkyl), -halogen, —$(CH_2)_{0-6}$—OH, —O-phenyl, OH, SH, —$(CH_2)_{0-6}$—C≡N, —$(CH_2)_{0-6}$—C(=O) $NR_{235}R_{240}$, —$CF_3$, —$C_1$-$C_6$ alkoxy, $C_1$-$C_6$ alkoxycarbonyl, and —$NR_{235}R_{240}$;

$R_{210}$ at each occurrence is independently selected from —$C_1$-$C_6$ alkyl optionally substituted with 1, 2, or 3 $R_{205}$ groups; —$C_2$-$C_6$ alkenyl optionally substituted with 1, 2, or 3 $R_{205}$ groups; $C_1$-$C_6$ alkanoyl; —$SO_2$—$(C_1$-$C_6$ alkyl); —$C_2$-$C_6$ alkynyl optionally substituted with 1, 2, or 3 $R_{205}$ groups; -halogen; —$C_1$-$C_6$ alkoxy; —$C_1$-$C_6$ haloalkoxy; —$NR_{220}R_{225}$; —OH; —C≡N; —$C_3$-$C_7$ cycloalkyl optionally substituted with 1, 2, or 3 $R_{205}$ groups; —CO—$(C_1$-$C_4$ alkyl); $SO_2$—$NR_{235}R_{240}$; —CO—$NR_{235}R_{240}$; —$SO_2$—$(C_1$-$C_4$ alkyl); and =O;

$R_{215}$ at each occurrence is independently selected from —$C_1$-$C_6$ alkyl, —$(CH_2)_{0-2}$-(aryl), —$C_2$-$C_6$ alkenyl, —$C_2$-$C_6$ alkynyl, —$C_3$-$C_7$ cycloalkyl, —$(CH_2)_{0-2}$-(heteroaryl), and —$(CH_2)_{0-2}$-(heterocycloalkyl); wherein the aryl group included within $R_{215}$ is optionally substituted with 1, 2, or 3 groups that are independently —$R_{205}$ or —$R_{210}$; wherein the heterocycloalkyl and heteroaryl groups included within $R_{215}$ are optionally substituted with 1, 2, or 3 $R_{210}$;

$R_{220}$ at each occurrence is independently H, —$C_1$-$C_6$ alkyl, —CHO, hydroxy $C_1$-$C_6$ alkyl, $C_1$-$C_6$ alkoxycarbonyl, -amino $C_1$-$C_6$ alkyl, —$SO_2$—$C_1$-$C_6$ alkyl, $C_1$-$C_6$ alkanoyl optionally substituted with up to three halogens, —$C(O)NH_2$, —$C(O)NH(C_1$-$C_6$ alkyl), —$C(O)N(C_1$-$C_6$ alkyl)$(C_1$-$C_6$ alkyl), -halo $C_1$-$C_6$ alkyl, —$(CH_2)_{0-2}$—$(C_3$-$C_7$ cycloalkyl), —$(C_1$-$C_6$ alkyl)-O—$(C_1$-$C_3$ alkyl), —$C_2$-$C_6$ alkenyl, —$C_2$-$C_6$ alkynyl, -aryl, -heteroaryl, or -heterocycloalkyl; wherein the aryl, heteroaryl and heterocycloalkyl groups included within $R_{220}$ and $R_{225}$ is optionally substituted with 1, 2, or 3 $R_{270}$ groups, $R_{270}$ at each occurrence is independently —$R_{205}$, —$C_1$-$C_6$ alkyl optionally substituted with 1, 2, or 3 $R_{205}$ groups; —$C_2$-$C_6$ alkenyl optionally substituted with 1, 2, or 3 $R_{205}$ groups; —$C_2$-$C_6$ alkynyl optionally substituted with 1, 2, or 3 $R_{205}$ groups; -phenyl; -halogen; —$C_1$-$C_6$ alkoxy; —$C_1$-$C_6$ haloalkoxy; —$NR_{235}R_{240}$; —OH; —C≡N; —$C_3$-$C_7$ cycloalkyl optionally substituted with 1, 2, or 3 $R_{205}$ groups; —CO—$(C_1$-$C_4$ alkyl); —$SO_2$—$NR_{235}R_{240}$; —CO—$NR_{235}R_{240}$; —$SO_2$—$(C_1$-$C_4$ alkyl); and =O;

$R_{235}$ and $R_{240}$ at each occurrence are independently —H, —$C_1$-$C_6$ alkyl, $C_2$-$C_6$ alkanoyl, —$SO_2$—$(C_1$-$C_6$ alkyl), or -phenyl;

$R_{245}$ and $R_{250}$ at each occurrence are independently selected from H, —$(CH_2)_{0-4}CO_2C_1$-$C_4$ alkyl, —$(CH_2)_{0-4}C(=O)C_1$-$C_4$ alkyl, —$C_1$-$C_4$ alkyl, —$C_1$-$C_4$ hydroxyalkyl, —$C_1$-$C_4$ alkoxy, —$C_1$-$C_4$ haloalkoxy, —$(CH_2)_{0-4}$—$C_3$-$C_7$ cycloalkyl, —$C_2$-$C_6$ alkenyl, —$C_2$-$C_6$ alkynyl, —$(CH_2)_{0-4}$ aryl, —$(CH_2)_{0-4}$ heteroaryl, and —$(CH_2)_{0-4}$ heterocycloalkyl, or $R_{245}$ and $R_{250}$ are taken together with the carbon to which they are attached to form a monocycle or bicycle of 3, 4, 5, 6, 7 or 8 carbon atoms, where 1, 2, or 3 carbon atoms are optionally replaced by 1, 2, or 3 gropus that are independently —O—, —S—, —$SO_2$—, —C(O)—, —$NR_{220}$—, or —$NR_{220}R_{220}$— wherein both $R_{220}$ groups are alkyl; and wherein the ring is optionally substituted with 1, 2, 3, 4, 5, or 6 groups that are independently $C_1$-$C_4$ alkyl, $C_1$-$C_4$ alkoxy, hydroxyl, $NH_2$, $NH(C_1$-$C_6$ alkyl), $N(C_1$-$C_6$ alkyl)$(C_1$-$C_6$ alkyl), —NH—$C(O)C_1$-$C_5$ alkyl, —NH—$SO_2$—$(C_1$-$C_6$ alkyl), or halogen;

wherein the aryl, heteroaryl or heterocycloalkyl groups included within $R_{245}$ and $R_{250}$ are optionally substituted with 1, 2, or 3 groups that are independenly halogen, $C_{1-6}$ alkyl, CN or OH.

3. A compound according to claim 2, wherein
$R_1$ is $C_1$-$C_{10}$ alkyl optionally substituted with 1 or 2 groups independently selected from halogen, —OH, =O, —CN, —CF$_3$, —OCF$_3$, —C$_3$-C$_7$ cycloalkyl, —C$_1$-C$_4$ alkoxy, amino, mono-dialkylamino, aryl, heteroaryl or heterocycloalkyl, wherein the aryl group is optionally substituted with 1 or 2 $R_{50}$ groups;

$R_{50}$ is halogen, OH, CN, —CO—(C$_1$-C$_4$ alkyl), —NR$_7$R$_8$, C$_1$-C$_6$ alkyl, C$_2$-C$_6$ alkenyl, C$_2$-C$_6$ alkynyl, C$_1$-C$_6$ alkoxy, and C$_3$-C$_8$ cycloalkyl;

$R_7$ and $R_8$ are selected from H; —C$_1$-C$_4$ alkyl optionally substituted with 1, 2, or 3 groups selected from —OH, —NH$_2$ and halogen; —C$_3$-C$_6$ cycloalkyl; —(C$_1$-C$_4$ alkyl)-O—(C$_1$-C$_4$ alkyl); —C$_2$-C$_4$ alkenyl; and —C$_2$-C$_4$ alkynyl;

$R_C$ is selected from —(CR$_{245}$R$_{250}$)$_{0-4}$-aryl; —(CR$_{245}$R$_{250}$)$_{0-4}$-heteroaryl; —(CR$_{245}$R$_{250}$)$_{0-4}$-heterocycloalkyl; where the aryl and heteroaryl groups attached to the —(CR$_{245}$R$_{250}$)$_{0-4}$— group are optionally substituted with 1, 2, 3 or 4 $R_{200}$ groups; where the heterocycloalkyl group attached to the —(CR$_{245}$R$_{250}$)$_{0-4}$ group is optionally substituted with 1, 2, 3, or 4 $R_{210}$ groups; and $R_{245}$, $R_{250}$, $R_{200}$, and $R_{210}$ are as defined above.

4. A compound according to claim 3, wherein
$R_C$ is —(CR$_{245}$R$_{250}$)$_{0-4}$-heterocycloalkyl; where the heterocycloalkyl attached to the —(CR$_{245}$R$_{250}$)$_{0-4}$— group is optionally substituted with 1, 2, 3, or 4 $R_{210}$ groups, wherein $R_{245}$, $R_{250}$, and $R_{210}$ are as defined above.

5. A compound according to claim 4, wherein
$R_1$ is $C_1$-$C_{10}$ alkyl substituted with one aryl group, where the aryl group is optionally substituted with 1 or 2 $R_{50}$ groups;
$R_C$ is —(CR$_{245}$R$_{250}$)$_{1-4}$-aryl or —(CR$_{245}$R$_{250}$)$_{0-4}$-heteroaryl, $R_{245}$ and $R_{250}$ are independently selected from H, —(CH$_2$)$_{0-4}$CO$_2$C$_1$-C$_4$ alkyl, —(CH$_2$)$_{0-4}$CO$_2$H, —C$_1$-C$_4$ alkyl, —(C$_1$-C$_4$ alkyl)OH, or $R_{245}$, $R_{250}$ and the carbon to which they are attached form a monocycle or bicycle of 3, 4, 5, 6, 7 or 8 carbon atoms, where 1 or 2 carbon atoms are optionally replaced by —O—, —S—, —SO$_2$—, or —NR$_{220}$—, where $R_{220}$ is as defined above; and wherein the aryl and heteroaryl groups attached to the —(CR$_{245}$R$_{250}$)$_{1-4}$— groups are optionally substituted with 1 or 2 $R_{200}$ groups.

6. A compound according to claim 2, wherein
$R_C$ is (CR$_{245}$R$_{250}$)$_1$-aryl, where the aryl (preferably phenyl or naphthyl, more preferably phenyl) is optionally substituted with 1, 2, or 3 $R_{200}$ groups; and $R_{245}$ is H and $R_{250}$ is H or C$_1$-C$_6$ alkyl; or
$R_{245}$ and $R_{250}$ are independently C$_1$-C$_3$ alkyl (preferably both are methyl); or
CR$_{245}$R$_{250}$ represents a C$_3$-C$_7$ cycloalkyl group.

7. A compound according to claim 6, wherein
the (CR$_{245}$R$_{250}$)$_1$-aryl is (CR$_{245}$R$_{250}$)$_1$-phenyl where the phenyl is optionally substituted with 1, 2, or 3 $R_{200}$ groups.

8. A compound according to claim 7, wherein the phenyl in (CR$_{245}$R$_{250}$)$_1$-phenyl is substituted with 1-3 independently selected $R_{200}$ groups, or 1 or 2 independently selected $R_{200}$ groups, and 1 heteroaryl group optionally substituted with 1 $R_{200}$ group or 1 phenyl group optionally substituted with 1 $R_{200}$ group.

9. A compound according to claim 7, wherein $R_{245}$ is hydrogen and $R_{250}$ is C$_1$-C$_3$ alkyl.

10. A compound according to claim 7, wherein $R_{245}$ and $R_{250}$ are both hydrogen.

11. A compound according to claim 7, wherein the phenyl in (CR$_{245}$R$_{250}$)$_1$-phenyl is substituted with
(a) 1 $R_{200}$ group and 1 heteroaryl group, wherein the heteroaryl is optionally substituted with 1 $R_{200}$ group; or
(b) 1 $R_{200}$ group and 1 phenyl group, wherein the 1 phenyl group is optionally substituted with 1 $R_{200}$ group; or
(c) 1 $R_{200}$ group, and 1 heterocycloalkyl group wherein the heterocycloalkyl group is optionally substituted with 1 $R_{200}$ group or =O.

12. A compound according to claim 11, wherein CR$_{245}$R$_{250}$ represents a C$_3$-C$_7$ cycloalkyl group.

13. A compound according to claim 11, wherein CR$_{245}$R$_{250}$ represents a C$_5$-C$_7$ cycloalkyl group.

14. A compound according to claim 11, wherein CR$_{245}$R$_{250}$ represents a C$_3$-C$_6$ cycloalkyl group.

15. A compound according to claim 11, wherein CR$_{245}$R$_{250}$ represents a C$_6$ cycloalkyl.

16. A compound according to claim 7,
wherein the phenyl in (CR$_{245}$R$_{250}$)$_1$-phenyl is substituted with 1 $R_{200}$ group; or
1 $R_{200}$ group and one heteroaryl group wherein the heteroaryl group is optionally substituted with
1 $R_{200}$ group or
1 $R_{200}$ group and 1 phenyl group wherein the 1 phenyl group is optionally substituted with one $R_{200}$ group.

17. A compound according to claim 7, wherein the phenyl in (CR$_{245}$R$_{250}$)$_1$-phenyl is substituted with 1 $R_{200}$ group.

18. A compound selected from the group consisting of:
methyl (3S)-3-{[(2R,3S)-3-[(anilinocarbonyl)amino]-4-(3,5-difluorophenyl)-2-hydroxybutyl]amino}-3-(3-bromophenyl)propanoate;

N-((1S,2R)-1-(3,5-difluorobenzyl)-3-{[4-(3-ethylphenyl)tetrahydro-2H-pyran-4-yl]amino}-2-hydroxypropyl)-N'-phenylurea;

N-benzyl-N'-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)urea;

N-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)-N'-phenylurea;

N-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)-N'-propylurea;

N-(sec-butyl)-N'-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)urea;

N-{(1S,2R)-1-(3,5-difluorobenzyl)-3-[(6-ethyl-3,4-dihydro-2H-chromen-4-yl)amino]-2-hydroxypropyl}-N'-phenylurea;

N-{(1S,2R)-1-(3,5-difluorobenzyl)-2-hydroxy-3-[(6-isopropyl-3,4-dihydro-2H-chromen-4-yl)amino]propyl}-N'-phenylurea;

N-[(1S,2R)-1-(3,5-difluorobenzyl)-3-({6-[(dimethylamino)methyl]-3,4-dihydro-2H-chromen-4-yl}amino)-2-hydroxypropyl]-N'-phenylurea;

N-{(1S,2R)-1-(3,5-difluorobenzyl)-3-[(6-ethyl-3,4-dihydro-1H-isochromen-4-yl)amino]-2-hydroxypropyl}-N'-phenylurea;

N-{(1S,2R)-1-(3,5-difluorobenzyl)-2-hydroxy-3-[(6-isopropyl-3,4-dihydro-1H-isochromen-4-yl)amino]propyl}-N'-phenylurea;

N-[(1S,2R)-1-(3,5-difluorobenzyl)-3-({6-[(dimethylamino)methyl]-3,4-dihydro-1H-isochromen-4-yl}amino)-2-hydroxypropyl]-N'-phenylurea;

$N^3$-[({(1S,2R)-1-(3,5-difluorobenzyl)-2-hydroxy-3-[(3-methoxybenzyl)amino]propyl}amino) carbonyl]-$N^1$, $N^1$-dipropyl-b-alaninamide; and 2-{[({(1S,2R)-1-(3,5-difluorobenzyl)-2-hydroxy-3-[(3-methoxybenzyl)amino]propyl}amino)carbonyl] amino}-N,N-dipropylethanesulfonamide.

19. A compound which has the formula:

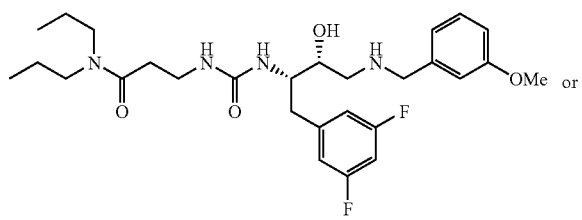

or a pharmaceutically acceptable salt thereof.

20. The compound according to claim 1 that is 3-(3-((2S, 3R)-1-(3,5-difluorophenyl)-4-(1-(3-ethylphenyl)butylamino)-3-hydroxybutan-2-yl)ureido)-N,N-dipropylpropanamide.

21. A method of treating a patient who has Alzheimer's Disease who is in need of such treatment which comprises administration of a therapeutically effective amount of a compound of claim 1 or a pharmaceutically acceptable salt or ester thereof.

* * * * *

SEQUENCE LISTING

```
<160> NUMBER OF SEQ ID NOS: 9

<210> SEQ ID NO 1
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 1

Ser Glu Val Asn Leu Asp Ala Glu Phe Arg Cys Lys Lys
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
```

```
<222> LOCATION: (11)..(11)
<223> OTHER INFORMATION: covalent attachment of oregon green

<400> SEQUENCE: 2

Ser Glu Val Lys Met Asp Ala Glu Phe Arg Cys Lys Lys
1               5                   10

<210> SEQ ID NO 3
<211> LENGTH: 22
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

Gly Leu Asn Ile Lys Thr Glu Glu Ile Ser Glu Ile Ser Tyr Glu Val
1               5                   10                  15

Glu Phe Arg Cys Lys Lys
            20

<210> SEQ ID NO 4
<211> LENGTH: 34
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (32)..(32)
<223> OTHER INFORMATION: covalent attachment of oregon green

<400> SEQUENCE: 4

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Arg Cys
            20                  25                  30

Lys Lys

<210> SEQ ID NO 5
<211> LENGTH: 33
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (7)..(7)
<223> OTHER INFORMATION: oxidized cysteine
<220> FEATURE:
<221> NAME/KEY: MISC_FEATURE
<222> LOCATION: (19)..(19)
<223> OTHER INFORMATION: oxidized cysteine
<220> FEATURE:
<221> NAME/KEY: MISC_FEATURE
```

```
<222> LOCATION: (31)..(31)
<223> OTHER INFORMATION: covalent attachment of oregon green

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Cys Lys
            20                  25                  30

Lys

<210> SEQ ID NO 6
<211> LENGTH: 33
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 6

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 7
<211> LENGTH: 29
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 7

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial sequence
<220> FEATURE:
<223> OTHER INFORMATION: synthetic peptide

<400> SEQUENCE: 8

Ser Glu Val Asn Leu Asp Ala Glu Phe
1               5

<210> SEQ ID NO 9
<211> LENGTH: 30
<212> TYPE: PRT
<213> ORGANISM: Artificial sequence
<220> FEATURE:
<223> OTHER INFORMATION: synthetic peptide
```

```
<400> SEQUENCE: 9

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
        20                  25                  30
```